United States Patent
Hatakeyama et al.

(10) Patent No.: US 9,741,950 B2
(45) Date of Patent: *Aug. 22, 2017

(54) POLYCYCLIC AROMATIC COMPOUND

(71) Applicants: KYOTO UNIVERSITY, Kyoto (JP); JNC CORPORATION, Tokyo (JP)

(72) Inventors: Takuji Hatakeyama, Uji (JP); Masaharu Nakamura, Uji (JP); Sigma Hashimoto, Uji (JP)

(73) Assignees: KYOTO UNIVERSITY, Kyoto (JP); JNC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/832,414

(22) Filed: Aug. 21, 2015

(65) Prior Publication Data
US 2016/0049600 A1 Feb. 18, 2016

Related U.S. Application Data

(62) Division of application No. 14/003,945, filed as application No. PCT/JP2012/056206 on Mar. 9, 2012, now Pat. No. 9,166,176.

(30) Foreign Application Priority Data

Mar. 10, 2011 (JP) ................................. 2011-053242

(51) Int. Cl.
| | |
|---|---|
| C07F 5/02 | (2006.01) |
| H01L 51/50 | (2006.01) |
| H01L 51/00 | (2006.01) |
| C07F 9/6584 | (2006.01) |
| C07F 9/6587 | (2006.01) |
| C09K 11/06 | (2006.01) |
| H05B 33/14 | (2006.01) |
| C07F 7/10 | (2006.01) |
| C07F 7/22 | (2006.01) |
| C07F 7/30 | (2006.01) |
| H01L 51/05 | (2006.01) |
| H01L 51/42 | (2006.01) |

(52) U.S. Cl.
CPC ............ *H01L 51/0094* (2013.01); *C07F 5/02* (2013.01); *C07F 7/10* (2013.01); *C07F 7/2284* (2013.01); *C07F 7/30* (2013.01); *C07F 9/6587* (2013.01); *C07F 9/65846* (2013.01); *C09K 11/06* (2013.01); *H01L 51/008* (2013.01); *H01L 51/0071* (2013.01); *H01L 51/0077* (2013.01); *H05B 33/14* (2013.01); *C09K 2211/104* (2013.01); *H01L 51/0558* (2013.01); *H01L 51/42* (2013.01); *H01L 51/5012* (2013.01); *H01L 51/5056* (2013.01); *H01L 51/5072* (2013.01); *Y02E 10/549* (2013.01)

(58) Field of Classification Search
USPC ............ 548/405, 402, 412; 313/504; 549/4; 546/13
See application file for complete search history.

(56) References Cited

U.S. PATENT DOCUMENTS

| | | | | |
|---|---|---|---|---|
| 9,166,176 B2 * | 10/2015 | Hatakeyama | ....... | C07F 9/65846 |
| 2003/0127967 A1 | 7/2003 | Tsutsui et al. | | |

FOREIGN PATENT DOCUMENTS

| | | |
|---|---|---|
| JP | 2006-004721 | 1/2006 |
| JP | 2007-27141 | 2/2007 |
| JP | 2008-171832 | 7/2008 |
| WO | 2010/104047 | 9/2010 |

OTHER PUBLICATIONS

International Search Report issued May 29, 2012 in International (PCT) Application No. PCT/JP2012/056206.
J. Q. Hou et al., "DFT Study on the Stabilities of the Heteroflullerenes $Sc_3N@C_{67}B$, $Sc_3N@C_{67}N$, and $Sc_3N@C_{66}BN$", J. Phys. Chem., vol. 111, pp. 1111-1116, 2007.
M. S. Mudadu et al., "Preparation and Study of 1,8-Di(pyrid-2'-yl)carbazoles", J. Org. Chem., vol. 73, pp. 6513-6520, 2008.
T. Hatakeyama et al., "Synthesis of BN-Fused Polycyclic Aromatics via Tandem Intramolecular Electrophilic Arene Borylation", Journal of the American Chemical Society, vol. 133, pp. 18614-18617, Oct. 25, 2011.
Extended Supplementary European Search Report dated Aug. 12, 2014 in European Application No. 12755603.3.
L. Ci et al., "Atomic Layers of Hybridized Boron Nitride and Graphene Domains", Nature Materials, vol. 9, No. 5, pp. 430-435, Feb. 28, 2010.
J. Pattanayak et al., "Boron-Nitrogen (BN) Substitution Patterns in C/BN Hybrid Fullerenes: $C_{60-2x}(BN)_x(X=1-7)$", The Journal of Physical Chemistry, vol. 105, No. 36, pp. 8376-8384, Sep. 1, 2001.
Office Action dated Nov. 4, 2014 for CN Patent Application No. 201280012314.2 (English translation of cover page).
J. Pattanayak et al., "Comparison of BN and AlN Substitution on the Structure and Electronic and Chemical Properties of $C_{60}$ Fullerene", J. Phys. Chem. A, vol. 107, pp. 4056-4065, 2003.
M. Dietrich et al., "Electrochemical Oxidation and Structural Changes of 5,6-Dihydrobenzo[c]cinnolines", J. Am Chem. Soc., vol. 118, pp. 5020-5030, 1996.

\* cited by examiner

*Primary Examiner* — Charanjit Aulakh
(74) *Attorney, Agent, or Firm* — Wenderoth, Lind & Ponack, L.L.P.

(57) ABSTRACT

The invention provides a polycyclic aromatic compound or a salt thereof having a partial structure represented by the following general formula (I):

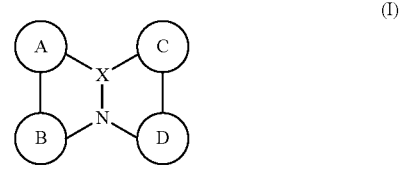

wherein X, ring A, ring B, ring C, and ring D are as defined in the specification.

7 Claims, 2 Drawing Sheets
(2 of 2 Drawing Sheet(s) Filed in Color)

FIGURE 1

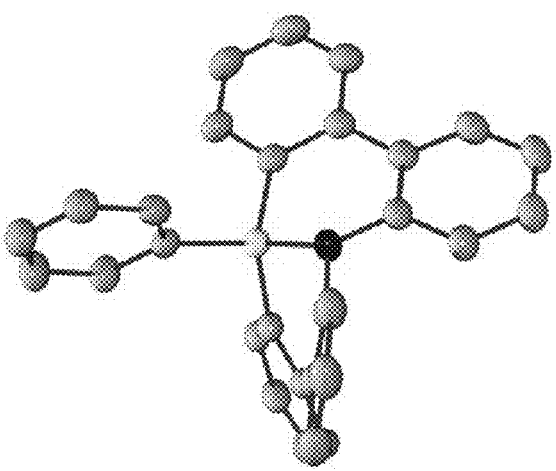

| Formula | $C_{30}H_{21}NSi$ | Abs. Coefficient, $cm^{-1}$ | 0.127 |
|---|---|---|---|
| Formula Weight | 423.57 | F(000) | 888.00 |
| Temperature, K | 100(2) | Crystal Size, $mm^3$ | 0.05, 0.02, 0.01 |
| Wavelength, Å | 0.71069 | $2\theta_{min}, 2\theta_{max}, \deg$ | 3.78, 51.0 |
| Crystal System | Monoclinic | Index Ranges | $-10 \leq h \leq 11$ |
| Space Group | $P2_1/n$ (No. 14) | | $-18 \leq k \leq 19$ |
| $a$, Å | 9.2321(2) | | $-17 \leq l \leq 17$ |
| $b$, Å | 16.4740(4) | Reflections (unique) | 3878 |
| $c$, Å | 14.2878(3) | Reflections ($I>2.0\sigma(I)$) | 3371 |
| $\alpha$, deg | 90 | Parameters | 289 |
| $\beta$, deg | 96.1539(8) | GOF on $F^2$ | 1.087 |
| $\gamma$, deg | 90 | $R_1$ ($I>2.0\sigma(I)$) | 0.0538 |
| Volume, Å | 2160.50(8) | $R$, $wR_2$ (all data) | 0.0632, 0.1387 |
| Z | 4 | Largest diff peak and hole, e, $Å^{-3}$ | 0.560, −0.494 |
| $Density_{calcd}$, $g \cdot cm^{-3}$ | 1.302 | | |

FIGURE 2

| Formula | $C_{30}H_{21}NGe$ | Abs. Coefficient, $cm^{-1}$ | 1.416 |
|---|---|---|---|
| Formula Weight | 468.09 | F(000) | 480.00 |
| Temperature, K | 173 | Crystal Size, $mm^3$ | 0.2, 0.2, 0.2 |
| Wavelength, Å | 0.71070 | $2\theta_{min}, 2\theta_{max}$, deg | 6.3, 54.9 |
| Crystal System | Triclinic | Index Ranges | $-11 \leq h \leq 11$ |
| Space Group | P–1 (No. 2) | | $-12 \leq k \leq 12$ |
| $a$, Å | 9.655(3) | | $-15 \leq l \leq 15$ |
| $b$, Å | 10.225(2) | Reflections (unique) | 4293 |
| $c$, Å | 12.886(3) | Reflections ($I>2.0\sigma(I)$) | 3856 |
| $\alpha$, deg | 67.894(11) | Parameters | 289 |
| $\beta$, deg | 71.624(11) | GOF on $F^2$ | 1.046 |
| $\gamma$, deg | 72.722(13) | $R_1$ ($I>2.0\sigma(I)$) | 0.0300 |
| Volume, Å | 1095.4(5) | $R$, $wR_2$ (all data) | 0.0347, 0.0705 |
| Z | 2 | Largest diff peak and hole, e, $Å^{-3}$ | 0.440, −0.290 |
| Density$_{calcd}$, $g \cdot cm^{-3}$ | 1.419 | | |

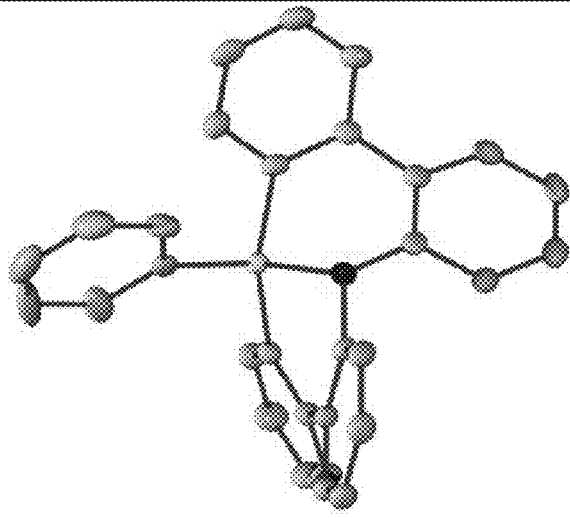

POLYCYCLIC AROMATIC COMPOUND

TECHNICAL FIELD

The present invention relates to a new compound. Specifically, the present invention relates to a polycyclic aromatic compound including a nitrogen atom, and another heteroatom or a metal atom. The present invention also relates to electrochemical devices, such as organic thin-film solar cells, organic thin-film transistors, and organic light-emitting elements such as organic light-emitting diodes and organic EL devices, including the compound.

BACKGROUND ART

Hitherto, research has been conducted on α-NPD, rubrene, Alq3, PBD, and the like, as a luminescent material and an organic semiconductor material used in organic light-emitting elements such as organic EL devices and organic light-emitting diodes (Patent Literature 1 to 3).

In an organic light-emitting element, a thin film including a fluorescent organic compound or a phosphorescent organic compound is sandwiched between a positive electrode and a negative electrode. The element utilizes light radiated when an exciton of the fluorescent compound or the phosphorescent compound, generated through injection of electron or hole (positive hole) from the respective electrodes, returns to a ground state.

Recent progresses regarding organic light-emitting elements have been remarkable. Since the elements have characteristics enabling realization of a lightweight and thin luminous device that has high-speed response, a diverse luminous wavelength, and high brightness when low voltage is applied thereto, a wide range of possible applications thereof is suggested.

However, presently, the output of light with further high brightness or high conversion efficiency is required. In addition, there are still many problems regarding durability, such as changes observed over time after being used for a long period of time, and deterioration due to moisture and atmosphere gas containing oxygen. Furthermore, although light emission of red, green, and blue with fine color purity is required when considering application thereof to a full-color display or the like, there has not been a sufficient answer for such problems.

Patent Literature 4 discloses a polycyclic aromatic compound having a single heteroatom in a non-aromatic ring.

CITATION LIST

Patent Literature

PTL 1: Japanese Unexamined Patent Publication No. 2008-171832

PTL 2: Japanese Unexamined Patent Publication No. 2007-027141

PTL 3: Japanese Unexamined Patent Publication No. 2006-004721

PTL 4: WO2010/104047

SUMMARY OF INVENTION

Technical Problem

An object of the present invention is to provide a new polycyclic aromatic compound, and an electrochemical device including the compound such as an organic thin-film solar cell, an organic thin-film transistor, or an organic light-emitting element.

Solution to Problem

The present inventors provide a new polycyclic aromatic compound in which a nitrogen atom, and another heteroatom or a metal atom (X) are arranged adjacent to each other in a non-aromatic ring; and an electrochemical device including the compound such as an organic thin-film solar cell, an organic thin-film transistor, and an organic light-emitting element.

Item 1. A polycyclic aromatic compound or a salt thereof having a partial structure represented by the following general formula (I).

$$\text{(I)}$$

(In the formula,

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.

Ring A, ring B, ring C, and ring D are the same or different, and each represents an optionally substituted aromatic ring or an optionally substituted heteroaromatic ring.)

Item 2. The polycyclic aromatic compound or a salt thereof according to item 1, having a partial structure represented by the following general formula (II).

$$\text{(II)}$$

(In the formula, $Y^a$s are the same or different, and each represents C— or N; or two adjacent $Y^a$s on the same ring, together with a bond therebetween, form N—, O, S, or Se.

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.)

Item 3. The polycyclic aromatic compound or a salt thereof according to item 1 or 2, having a partial structure represented by the following general formula (II-1).

(II-1)

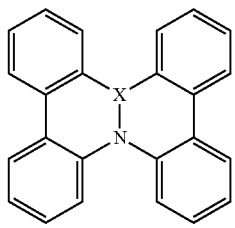

(In the formula,

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.)

Item 4. The polycyclic aromatic compound or a salt thereof according to any one of items 1 to 3, having a partial structure represented by any of the following general formulae (II-2) to (II-54).

(II-2)

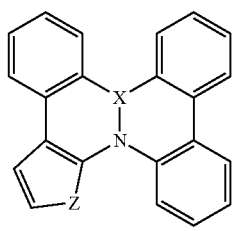

(II-3)

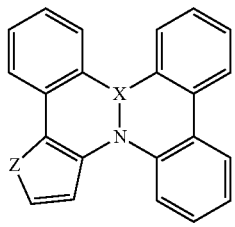

(II-4)

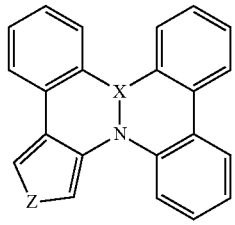

(II-5)

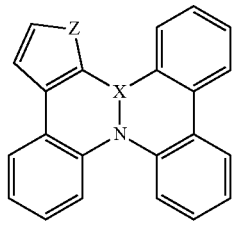

(II-6)

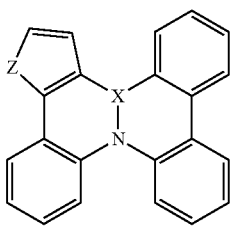

(II-7)

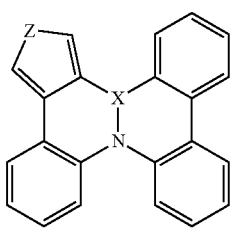

(II-8)

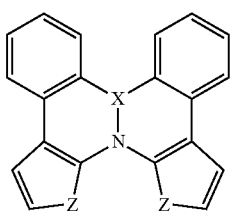

(II-9)

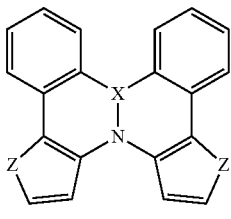

(II-10)

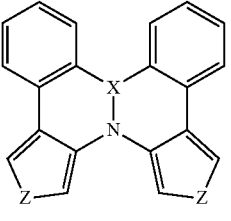

(II-11)

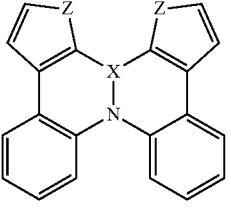

(II-12)

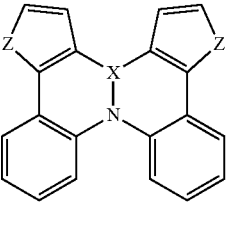

(II-13) 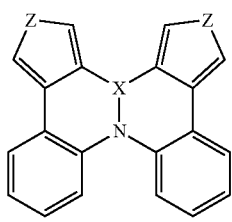
(II-14) 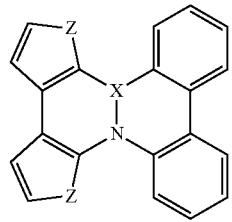
(II-15) 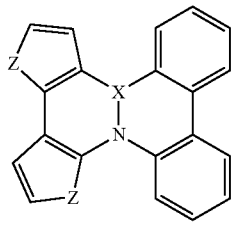
(II-16) 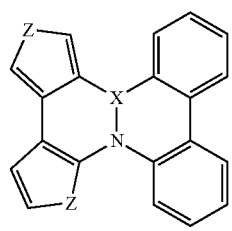
(II-17) 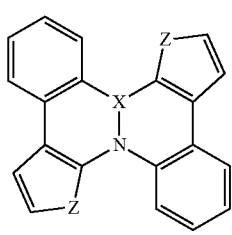
(II-18) 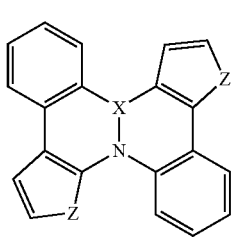
(II-19) 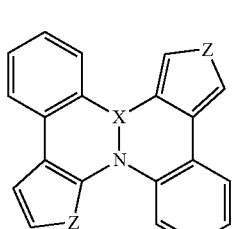
(II-20) 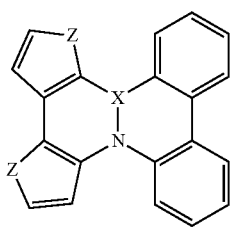
(II-21) 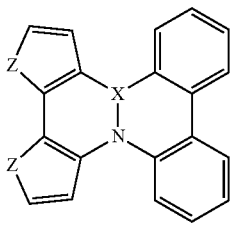
(II-22) 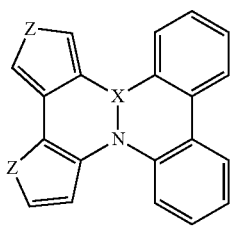
(II-23) 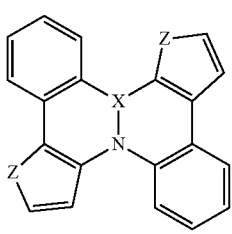
(II-24) 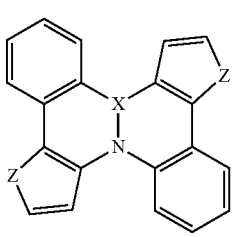
(II-25) 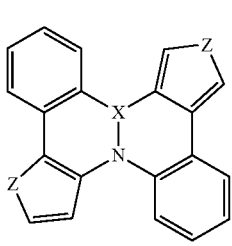
(II-26) 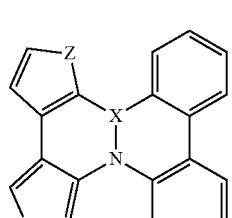

(II-27) 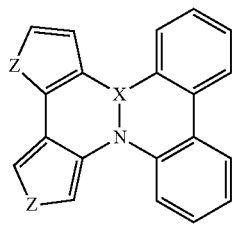
(II-28) 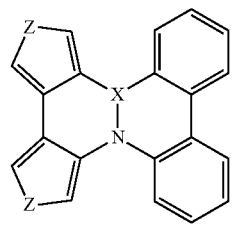
(II-29) 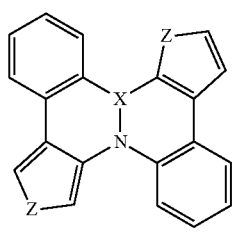
(II-30) 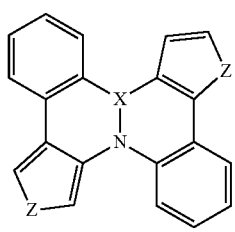
(II-31) 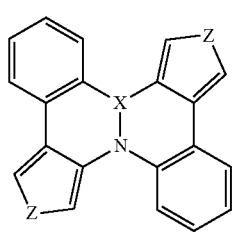
(II-32) 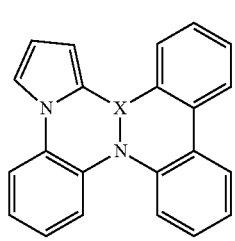
(II-33) 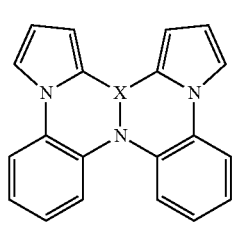
(II-34) 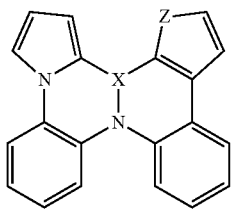
(II-35) 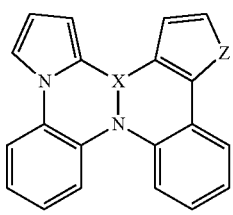
(II-36) 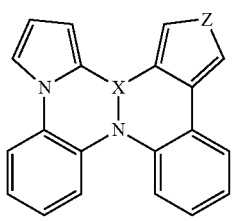
(II-37) 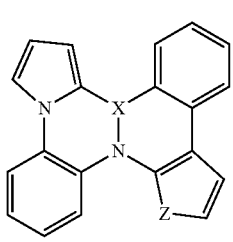
(II-38) 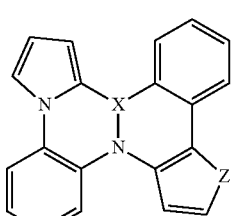
(II-39) 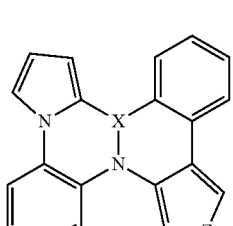
(II-40) 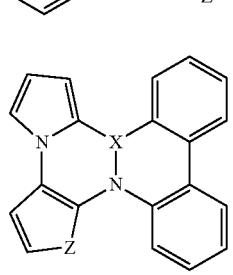

(II-41) 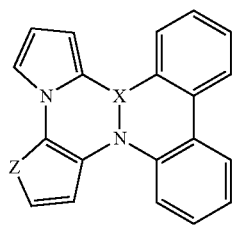
(II-42) 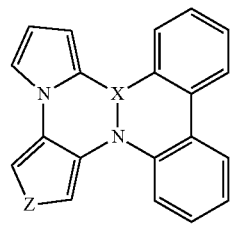
(II-43) 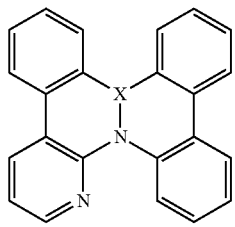
(II-44) 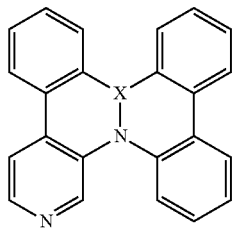
(II-45) 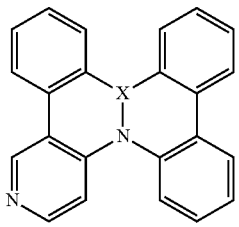
(II-46) 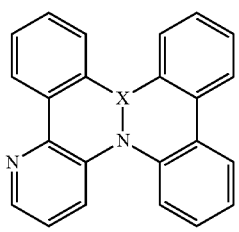
(II-47) 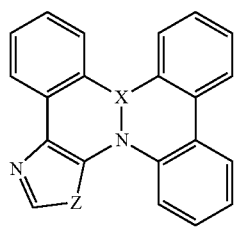
(II-48) 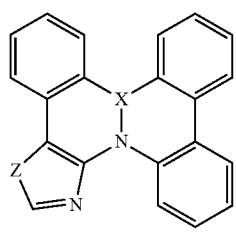
(II-49) 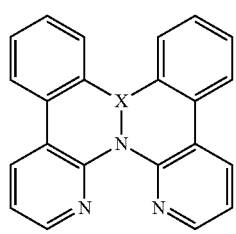
(II-50) 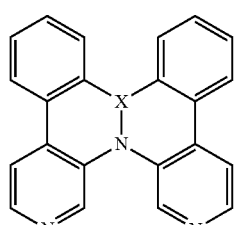
(II-51) 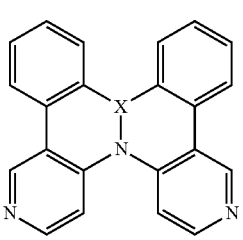
(II-52) 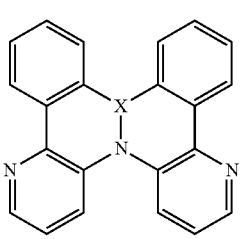
(II-53) 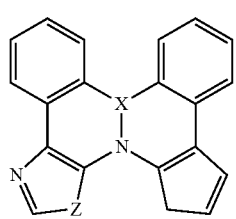

(II-54)

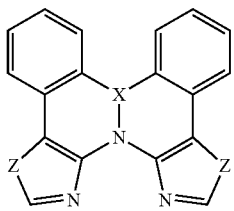

(In the formulae,
X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.

Z represents Se, S, O, or N—.)

Item 5. The polycyclic aromatic compound or a salt thereof according to any one of items 1 to 4 represented by the following general formula (II').

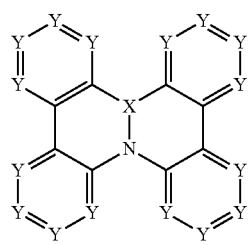

(II')

(In the formula,
Ys are the same or different, and each represents CR or N; or two adjacent Ys on the same ring, together with a bond therebetween, form NR, O, S, or Se.

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.

R represents a hydrogen atom, halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, cyano group, nitro group, amino group, monoalkylamino group, monoarylamino group, monoheteroarylamino group, carbazole group, $C_{1-20}$ alkoxycarbonylamino group, carbamoyl group, mono- or di-alkylcarbamoyl group, sulfamoyl group, mono- or di-alkylsulfamoyl group, $C_{1-20}$ alkylsulfonylamino group, $C_{1-20}$ alkylcarbonylamino group, aryl group, heteroaryl group, $C_{1-20}$ alkoxycarbonyl group, carboxyl group, 5-tetrazolyl group, sulfo group (—SO$_2$OH), fluorosulfonyl group, SR$^a$, N(R$^a$)$_2$, B(R$^a$)$_2$, Si(R$^a$)$_3$, or —C≡C—Si(R$^a$)$_3$ (wherein R$^a$ represents an optionally substituted alkyl group, an optionally substituted aryl group, or an optionally substituted heteroaryl group; or two R$^a$s, together with an atom bound thereto, may form a bicyclic group or a tricyclic group optionally having a heteroatom);

provided that the alkyl group, the alkenyl group, the alkynyl group, and the alkoxy group are each optionally substituted with 1 to 3 atoms or groups, selected from the group consisting of halogen atom, hydroxy group, $C_{1-20}$ alkoxy group, aryloxy group, amino group, carbazole group, N(R$^a$)$_2$ (wherein R$^a$ is as defined above), trifluoromethyl group, $C_{2-12}$ perfluoroalkyl group, $C_{3-8}$ cycloalkyl group, aryl group, and heteroaryl group; and the aryl group, aryl moiety, heteroaryl group, heteroaryl moiety, and carbazole group are each optionally substituted with 1 to 5 atoms or groups, selected from the group consisting of halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, cyano group, nitro group, amino group, carbazole group, monoalkylamino group, monoarylamino group, monoheteroarylamino group, N(R$^a$)$_2$ (wherein R$^a$ is as defined above), carbamoyl group, mono- or di-alkylcarbamoyl group, sulfamoyl group, mono- or di-alkylsulfamoyl group, $C_{1-20}$ alkylcarbonyl group, $C_{1-20}$ alkylsulfonyl group, $C_{1-20}$ alkylsulfonylamino group, $C_{1-20}$ alkylcarbonylamino group, methylenedioxy group, heteroaryl group, and aryl group (wherein the aryl group is optionally substituted with 1 to 5 atoms or groups, selected from the group consisting of halogen atom, $C_{1-20}$ alkyl group, $C_{3-8}$ cycloalkyl group, $C_{2-20}$ alkenyl group, $C_{2-20}$ alkynyl group, hydroxy group, trifluoromethyl group, $C_{2-12}$ perfluoroalkyl group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, methylenedioxy group, cyano group, nitro group, amino group, carbazole group, and N(R$^a$)$_2$ (wherein R$^a$ is as defined above)).

Or, two adjacent Rs, together with carbon atom bound thereto, form a five- or six-membered monocyclic group, bicyclic group, or tricyclic group optionally having a heteroatom; or three adjacent Rs form, together with carbon atom bound thereto, a bicyclic group or a tricyclic group optionally having a heteroatom.

When two adjacent Rs are Rs in adjacent rings, the two Rs form a single bond, CH$_2$, CHR$^a$, CR$^a{}_2$, NR$^a$, Si(R$^a$)$_2$, BR$^a$ (wherein R$^a$ is as defined above), Se, S, or O.)

Item 6. The polycyclic aromatic compound or a salt thereof according to any one of items 1 to 5 represented by the following general formula (II'-1).

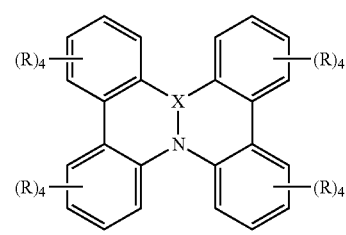

(II'-1)

(In the formula,
X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.

R represents a hydrogen atom, halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, cyano group, nitro group, amino group, monoalkylamino group, monoarylamino group, monoheteroarylamino group, carbazole group, $C_{1-20}$ alkoxycarbonylamino group, carbamoyl group, mono- or di-alkylcarbamoyl group, sulfamoyl group, mono- or di-alkylsulfamoyl group, $C_{1-20}$ alkylsulfonylamino group, $C_{1-20}$ alkylcarbonylamino group, aryl group, heteroaryl group, $C_{1-20}$ alkoxycarbonyl group, carboxyl group, 5-tetrazolyl group, sulfo group (—SO$_2$OH), fluorosulfonyl group, SR$^a$, N(R$^a$)$_2$, B(R$^a$)$_2$, Si(R$^a$)$_3$, or —C≡C—Si(R$^a$)$_3$ (wherein R$^a$ represents an optionally substituted alkyl group, an optionally substituted aryl group, or an optionally substituted heteroaryl group; or two R$^a$s, together with an atom bound thereto, may form a bicyclic group or a tricyclic group optionally having a heteroatom); provided that the alkyl group, the alkenyl group, the alkynyl group, and the alkoxy group are each optionally substituted with 1 to 3 atoms or groups, selected from the group consisting of halogen atom, hydroxy group, $C_{1-20}$ alkoxy group, aryloxy group, amino group, carbazole group, N(R$^a$)$_2$ (wherein R$^a$ is as defined above), trifluoromethyl group, $C_{2-12}$ perfluoroalkyl group, $C_{3-8}$ cycloalkyl group, aryl group, and heteroaryl group; and the aryl group, aryl moiety, heteroaryl group, heteroaryl moiety, and carbazole group are each optionally substituted with 1 to 5 atoms or groups, selected from the group consisting of halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, cyano group, nitro group, amino group, carbazole group, monoalkylamino group, monoarylamino group, monoheteroarylamino group, N(R$^a$)$_2$ (wherein R$^a$ is as defined above), carbamoyl group, mono- or di-alkylcarbamoyl group, sulfamoyl group, mono- or di-alkylsulfamoyl group, $C_{1-20}$ alkylcarbonyl group, $C_{1-20}$ alkylsulfonyl group, $C_{1-20}$ alkylsulfonylamino group, $C_{1-20}$ alkylcarbonylamino group, methylenedioxy group, heteroaryl group, and aryl group (wherein the aryl group is optionally substituted with 1 to 5 atoms or groups, selected from the group consisting of halogen atom, $C_{1-20}$ alkyl group, $C_{3-8}$ cycloalkyl group, $C_{2-20}$ alkenyl group, $C_{2-20}$ alkynyl group, hydroxy group, trifluoromethyl group, $C_{2-12}$ perfluoroalkyl group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, methylenedioxy group, cyano group, nitro group, amino group, carbazole group, and N(R$^a$)$_2$ (wherein R$^a$ is as defined above)).

Or, two adjacent Rs, together with carbon atom bound thereto, form a five- or six-membered monocyclic group, bicyclic group, or tricyclic group optionally having a heteroatom; or three adjacent Rs form, together with carbon atom bound thereto, a bicyclic group or a tricyclic group optionally having a heteroatom.

When two adjacent Rs are Rs in adjacent rings, the two Rs form a single bond, CH$_2$, CHR$^a$, CR$^a_2$, NR$^a$, Si(R$^a$)$_2$, BR$^a$ (wherein R$^a$ is as defined above), Se, S, or O.)

Item 7. The polycyclic aromatic compound or a salt thereof according to any one of items 1 to 6 represented by the following general formulae (III') to (XXIII').

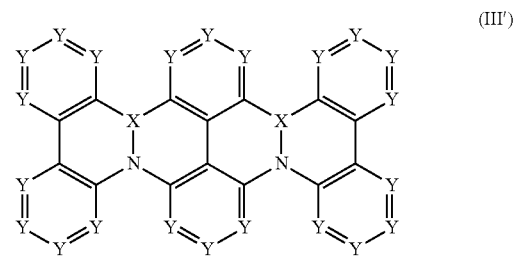

(III')

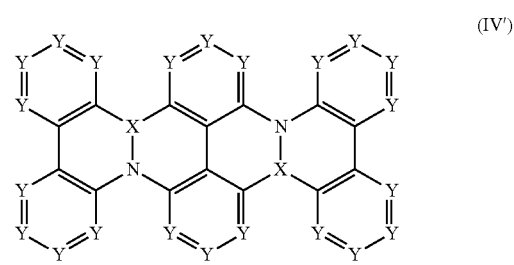

(IV')

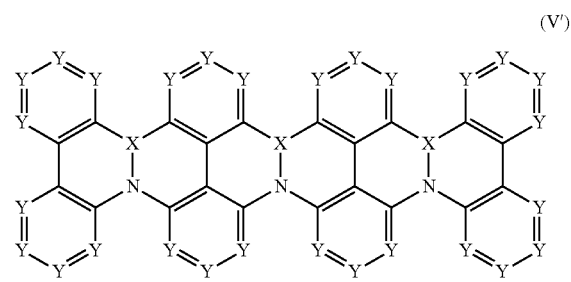

(V')

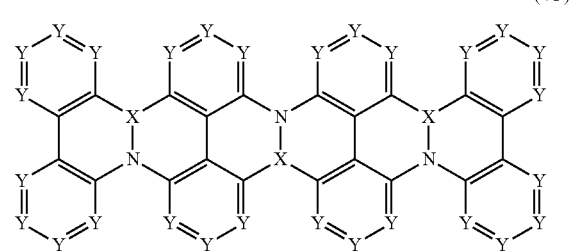

(VI')

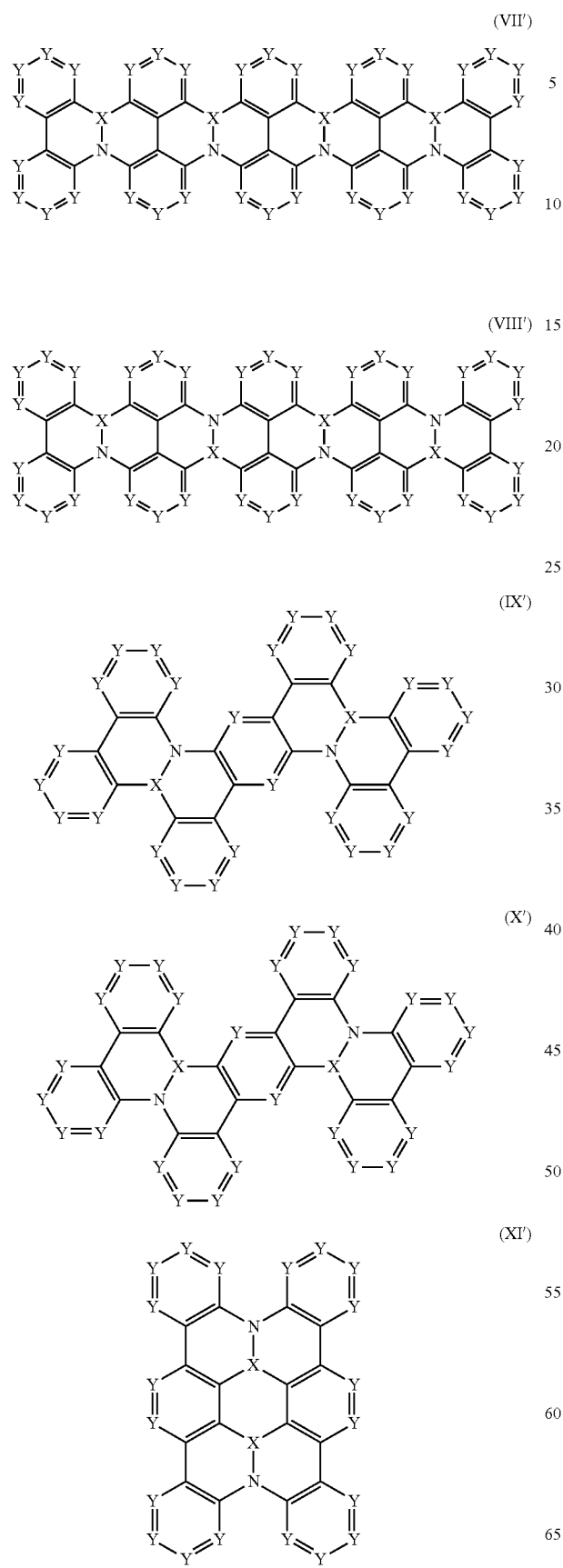
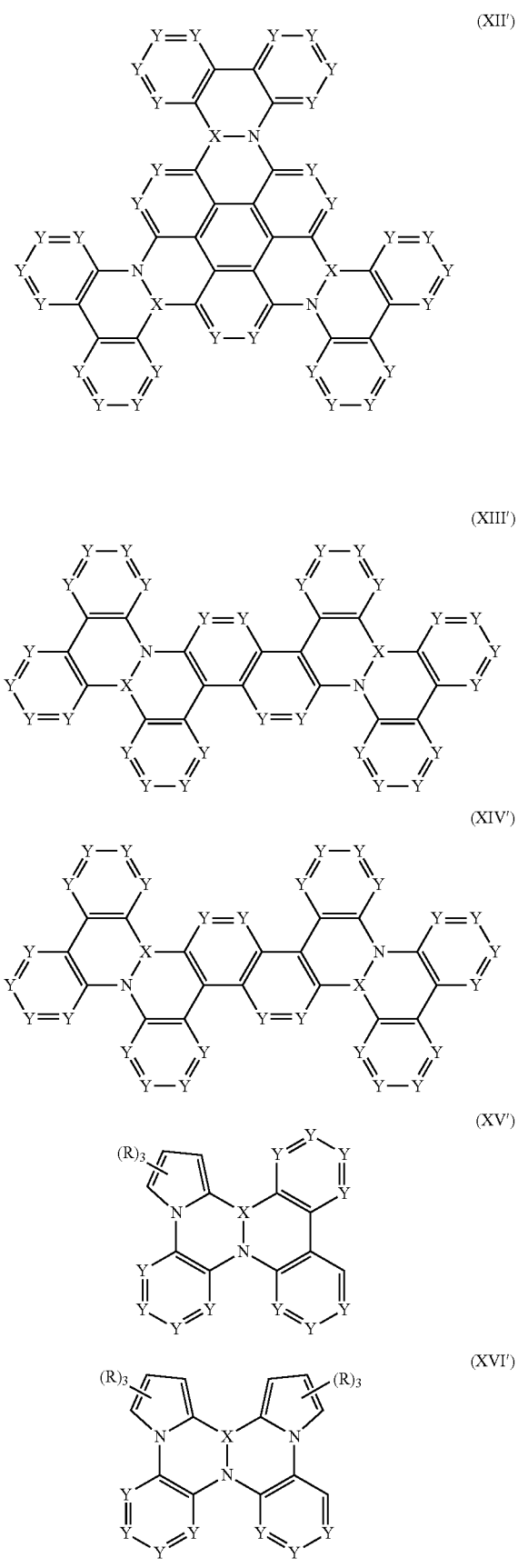

(XVII')
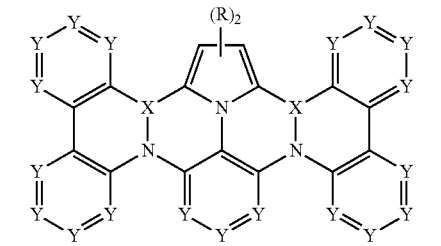

(XVIII')
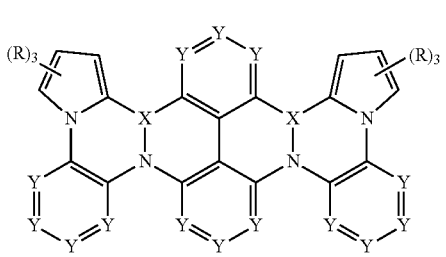

(XIX')
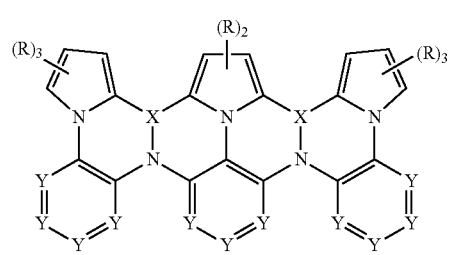

(XX')
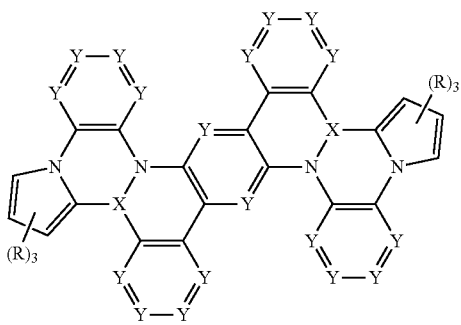

(XXI')
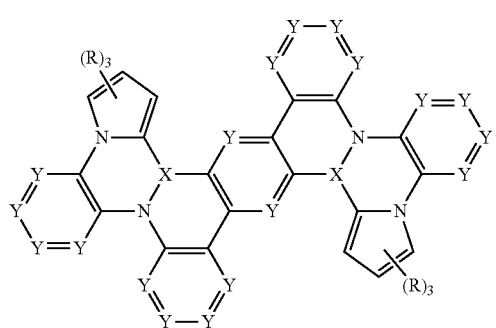

(XXII')
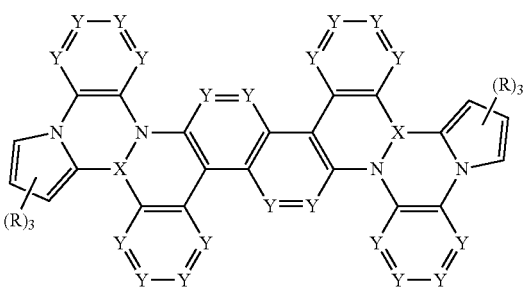

(XXIII')
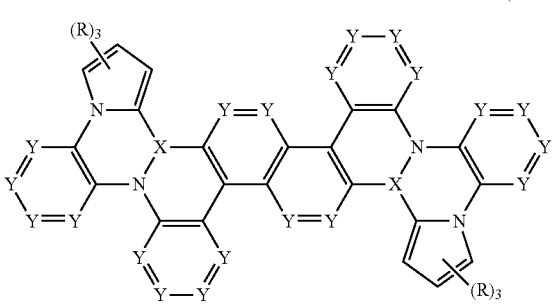

(In the formulae,

Ys are the same or different, and each represents CR or N; or two adjacent Ys on the same ring, together with a bond therebetween, form NR, O, S, or Se.

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.

R represents a hydrogen atom, halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, cyano group, nitro group, amino group, monoalkylamino group, monoarylamino group, monoheteroarylamino group, carbazole group, $C_{1-20}$ alkoxycarbonylamino group, carbamoyl group, mono- or di-alkylcarbamoyl group, sulfamoyl group, mono- or di-alkylsulfamoyl group, $C_{1-20}$ alkylsulfonylamino group, $C_{1-20}$ alkylcarbonylamino group, aryl group, heteroaryl group, $C_{1-20}$ alkoxycarbonyl group, carboxyl group, 5-tetrazolyl group, sulfo group (—SO$_2$OH), fluorosulfonyl group, SR$^a$, N(R$^a$)$_2$, B(R$^a$)$_2$, Si(R$^a$)$_3$, or —C≡C—Si(R$^a$)$_3$ (wherein R$^a$ represents an optionally substituted alkyl group, an optionally substituted aryl group, or an optionally substituted heteroaryl group; or two R$^a$s, together with an atom bound thereto, may form a bicyclic group or a tricyclic group optionally having a heteroatom); provided that the alkyl group, the alkenyl group, the alkynyl group, and the alkoxy group are each optionally substituted with 1 to 3 atoms or groups, selected from the group consisting of halogen atom, hydroxy group, $C_{1-20}$ alkoxy group, aryloxy group, amino group, carbazole group, N(R$^a$)$_2$ (wherein R$^a$ is as defined above), trifluoromethyl group, $C_{2-12}$ perfluoroalkyl group, $C_{3-8}$ cycloalkyl group, aryl group, and heteroaryl group; and the aryl group, aryl moiety, heteroaryl group, heteroaryl moiety, and carbazole group are each optionally substituted with 1 to 5 atoms or groups, selected from the group consisting of halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, cyano group, nitro group, amino group, carbazole group, monoalkylamino group, monoarylamino group, monoheteroarylamino group, $N(R^a)_2$ (wherein $R^a$ is as defined above), carbamoyl group, mono- or di-alkylcarbamoyl group, sulfamoyl group, mono- or di-alkylsulfamoyl group, $C_{1-20}$ alkylcarbonyl group, $C_{1-20}$ alkylsulfonyl group, $C_{1-20}$ alkylsulfonylamino group, $C_{1-20}$ alkylcarbonylamino group, methylenedioxy group, heteroaryl group, and aryl group (wherein the aryl group is optionally substituted with 1 to 5 atoms or groups, selected from the group consisting of halogen atom, $C_{1-20}$ alkyl group, $C_{3-8}$ cycloalkyl group, $C_{2-20}$ alkenyl group, $C_{2-20}$ alkynyl group, hydroxy group, trifluoromethyl group, $C_{2-12}$ perfluoroalkyl group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, methylenedioxy group, cyano group, nitro group, amino group, carbazole group, and $N(R^a)_2$ (wherein $R^a$ is as defined above)).

Or, two adjacent Rs, together with carbon atom bound thereto, form a five- or six-membered monocyclic group, bicyclic group, or tricyclic group optionally having a heteroatom; or three adjacent Rs form, together with carbon atom bound thereto, a bicyclic group or a tricyclic group optionally having a heteroatom.

When two adjacent Rs are Rs in adjacent rings, the two Rs form a single bond, $CH_2$, $CHR^a$, $CR^a_2$, $NR^a$, $Si(R^a)_2$, $BR^a$ (wherein $R^a$ is as defined above), Se, S, or O.)

Item 8. The compound according to any one of items 1 to 7 represented by any one of the following formulae (II'-1A) to (XIV'-1A).

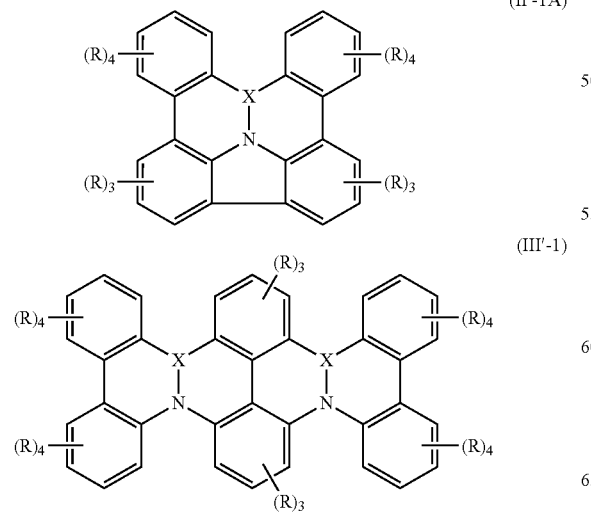

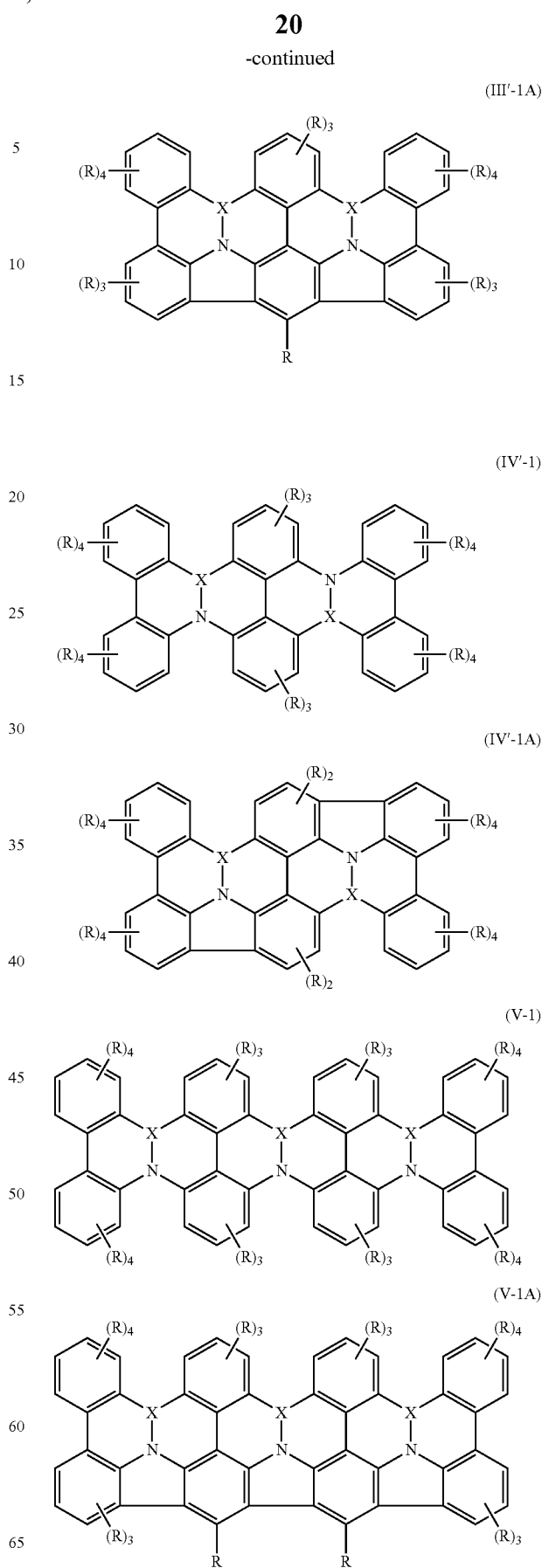

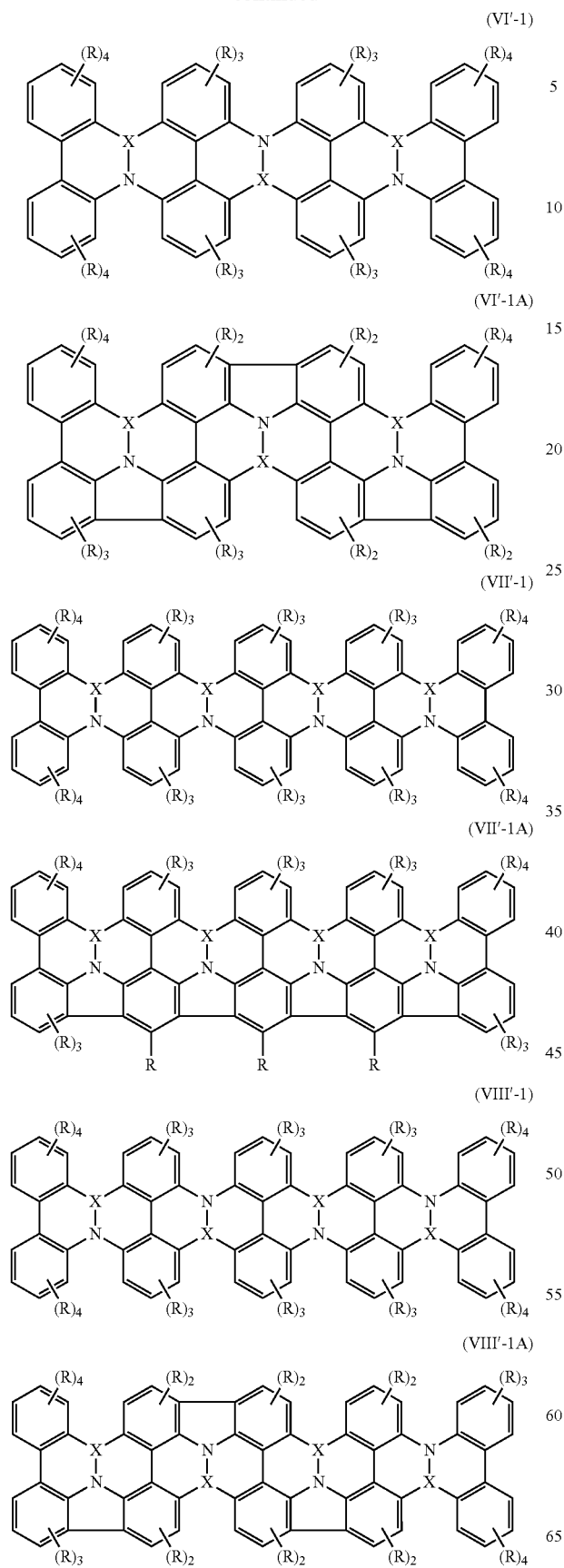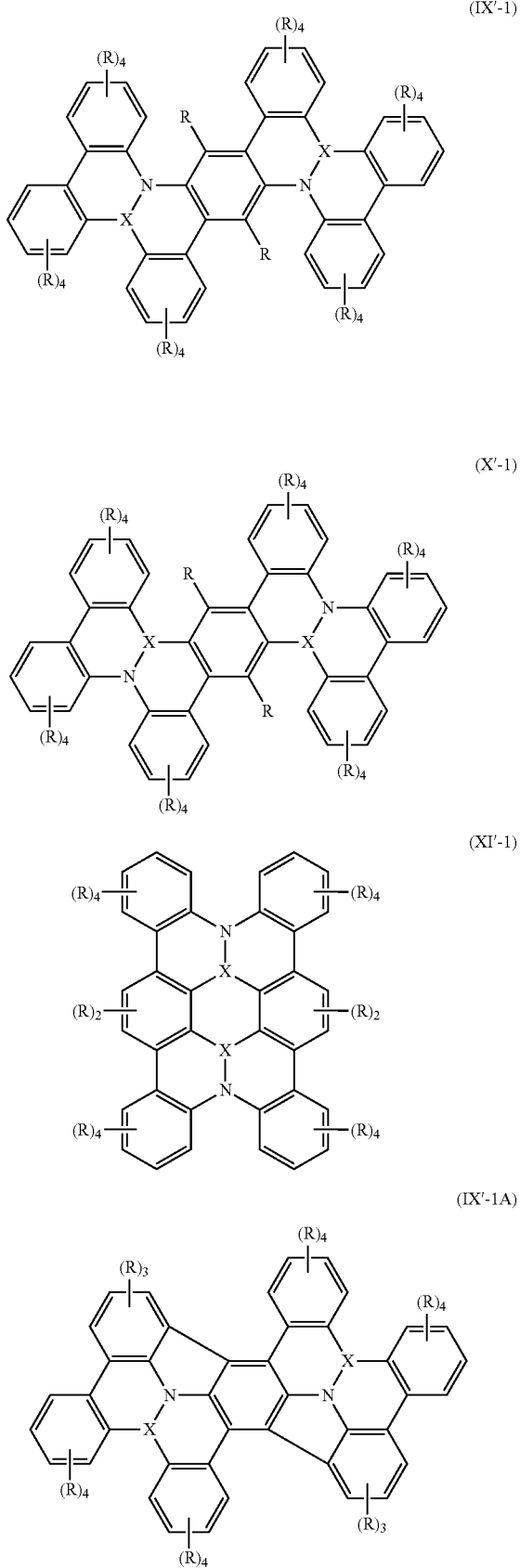

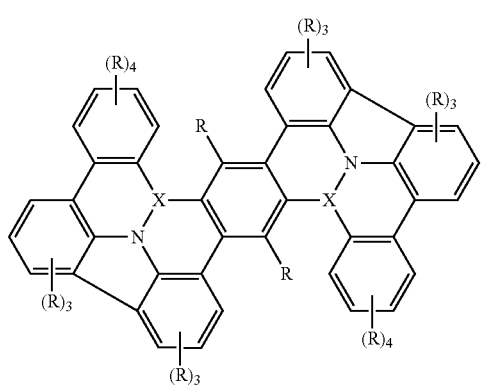
(X′-1A)
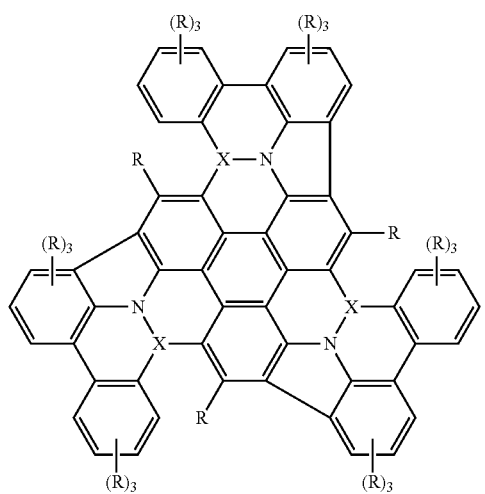
(XII′-1A)
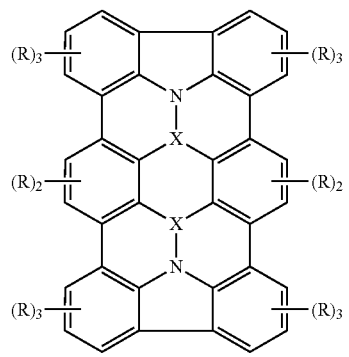
(XI′-1A)
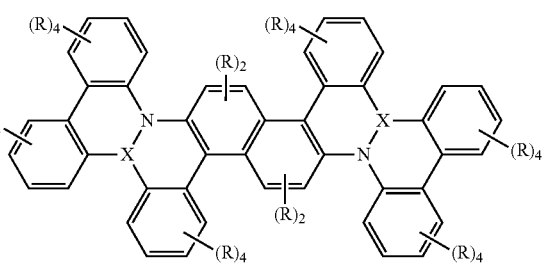
(XIII′-1)
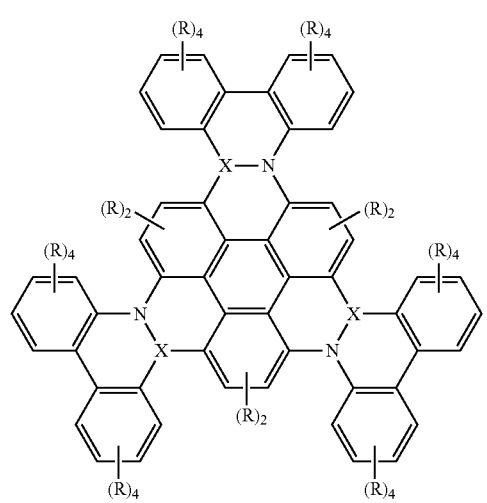
(XII′-1)
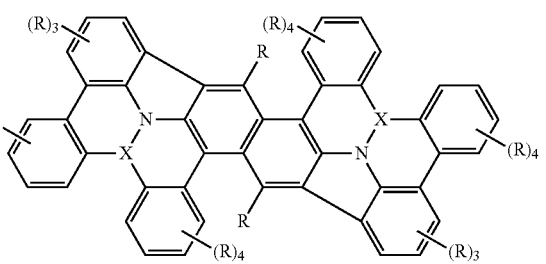
(XIII′-1A)
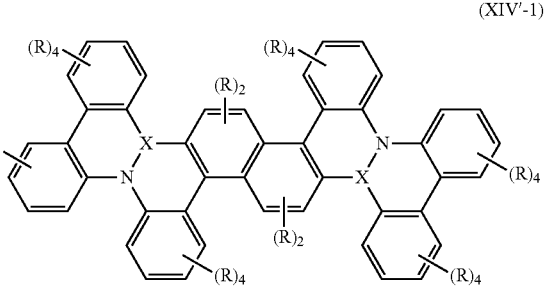
(XIV′-1)

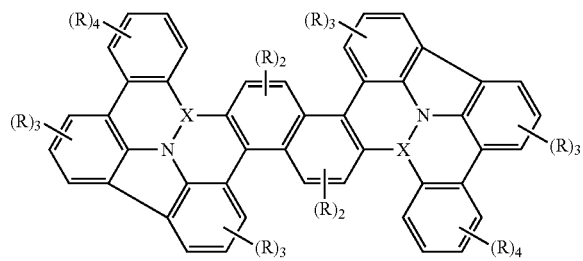

(XIV'-1A)

(In the formulae,
X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.

R represents a hydrogen atom, halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{2-20}$ alkoxy group, aryloxy group, trifluoromethoxy group, trifluoroethoxy group, $C_{2-12}$ perfluoroalkoxy group, $C_{1-20}$ alkylcarbonyl group, $C_{2-20}$ alkylsulfonyl group, cyano group, nitro group, amino group, monoalkylamino group, monoarylamino group, monoheteroarylamino group, carbazole group, $C_{1-20}$ alkoxycarbonylamino group, carbamoyl group, mono- or di-alkylcarbamoyl group, sulfamoyl group, mono- or di-alkylsulfamoyl group, $C_{1-20}$ alkylsulfonylamino group, $C_{1-20}$ alkylcarbonylamino group, aryl group, heteroaryl group, $C_{1-20}$ alkoxycarbonyl group, carboxyl group, 5-tetrazolyl group, sulfo group (—SO$_2$OH), fluorosulfonyl group, SR$^a$, N(R$^a$)$_2$, B(R$^a$)$_2$, Si(R$^a$)$_3$, or —C≡C—Si(R$^a$)$_3$
(wherein R$^a$ represents an optionally substituted alkyl group, an optionally substituted aryl group, or an optionally substituted heteroaryl group; or two R$^a$s, together with an atom bound thereto, may form a bicyclic group or a tricyclic group optionally having a heteroatom);
Provided that the alkyl group, the alkenyl group, the alkynyl group, and the alkoxy group are each optionally substituted with 1 to 3 atoms or groups, selected from the group consisting of halogen atom, hydroxy group, $C_{1-20}$ alkoxy group, aryloxy group, amino group, carbazole group, N(R$^a$)$_2$ (wherein R$^a$ is as defined above), trifluoromethyl group, $C_{2-12}$ perfluoroalkyl group, $C_{3-8}$ cycloalkyl group, aryl group, and heteroaryl group; and the aryl group, aryl moiety, heteroaryl group, heteroaryl moiety, and carbazole group are each optionally substituted with 1 to 5 atoms or groups, selected from the group consisting of halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, cyano group, nitro group, amino group, carbazole group, monoalkylamino group, monoarylamino group, monoheteroarylamino group, N(R$^a$)$_2$ (wherein R$^a$ is as defined above), carbamoyl group, mono- or di-alkylcarbamoyl group, sulfamoyl group, mono- or di-alkylsulfamoyl group, $C_{1-20}$ alkylcarbonyl group, $C_{1-20}$ alkylsulfonyl group, $C_{1-20}$ alkylsulfonylamino group, $C_{1-20}$ alkylcarbonylamino group, methylenedioxy group, heteroaryl group, and aryl group (wherein the aryl group is optionally substituted with 1 to 5 atoms or groups, selected from the group consisting of halogen atom, $C_{1-20}$ alkyl group, $C_{3-8}$ cycloalkyl group, $C_{2-20}$ alkenyl group, $C_{2-20}$ alkynyl group, hydroxy group, trifluoromethyl group, $C_{2-12}$ perfluoroalkyl group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, methylenedioxy group, cyano group, nitro group, amino group, carbazole group, and N(R$^a$)$_2$ (wherein R$^a$ is as defined above)).

Or, two adjacent Rs, together with carbon atom bound thereto, form a five- or six-membered monocyclic group, bicyclic group, or tricyclic group optionally having a heteroatom; or three adjacent Rs form, together with a carbon atom bound thereto, a bicyclic group or a tricyclic group optionally having a heteroatom.

When two adjacent Rs are Rs in adjacent rings, the two Rs form a single bond, CH$_2$, CHR$^a$, CR$^a{}_2$, NR$^a$, Si(R$^a$)$_2$, BR$^a$ (wherein R$^a$ is as defined above), Se, S, or O.)

Item 9. An electrochemical device containing the compound according to any one of items 1 to 8.

Item 10. The electrochemical device according to item 9, wherein the device is an organic light-emitting element, an organic thin-film transistor, or an organic thin-film solar cell.

Advantageous Effects of Invention

The present invention can provide a new compound for electron transporting materials, luminescent materials, positive hole transporting materials, and the like, suitable to be used in organic thin-film solar cells, organic thin-film transistors, and organic light-emitting elements such as organic EL devices and organic light-emitting diodes. Zone Name: d1,AMD

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is the x-ray crystal structure of 4b-aza-12b-phenyl-12b-siladibenzo[g,p]chrysene of Example 2.

FIG. 2 is the x-ray crystal structure of 4b-aza-12b-germa-12b-phenyldibenzo[g,p]chrysene of Example 3.

DESCRIPTION OF EMBODIMENTS

In the present specification, Y$^a$s are the same or different, and each represents C— or N; or two adjacent Y$^a$s on the same ring, together with a bond therebetween, form N—, O, S, or Se. Furthermore, Ys are the same or different, and form C—R or N; or two adjacent Ys on the same ring, together with a bond therebetween, form NR, O, S, or Se. Although Y and Y$^a$ are groups corresponding to each other, Y$^a$ is used in a partial structure, and does not include an R group.

The present invention provides a polycyclic aromatic compound or a salt thereof having a partial structure represented by the following general formula (I).

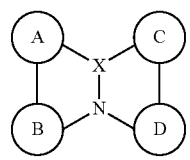
(I)

(In the formula, X, ring A, ring B, ring C, and ring D are as defined above.)

One preferable embodiment of the present invention is the polycyclic aromatic compound or a salt thereof having a partial structure represented by the following general formula (II).

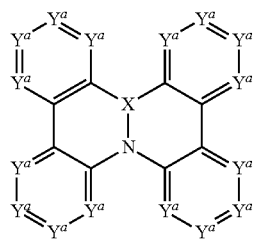
(II)

(In the formula, X and $Y^a$ are as defined above.)

One preferable embodiment of the present invention is the polycyclic aromatic compound or a salt thereof having a partial structure represented by the following general formula (II-1).

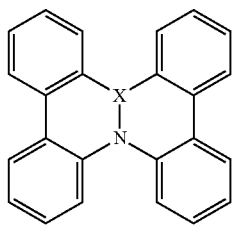
(II-1)

(In the formula, X is as defined above.)

Another preferable embodiment of the present invention is the polycyclic aromatic compound or a salt thereof having a partial structure represented by any one of the following general formulae (II-2) to (II-54).

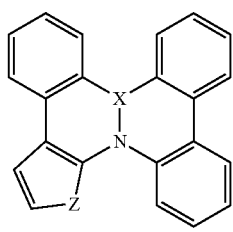
(II-2)

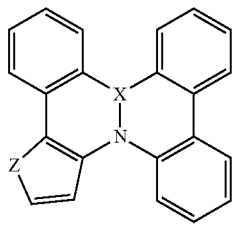
(II-3)

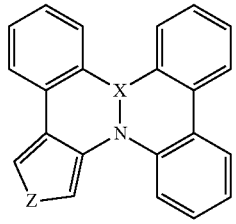
(II-4)

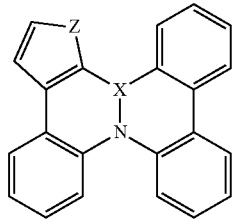
(II-5)

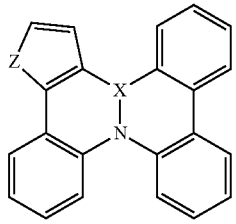
(II-6)

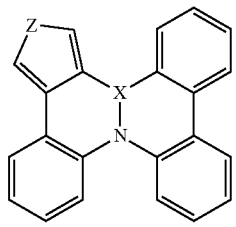
(II-7)

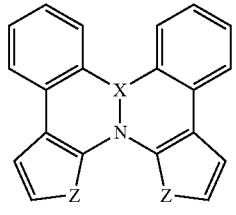
(II-8)

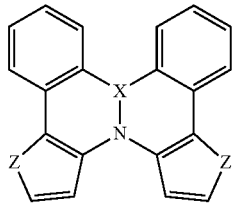
(II-9)

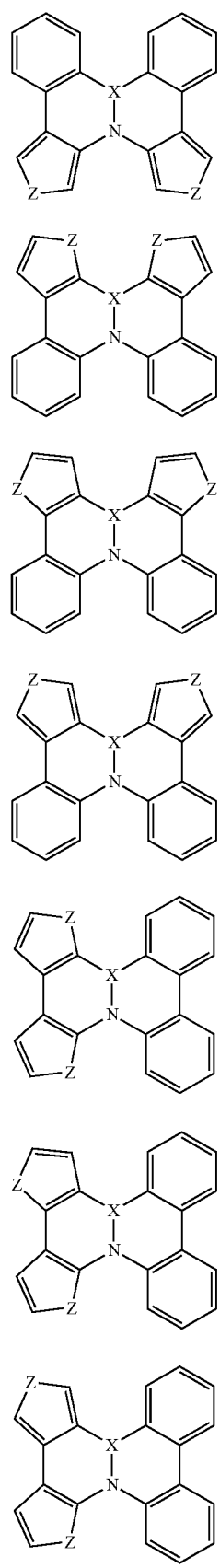
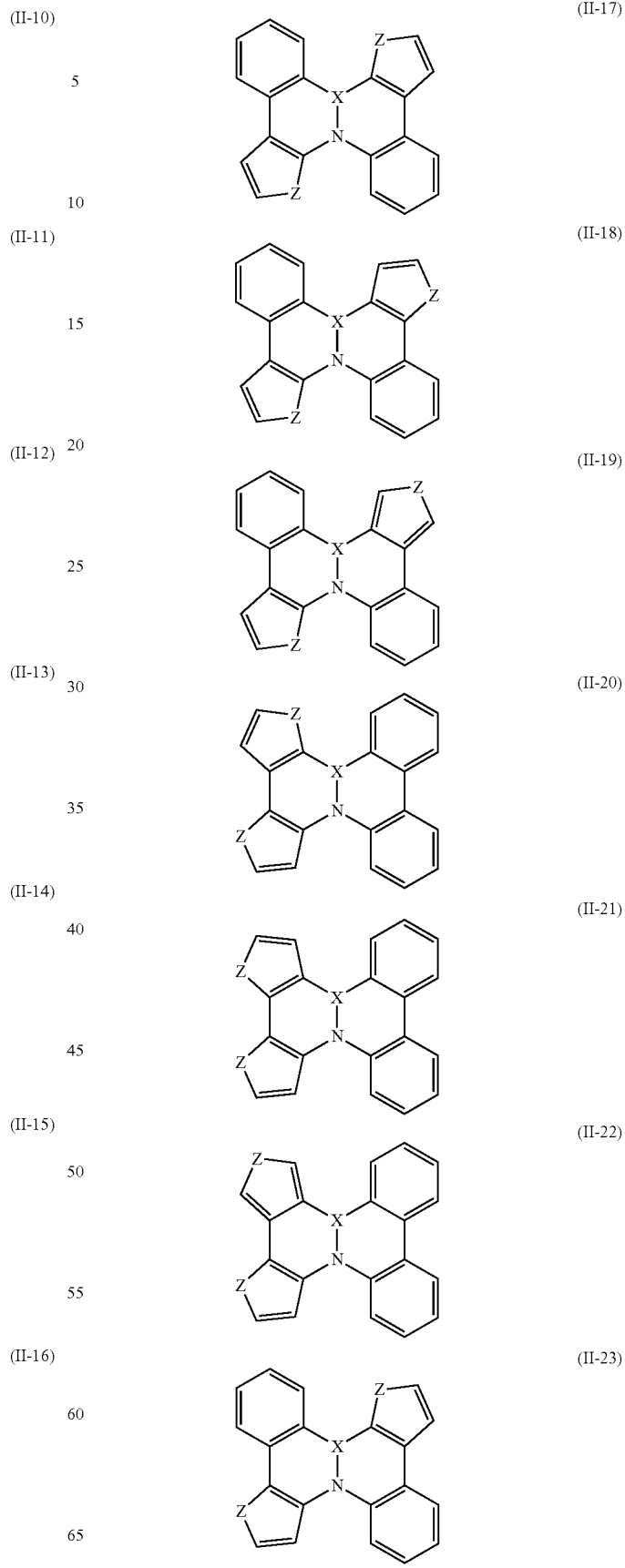

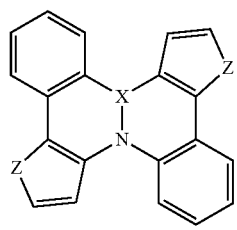
(II-24)
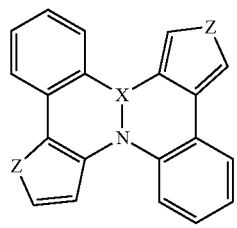
(II-25)
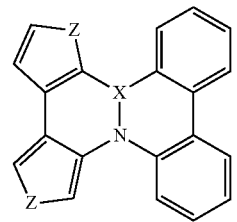
(II-26)
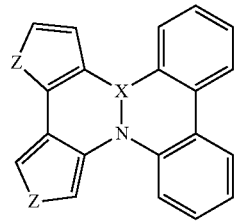
(II-27)
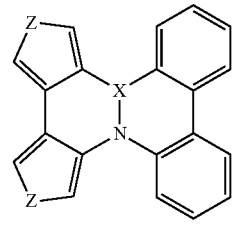
(II-28)
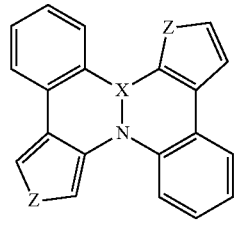
(II-29)
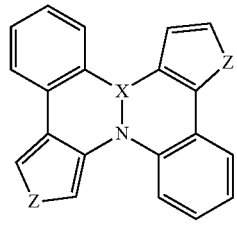
(II-30)
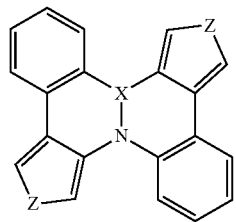
(II-31)
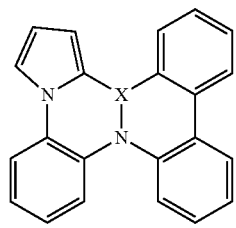
(II-32)
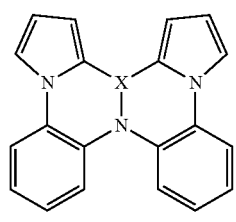
(II-33)
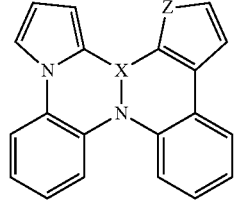
(II-34)
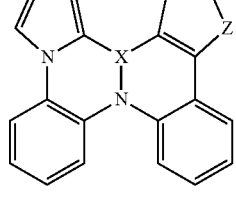
(II-35)
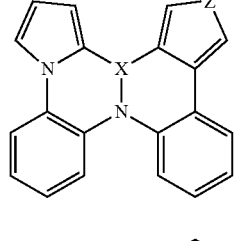
(II-36)
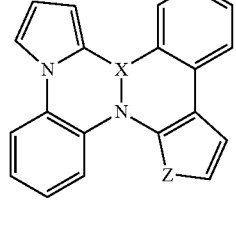
(II-37)

-continued
(II-38)
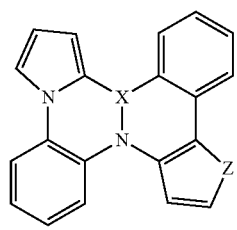
(II-39)
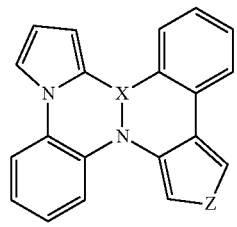
(II-40)
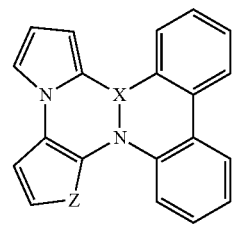
(II-41)
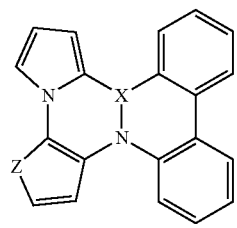
(II-42)
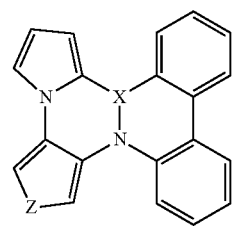
(II-43)
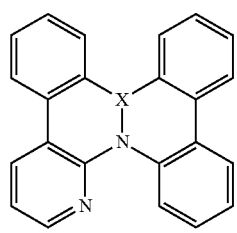
(II-44)
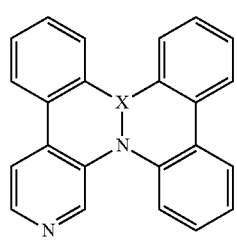
-continued
(II-45)
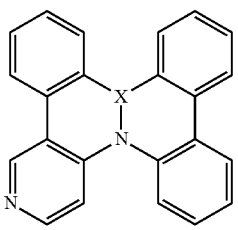
(II-46)
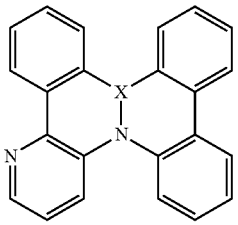
(II-47)
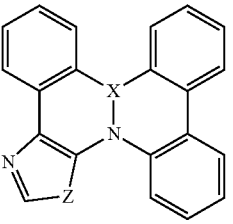
(II-48)
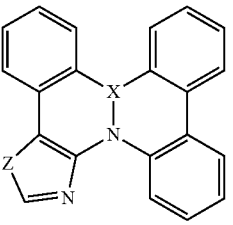
(II-49)
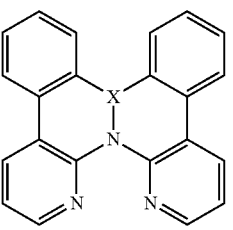
(II-50)
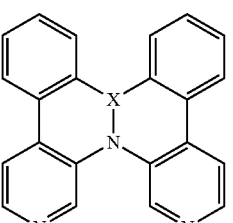
(II-51)
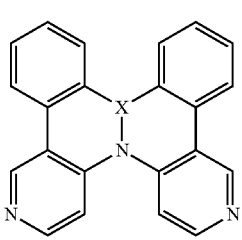

(II-52)
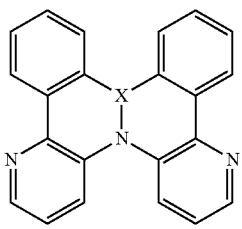
(II-53)
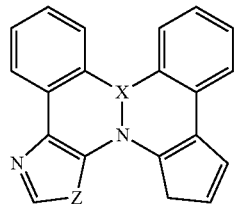
(II-54)
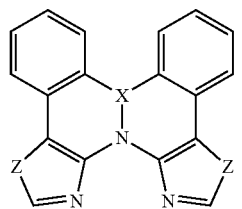
(In the formulae, X and Z are as defined above.)
Examples of the compound having the partial structure represented by general formula (I) include compounds having a skeleton of the following 1 to 149 (these compounds are further optionally substituted).
1
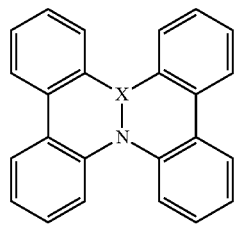
2
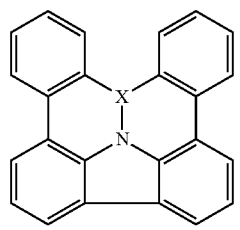
3
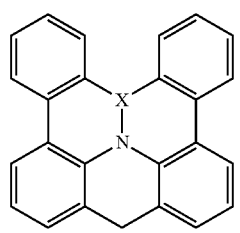
4
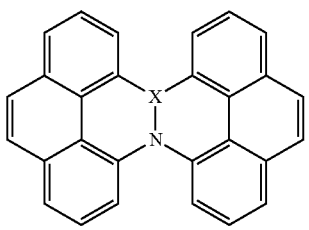
5
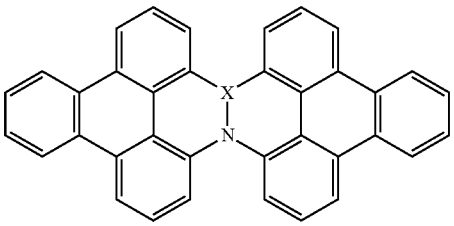
6
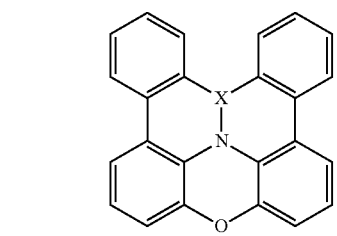
7
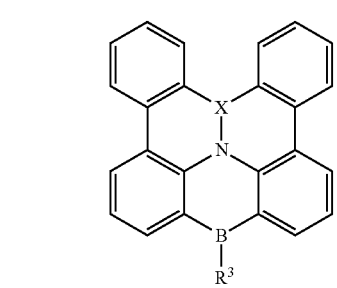
8
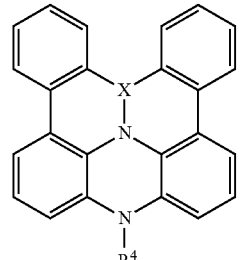
9
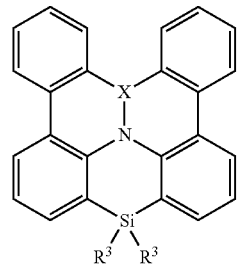

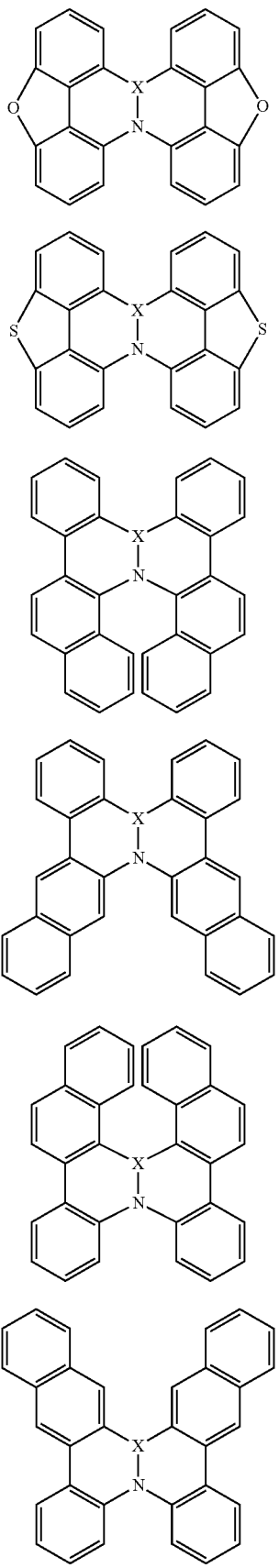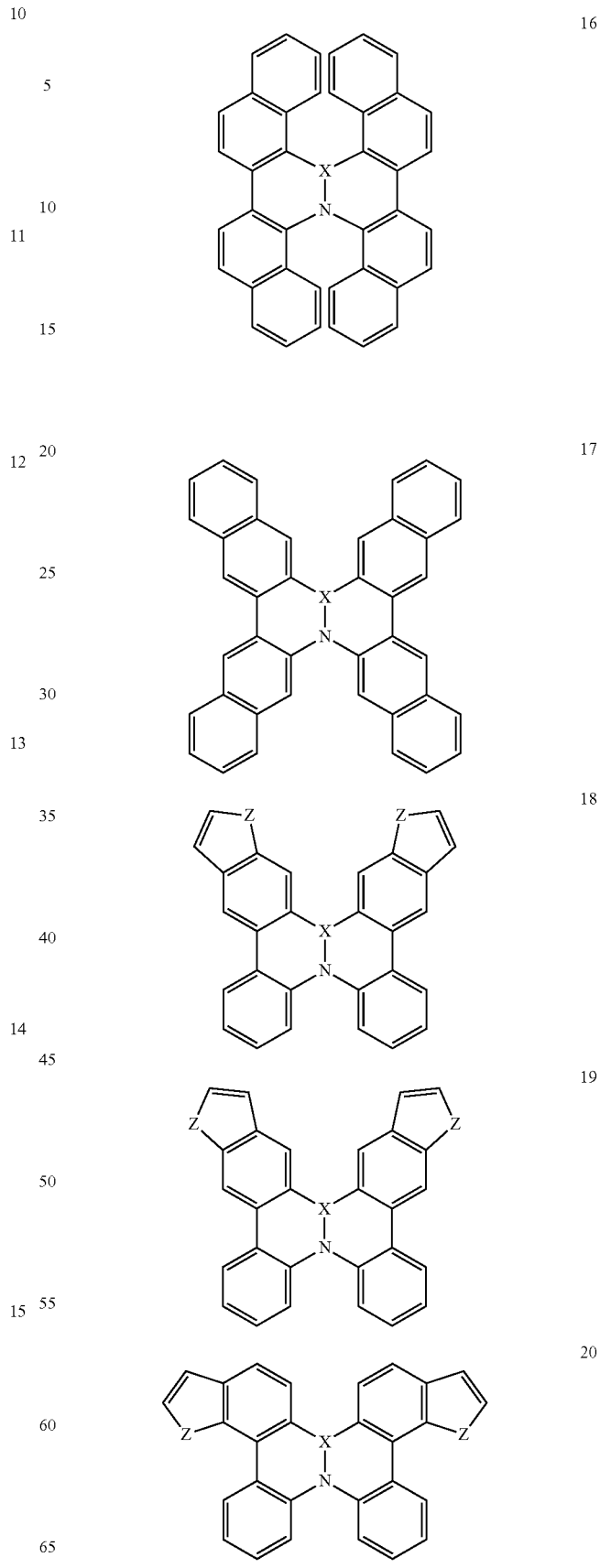

21
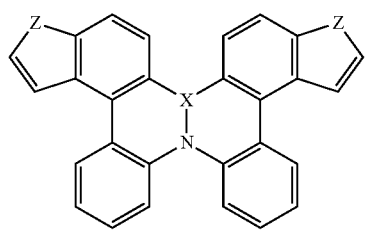
22
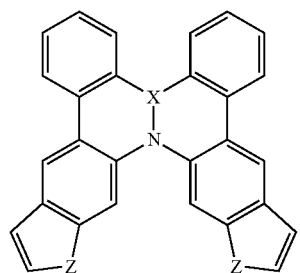
23
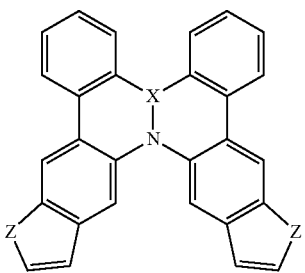
24
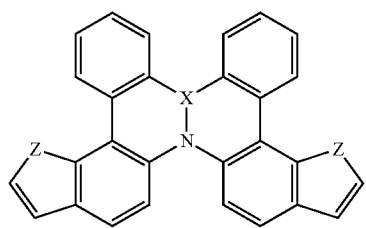
25
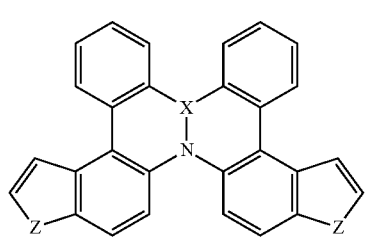
26
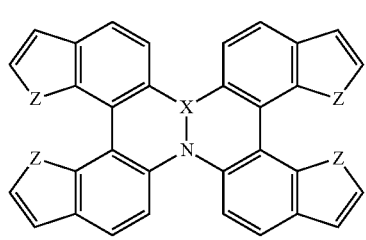
27
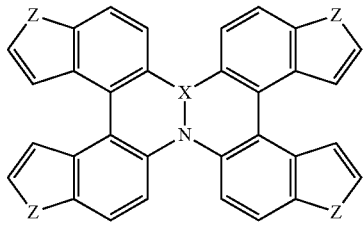
28
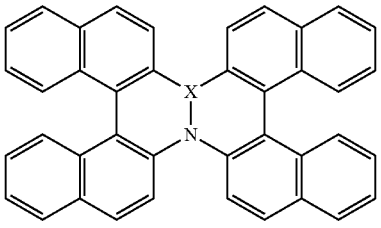
29
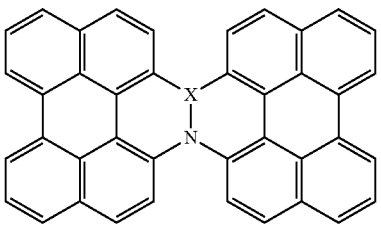
30
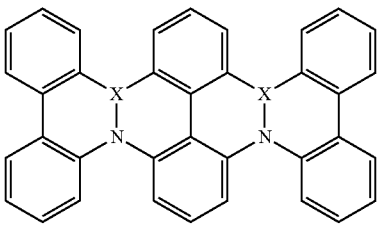
31
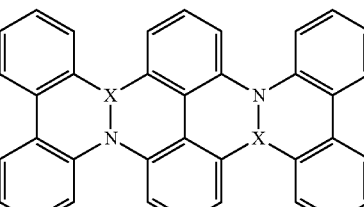
32
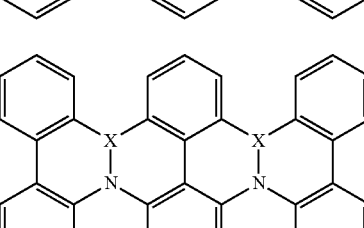
33
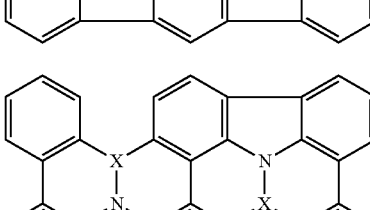

34
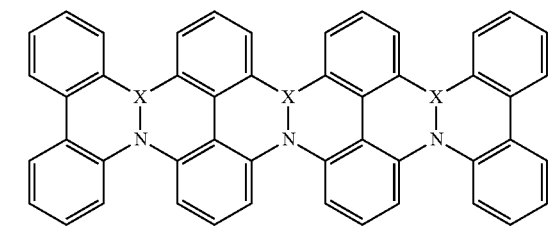
35
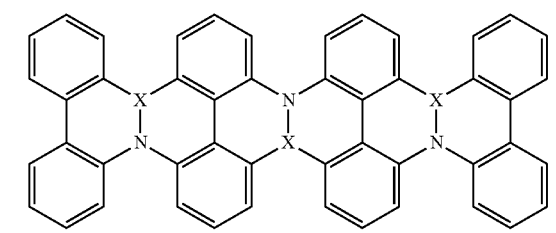
36
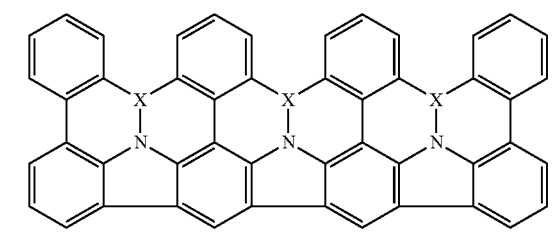
37
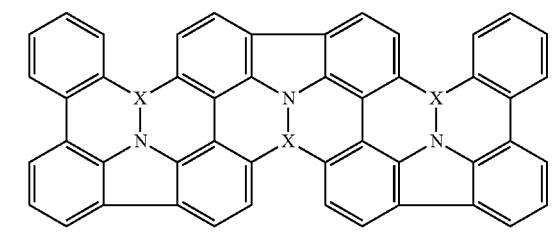
38
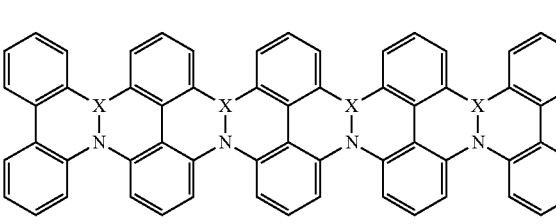
39
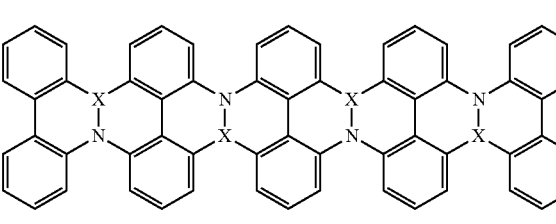
40
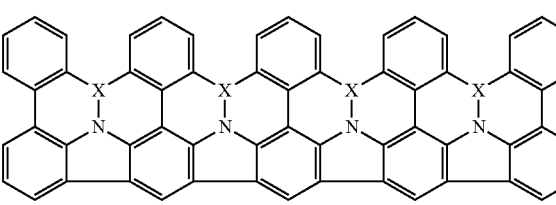
41
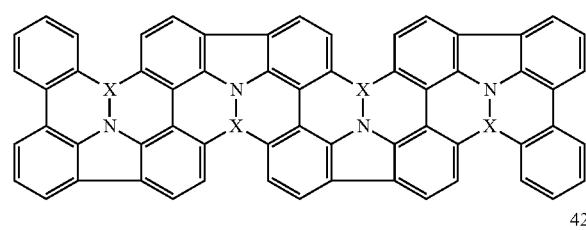
42
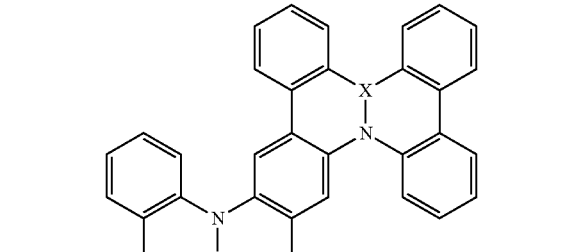
43
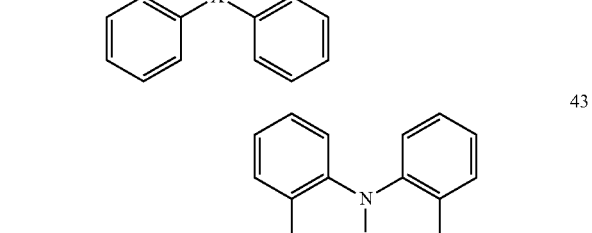
44
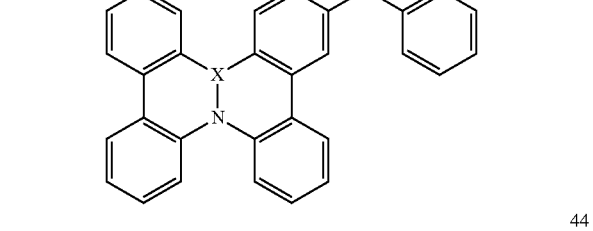
45
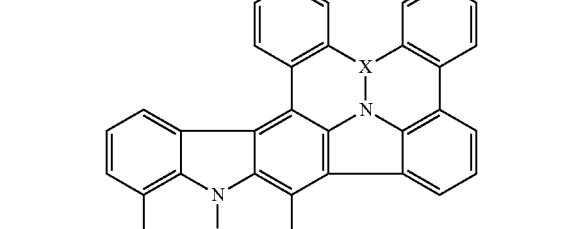

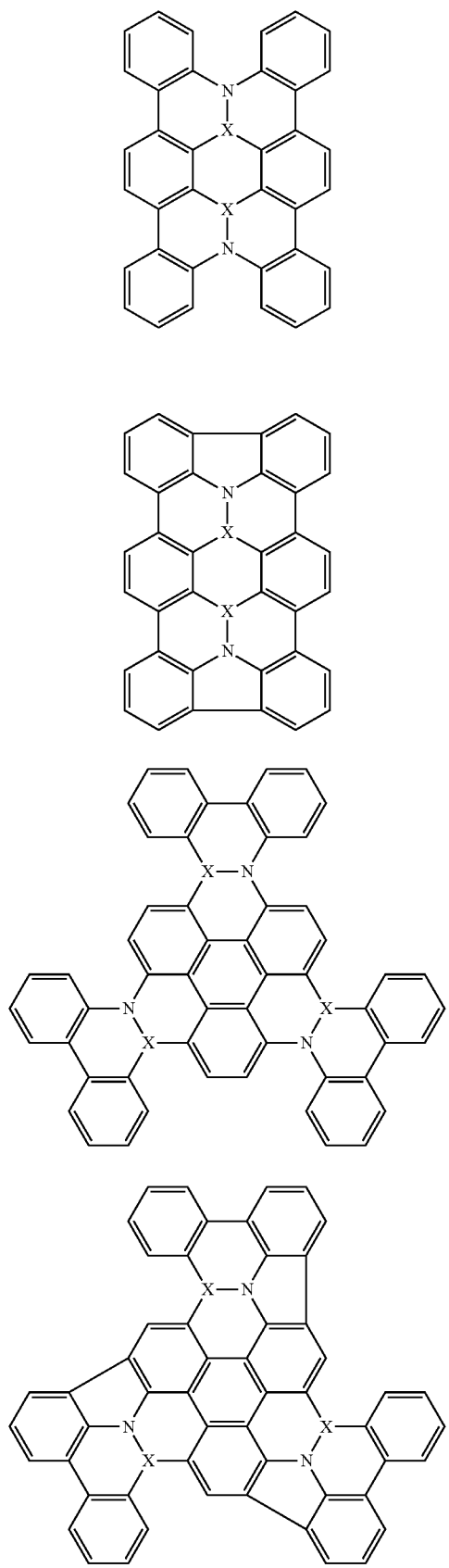
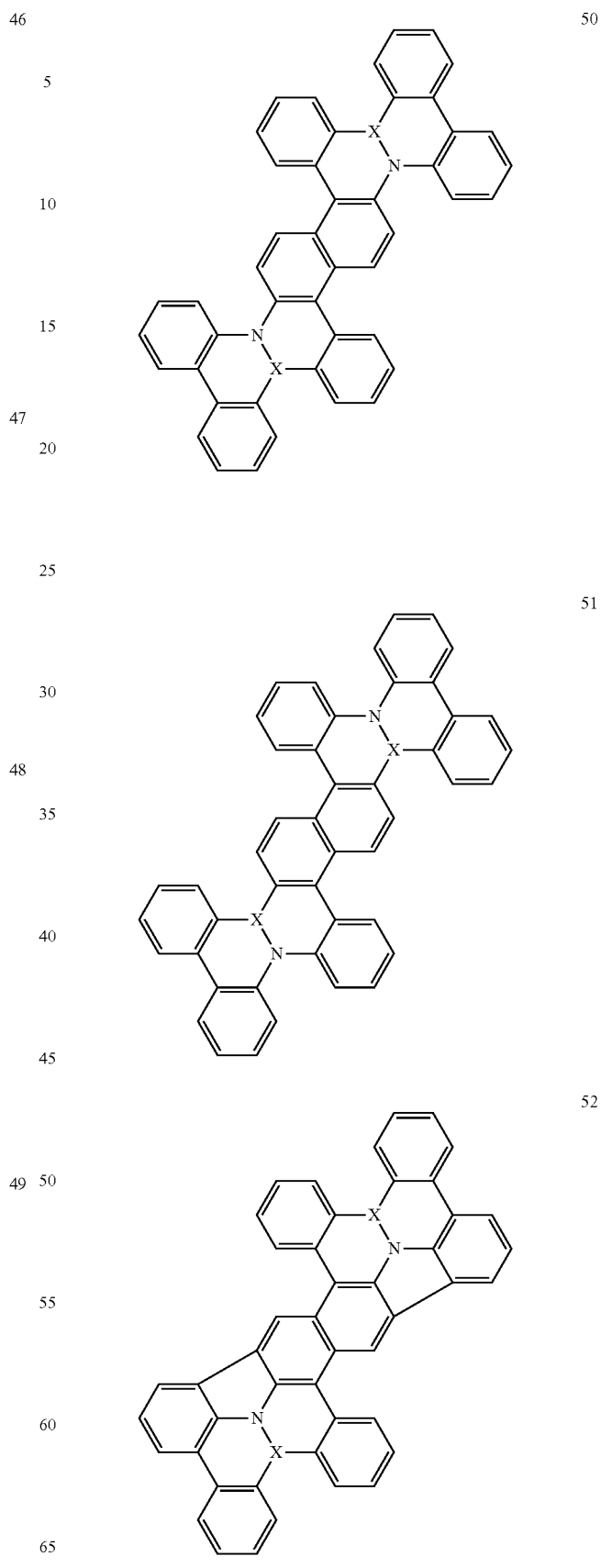

53
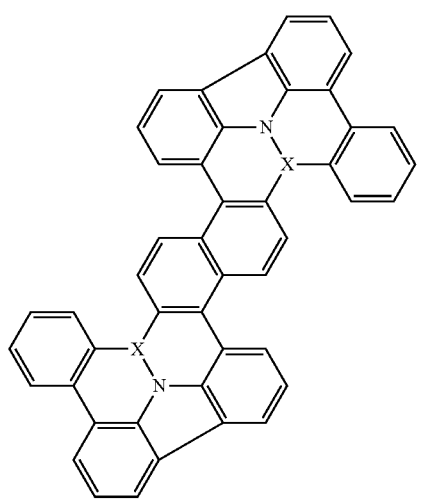
54
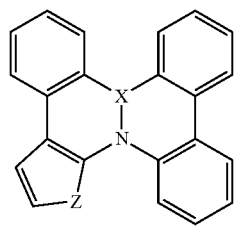
55
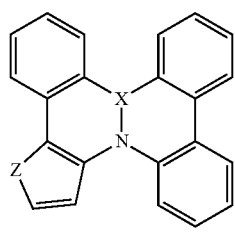
56
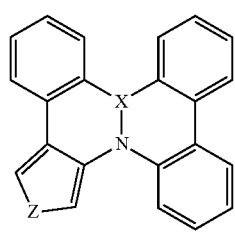
57
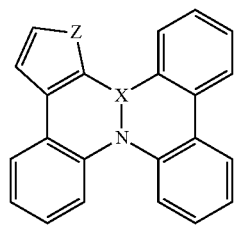
58
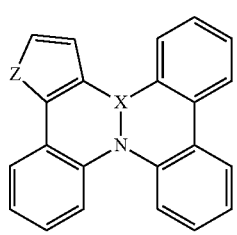
59
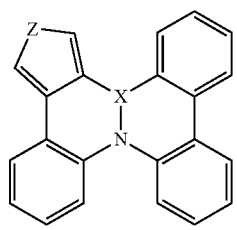
60
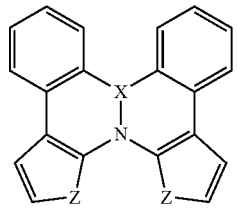
61
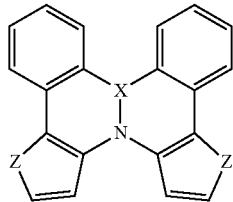
62
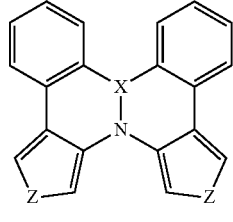
63
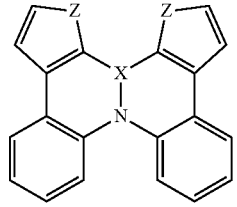
64
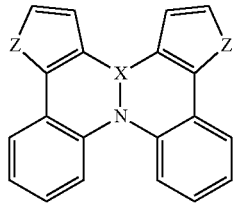

65
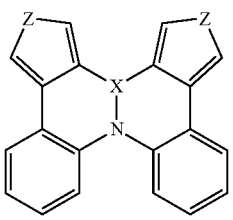
66
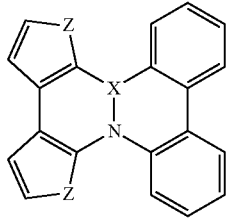
67
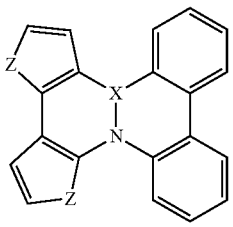
68
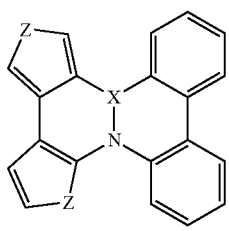
69
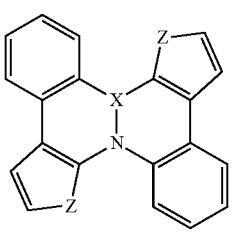
70
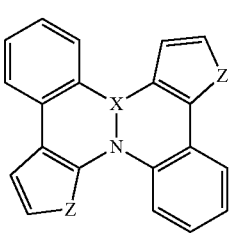
71
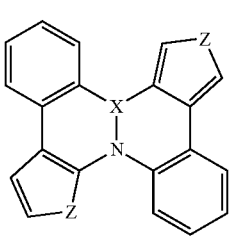
72
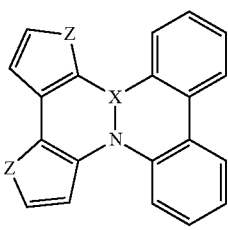
73
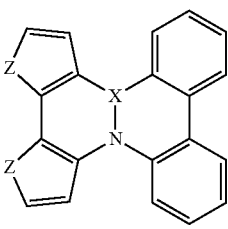
74
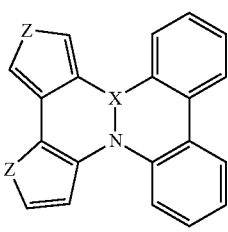
75
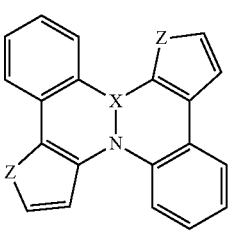
76
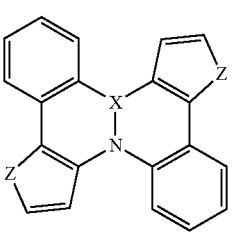
77
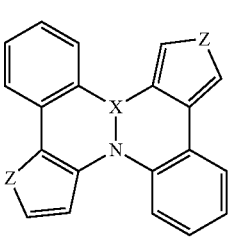
78
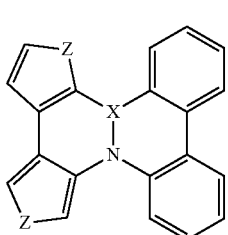

79
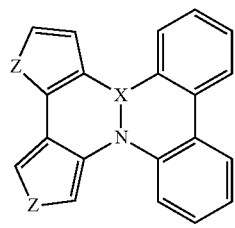
80
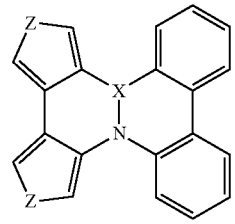
81
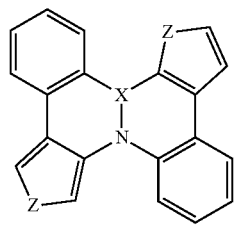
82
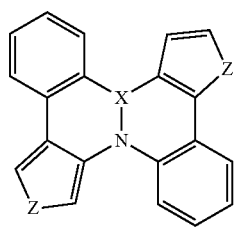
83
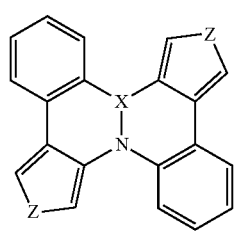
84
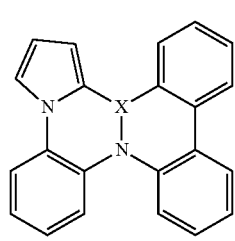
85
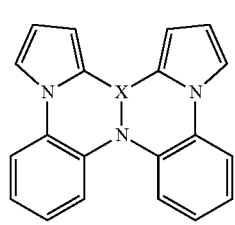
86
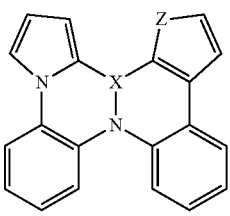
87
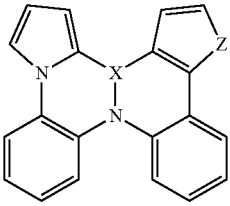
88
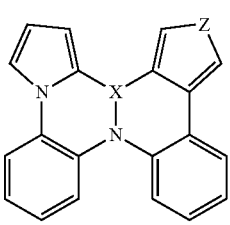
89
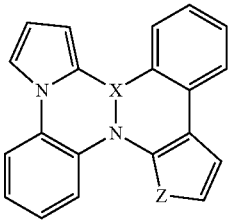
90
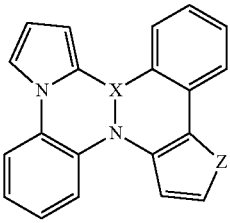
91
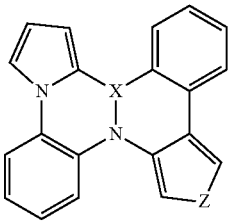
92
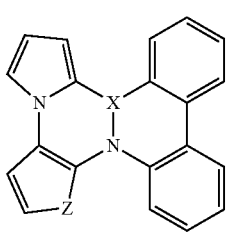

51
-continued
93
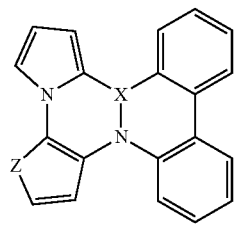
94
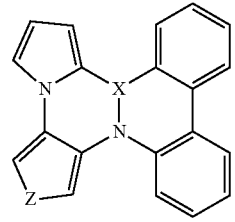
95
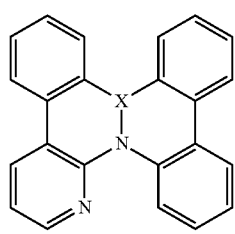
96
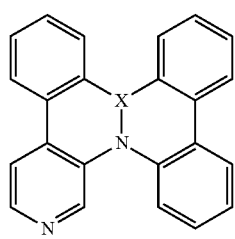
97
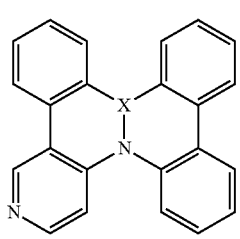
98
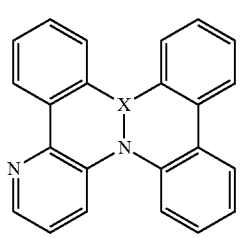
99
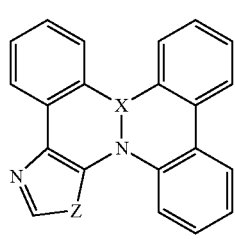
52
-continued
100
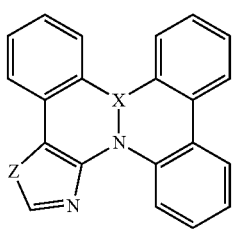
101
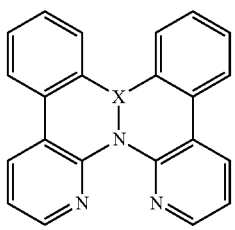
102
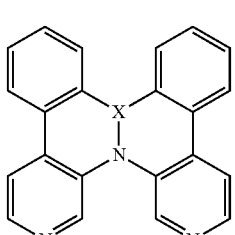
103
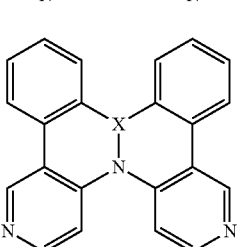
104
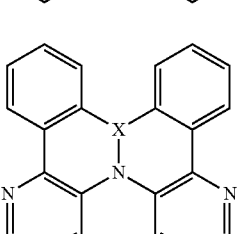
105
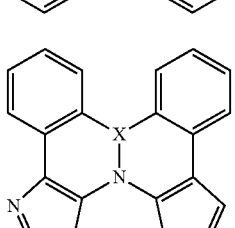
106
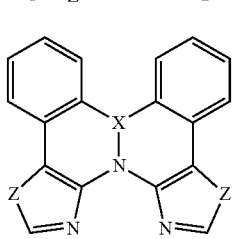

107
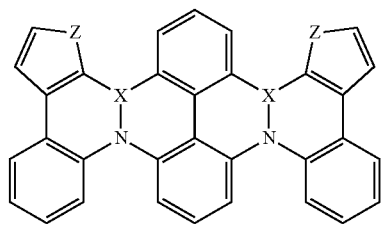
108
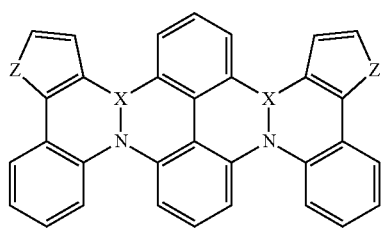
109
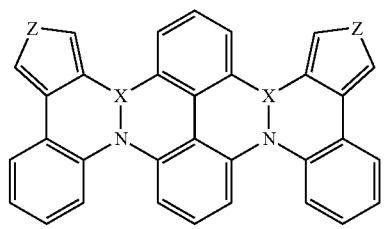
110
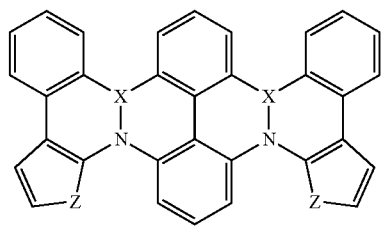
111
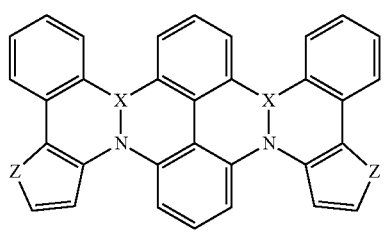
112
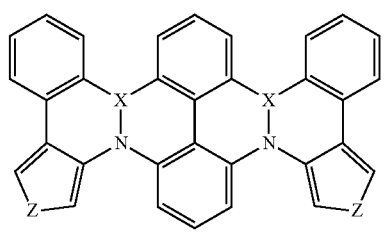
113
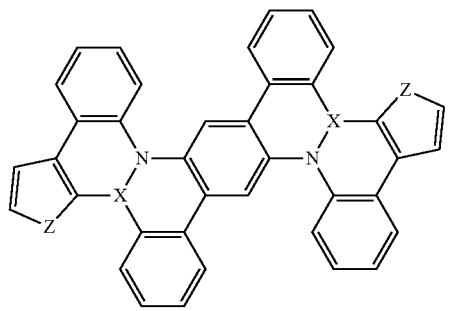
114
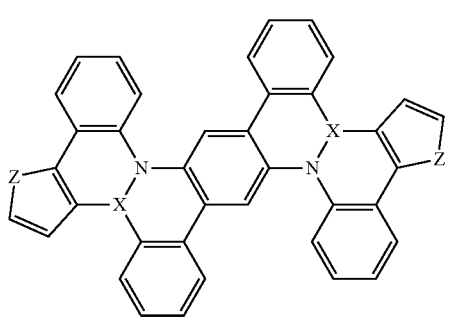
115
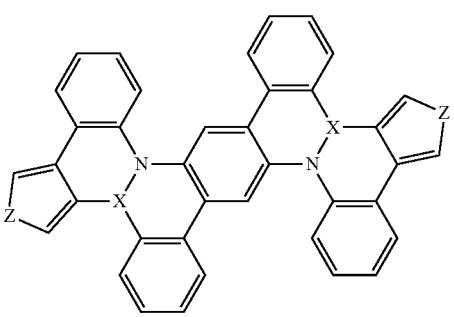
116
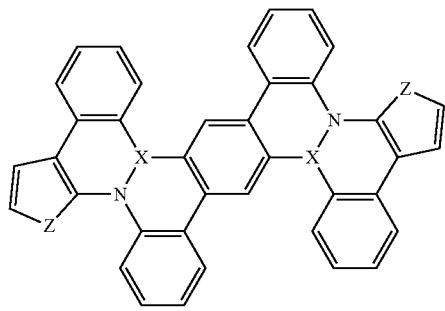
117
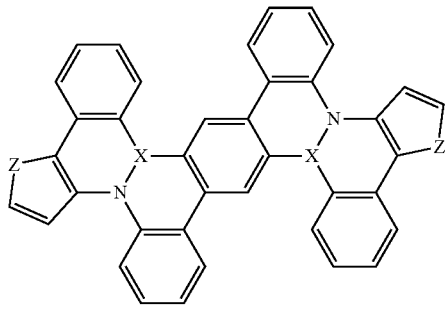

118
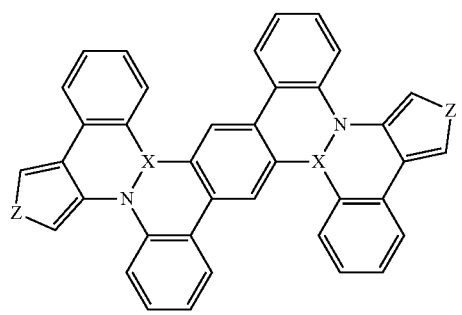
119
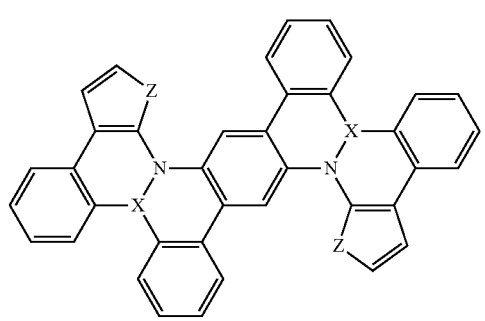
120
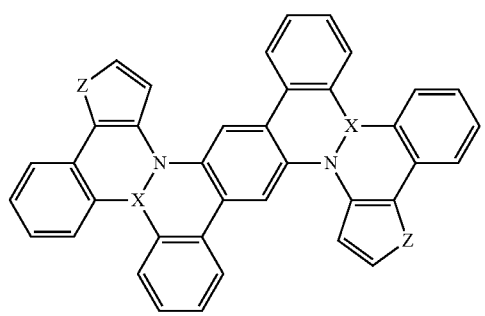
121
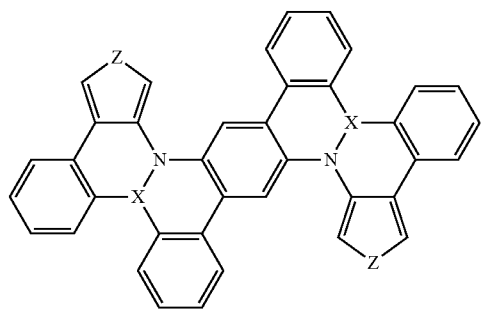
122
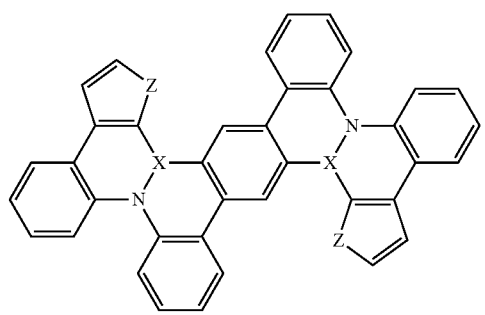
123
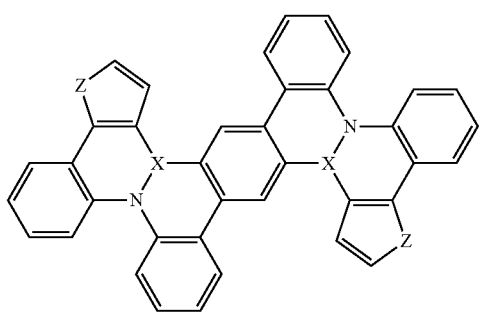
124
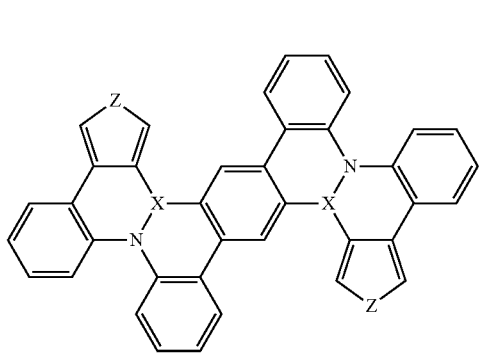
125
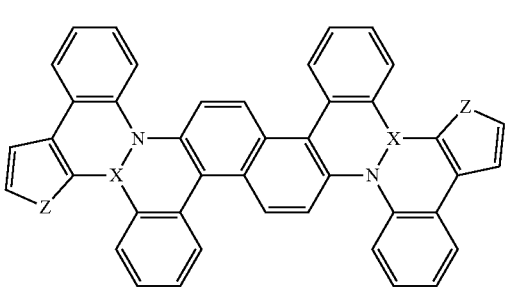
126
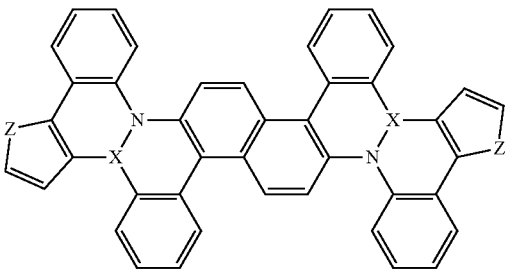
127
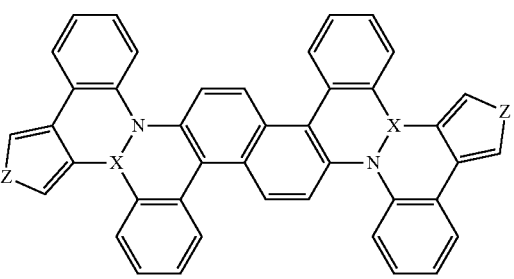

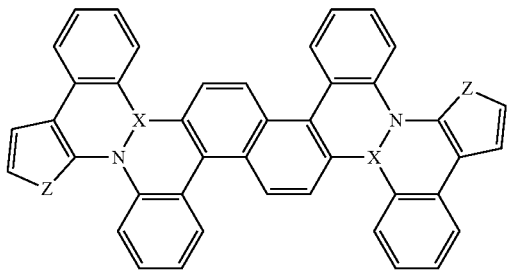
128
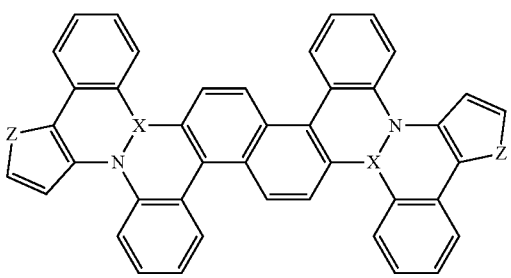
129
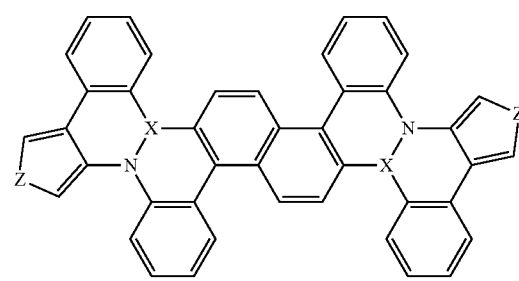
130
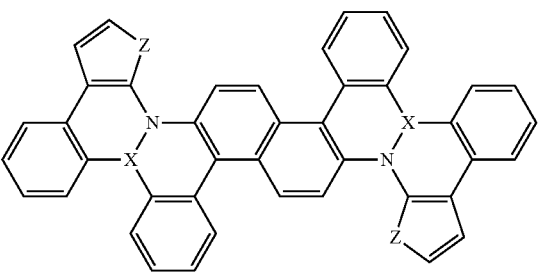
131
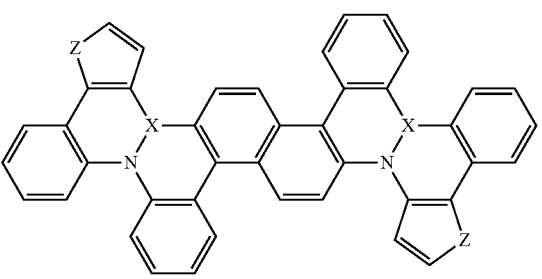
132
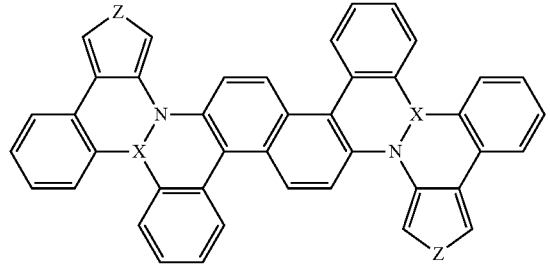
133
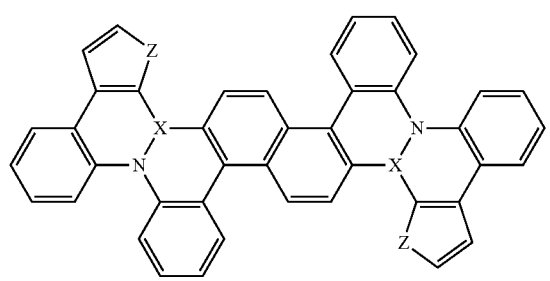
134
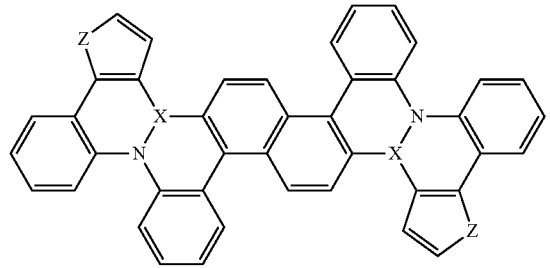
135
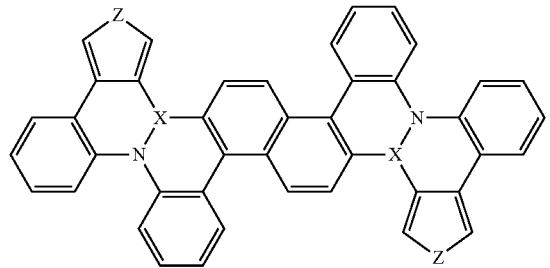
136
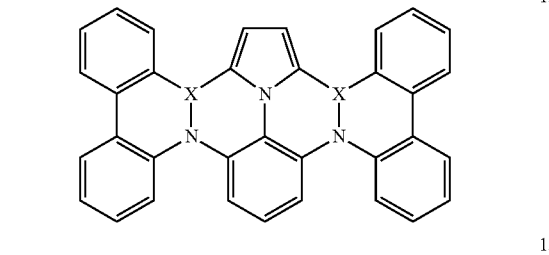
137
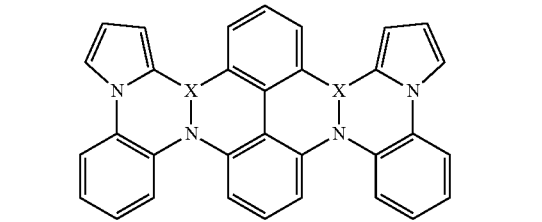
138

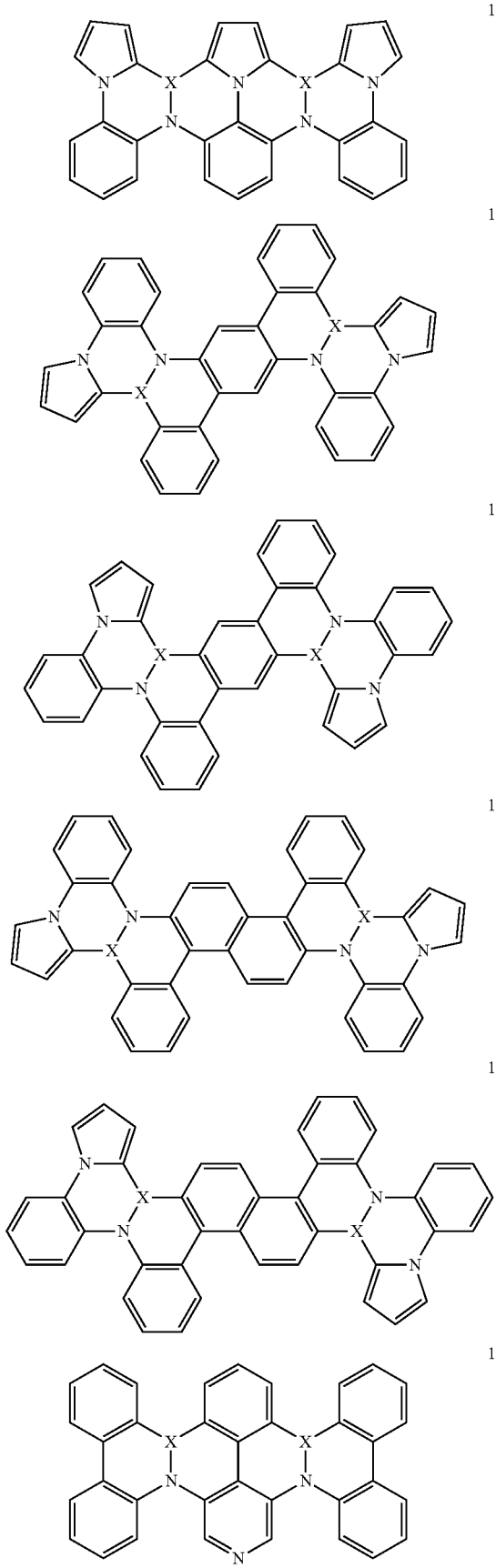

(In the formulae, X and Z are as defined above.)

Examples of metals in groups 3 to 11 of the periodic table and metals or metalloids in group 13 or 14 of the periodic table, represented by X, include those described below.

Group 3: Sc, Y, lanthanoid
Group 4: Ti, Zr, Hf
Group 5: V, Nb, Ta
Group 6: Cr, Mo, W
Group 7: Mn, Tc, Re
Group 8: Fe, Ru, Os
Group 9: Co, Rh, Ir
Group 10: Ni, Pd, Pt
Group 11: Cu, Ag, Au
Group 13: Al, Ga, In, Tl
Group 14: Si, Ge, Sn, Pb The metals in groups 3 to 11 of the periodic table and the metals or metalloids in group 13 or 14 of the periodic table, represented by X, are each optionally substituted. Here, "optionally substituted" means that the metals or metalloids may include 0 to 3 substituent groups R (wherein R is as defined above), or 0 to 3 neutral ligands $R^1$.

Examples of neutral ligands $R^1$ include aromatic compounds having a nitrogen atom as a ring atom, such as pyridine, bipyridine, phenanthroline, terpyridine, imidazole, pyrimidine, pyrazine, quinoline, isoquinoline, and acridine; and derivatives thereof. However, when X has both R and $R^1$, R and $R^1$ may form a single compound (8-hydroxyquinoline), as in the following Case (3).

For example, a compound having a neutral ligand $R^1$ can be produced in the following manner.

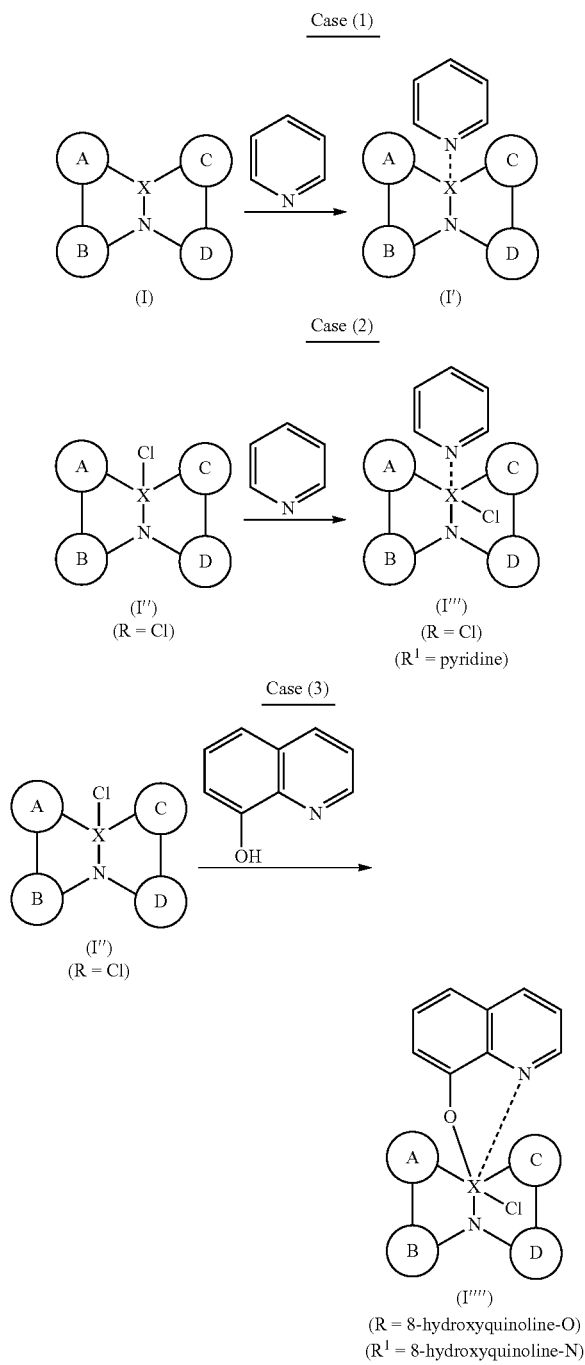

(In the formulae, (R) indicates that $R^1$ is the R group defined above, and ($R^1$) indicates that $R^1$ is a neutral ligand.)

Case (1) represents a case where a neutral ligand ($R^1$) binds to X (metal or metalloid) of (I) to obtain compound (I').

Case (2) represents a case where a neutral ligand ($R^1$) further binds to (I") in which R=Cl and X (metal or metalloid) is substituted with the R group, to obtain compound (I''').

Case (3) represents a method for obtaining compound (I'''') having (R) and ($R^1$), by causing 8-hydroxyquinoline to act on (I") in which R=Cl and X (metal or metalloid) is substituted with the R group, to substitute Cl, which is the R group, with an oxygen atom of a phenolic hydroxyl group; and to simultaneously cause coordination of an endocyclic N atom ($R^1$ group) of quinoline, which is a neutral ligand.

A compound having a neutral ligand can be easily produced by those skilled in the art by referring to Case (1) to Case (3).

$X_1$ can be changed to $X_2$ in a manner similar to that described below.

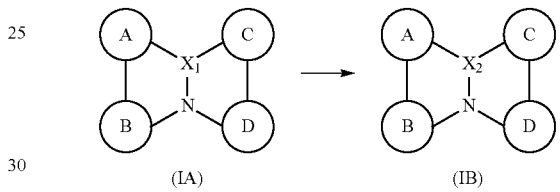

$X_1$ and $X_2$ can be changed when the electronegativities thereof are about the same as, or are, $X_1 < X_2$. For example, when $X_1$=Ge—R, $X_2$ can be changed as B, P, P=O, P=S, P=Se, As, As=O, As=S, As=Se, Sb, Sb=O, Sb=S, Sb=Se, Mo, W, Ru, Os, Rh, Ir, Pd, Pt, Au, or Pb (these metals are optionally substituted). As the changing method, with respect to compound (IA) having $X_1$, 1 mol to an excessive amount of a halide, an alkoxy derivative, an aryloxy derivative, an acyloxy derivative, or a haloamino derivative of $X_2$, 0 mole to an excessive amount of a Lewis acid, 0 mole to an excessive amount of a base are added and allowed to react by stirring for 30 minutes to 24 hours at a temperature of room temperature to about 250° C. in a solvent or under a non-solvent condition to obtain compound (IB) having $X_2$.

Examples of the solvents that can be used include anhydrous ether solvents such as anhydrous diethyl ether, anhydrous THF, and anhydrous dibutyl ether; aromatic hydrocarbon solvents such as benzene, toluene, xylene, and mesitylene; aromatic halide-based solvents such as chlorobenzene and 1,2-dichlorobenzene; and the like.

Examples of the Lewis acid that can be used include $AlCl_3$, $AlBr_3$, $BF_3 \cdot OEt_2$, $BCl_3$, $BBr_3$, $GaCl_3$, $GaBr_3$, $InCl_3$, $InBr_3$, $In(OTf)_3$, $SnCl_4$, $SnBr_4$, AgOTf, $Sc(OTf)_3$, $ZnCl_2$, $ZnBr_2$, $Zn(OTf)_2$, $MgCl_2$, $MgBr_2$, $Mg(OTf)_2$, and the like.

Examples of the base that can be used include diisopropylethylamine, 2,2,6,6-tetra methyl piperidine, 1,2,2,6,6-pentamethylpiperidine, 2,4,6-collidine, 2,6-lutidine, triethylamine, triisobutylamine, and the like.

When $X_2$=P, a compound in which $X_2$ is P=S can be directly obtained by conducting the reaction that uses the Lewis acid and the base in the presence of sulfur (S8).

A compound having bound thereto a sulfur atom can also be similarly obtained when $X_2$ is other elements such as As and Sb.

Although a description of the compound having the partial structure of general formula (I) has been provided above, a neutral ligand can be introduced, and a conversion of $X_1$ to $X_2$ is similarly possible, with compounds of general formulae (II) to (XIVA); compounds of general formulae (II-1) to (II-54), compounds of general formulae (II') to (XXIII'); compounds of general formulae (II'-1) to (XIV'-1A); and compounds of 1 to 149.

Examples of preferable X group include B, P, P=O, P=S, Si—R, Ge—R, Ga, Pt, Ru, Ir, Au, and the like.

As described herein, "two adjacent $Y^a$s on the same ring, together with a bond therebetween, form N—, O, S, or Se" means that when adjacent $Y^a$s are bound with a double bond, such as $Y^a=Y^a$, $Y^a=Y^a$ can be N—, O, S, or Se; and when adjacent $Y^a$s are bound with a single bond, such as $Y^a$—$Y^a$, a structure shown in the following formulae can be obtained:

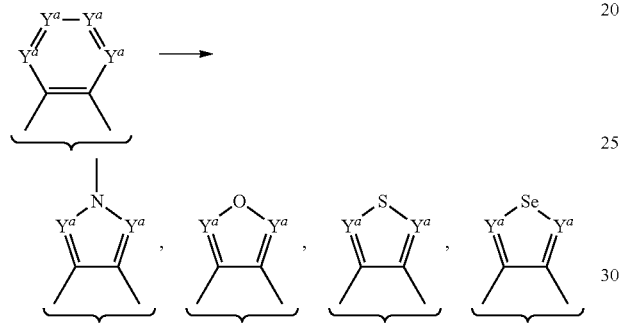

(in the formulae, $Y^a$ is as defined above).

The term "two adjacent Ys on the same ring, together with a bond therebetween, form NR, O, S, or Se" has the same meaning.

In the present specification, "adjacent R groups" may be adjacent groups on the same ring, or the closest R groups each existing on adjacent rings.

Examples of aromatic rings described as "an optionally substituted aromatic ring" include a benzene ring, naphthalene ring, azulene ring, biphenylene ring, fluorene ring, anthracene ring, indacene ring, phenanthrene ring, phenalene ring, pyrene ring, chrysene ring, triphenylene ring, fluoranthene ring, acephenanthrylene ring, aceanthrylene ring, picene ring, naphthacene ring, perylene ring, acenaphthylene ring, acenaphthene ring, indane ring, indene ring, and tetrahydronaphthalene ring.

Examples of heteroaromatic rings described as "an optionally substituted heteroaromatic ring" include a furan ring, thiophene ring, selenophene ring, pyrrole ring, imidazole ring, triazole ring, isothiazole ring, oxazole ring, isoxazole ring, triazole ring, borole ring, phosphole ring, silole ring, azaborine ring, pyridine ring, pyrimidine ring, triazine ring, pyran ring, indole ring, isoindole ring, quinoline ring, isoquinoline ring, quinoxaline ring, benzoxazole ring, benzothiazole ring, benzisoxazole ring, benzisothiazole ring, benzofuran ring, benzothiophene ring, benzopyran ring, benzimidazole ring, benzoborole ring, benzophosphole ring, benzosilole ring, benzazaborine ring, carbazole ring, indolizine ring, acridine ring, phenazine ring, phenanthridine ring, phenanthroline ring, phenoxazine ring, phenothiazine ring, benzoselenophene ring, naphthofuran ring, naphthoxazole ring, naphthothiazole ring, naphthoisoxazole ring, naphthoimidazole ring, naphthoborole ring, naphthophosphole ring, naphthosilole ring, naphthoazaborine ring, naphthopyran ring, benzoindole ring, benzisoindole ring, benzoquinoline ring, benzisoquinoline ring, benzoquinoxaline ring, and those in the following formulae:

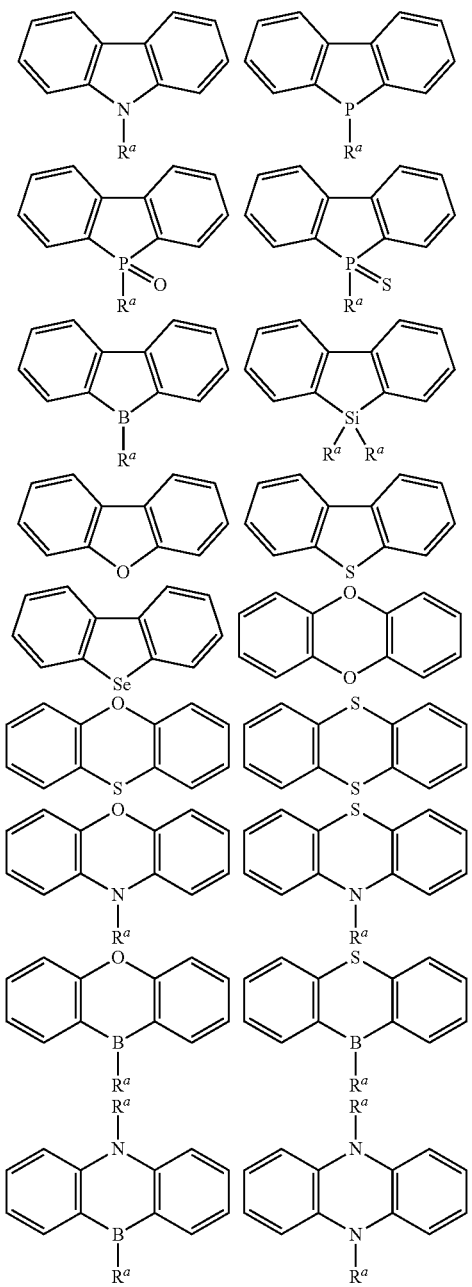

(in the formulae, $R^a$ is as defined above).

The number of substituent groups of an optionally substituted aromatic ring or an optionally substituted heteroaromatic ring is 1 to 4, and preferably 1, 2, or 3. Examples of the substituent group of an optionally substituted aromatic ring or an optionally substituted heteroaromatic ring include groups represented by R.

Examples of "a five- or six-membered monocyclic group, bicyclic group, or tricyclic group optionally having a heteroatom" include benzene, naphthalene, azulene, biphenylene, fluorene, anthracene, indacene, phenanthrene, phenalene, acenaphthylene, acenaphthene, indane, indene, tetrahydronaphthalene, cyclopentadiene, cyclohexadiene, furan, thiophene, selenophene, pyrrole, imidazole, triazole, isothiazole, oxazole, isoxazole, triazole, borole, phosphole, silole, azaborine, pyridine, pyrimidine, triazine, pyran, indole, isoindole, quinoline, isoquinoline, quinoxaline, benzoxazole, benzothiazole, benzisoxazole, benzisothiazole, benzofuran, benzothiophene, benzopyran, benzimidazole, benzoborole, benzophosphole, benzosilole, benzazaborine, indolizine, acridine, phenazine, phenanthridine, phenanthroline, benzoselenophene, naphthofuran, naphthoxazole, naphthothiazole, naphthoisoxazole, naphthoimidazole, naphthoborole, naphthophosphole, naphthosilole, naphthoazaborine, naphthopyran, benzoindole, benzisoindole, benzoquinoline, benzisoquinoline, benzoquinoxaline, those in the following formulae:

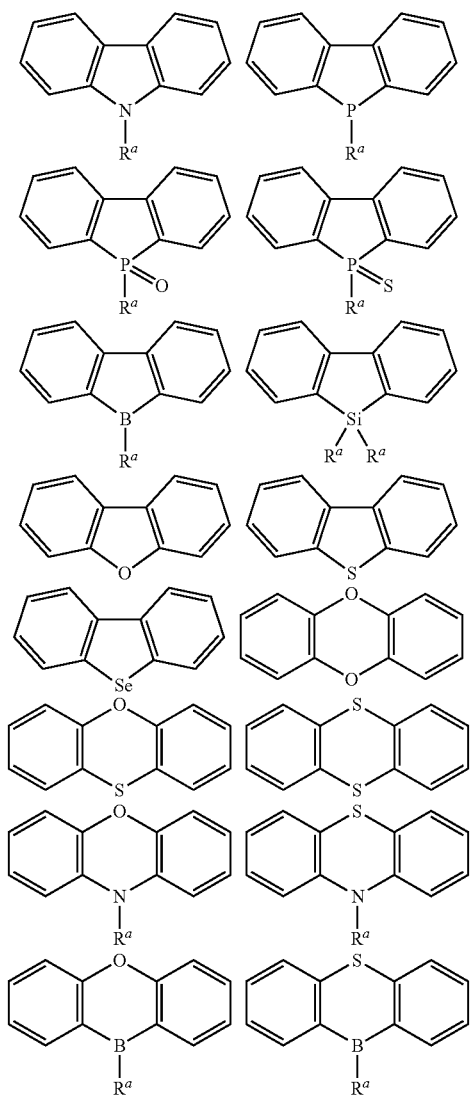

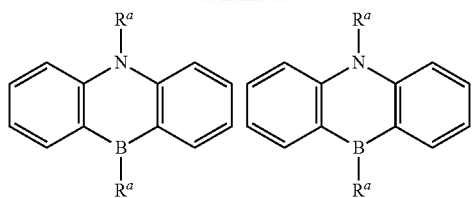

(in the formulae, $R^a$ is as defined above), or a five- or six-membered ring group having X group.

Examples of "a bicyclic group or a tricyclic group optionally having a heteroatom" include naphthalene, azulene, biphenylene, fluorene, anthracene, indacene, phenanthrene, phenalene, acenaphthylene, acenaphthene, indane, indene, tetrahydronaphthalene, indole, isoindole, quinoline, isoquinoline, quinoxaline, benzoxazole, benzothiazole, benzisoxazole, benzisothiazole, benzofuran, benzothiophene, benzopyran, benzimidazole, benzoborole, benzophosphole, benzosilole, benzazaborine, indolizine, acridine, phenazine, phenanthridine, phenanthroline, benzoselenophene, naphthofuran, naphthoxazole, naphthothiazole, naphthoisoxazole, naphthoimidazole, naphthoborole, naphthophosphole, naphthosilole, naphthoazaborine, naphthopyran, benzoindole, benzisoindole, benzoquinoline, benzisoquinoline, benzoquinoxaline, and those in the following formulae:

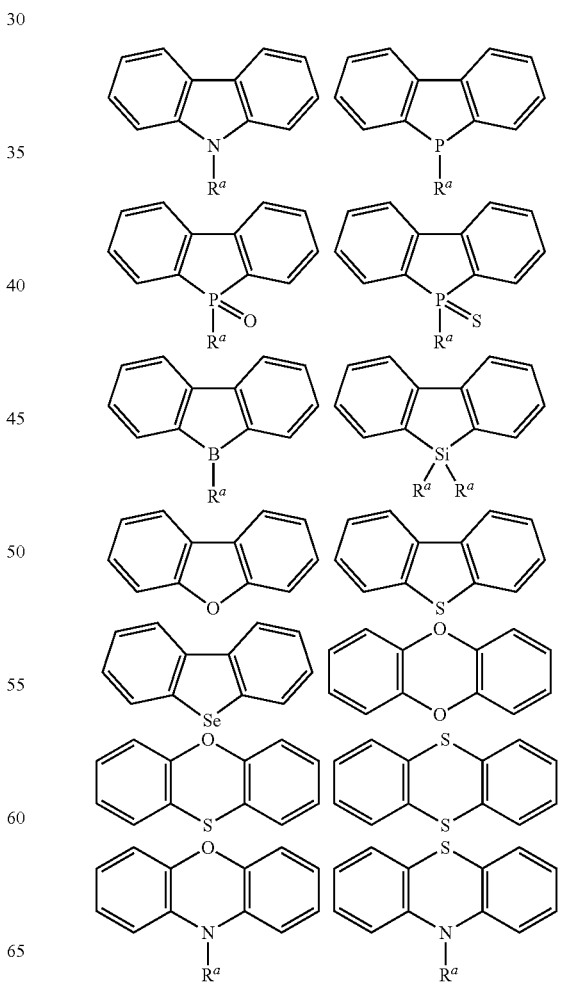

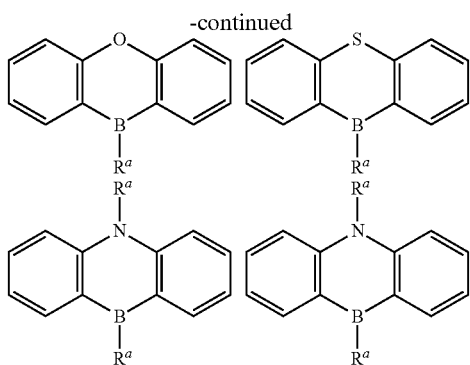

(in the formulae, $R^a$ is as defined above).

In the present specification, although the number of carbon atoms is specified as "$C_{1-20}$ alkylcarbonyl," this number of carbon atoms only modifies the group or moiety that immediately follows. Thus, in the above-described case, since $C_{1-20}$ only modifies alkyl, "$C_1$ alkylcarbonyl" corresponds to acetyl.

Alkyl groups and alkyl moieties may be linear or branched.

In the present specification, an alkyl moiety not only includes respective alkyl groups of an optionally substituted alkyl group, $C_{1-20}$ alkylsulfonyl group, $C_{1-20}$ alkylsulfonylamino group, $C_{1-20}$ alkylcarbonylamino group, and $C_{1-20}$ alkylcarbonyl group, but also includes an alkyl group of a monoalkylamino group, a mono- or di-alkylsulfamoyl group, and a mono- or di-alkylcarbamoyl group.

An aryl moiety refers to an aryl group of a mono- or di-aryl-substituted alkenyl group, arylethynyl group, aryloxy group, monoarylamino group, or an optionally substituted aryl group.

A heteroaryl moiety refers to a heteroaryl group of a monoheteroarylamino group, mono- or heteroaryl-substituted alkenyl group, heteroarylethynyl group, or an optionally substituted heteroaryl group.

Although "halogen atom" refers to fluorine, chlorine, bromine, or iodine, fluorine, chlorine, and bromine are preferable.

The "$C_{1-20}$ alkyl group" may be linear, branched, or cyclic; and is, for example, a $C_{1-20}$ alkyl group such as methyl group, ethyl group, n-propyl group, isopropyl group, n-butyl group, isobutyl group, tert-butyl group, n-pentyl group, isopentyl group, hexyl group, heptyl group, octyl group, nonyl group, decyl group, undecyl group, dodecyl group, tetradecyl group, hexadecyl group, octadecyl group, and eicosyl group, preferably a $C_{1-10}$ alkyl group, and more preferably a $C_{1-6}$ alkyl group.

Examples of the "$C_{3-8}$ cycloalkyl group" include cyclopropyl group, cyclobutyl group, cyclopentyl group, cyclohexyl group and cycloheptyl group, and cyclooctyl group.

The "$C_{2-20}$ alkenyl group" may be linear, branched, or cyclic; and refers to one that has at least one double bond. Examples thereof include vinyl group, allyl group, 1-propenyl group, 2-methyl-2-propenyl group, isopropenyl group, 1-, 2-, or 3-butenyl group, 2-, 3-, or 4-pentenyl group, 2-methyl-2-butenyl group, 3-methyl-2-butenyl group, 5-hexenyl group, 1-cyclopentenyl group, 1-cyclohexenyl group, and 3-methyl-3-butenyl group, preferably a $C_{2-12}$ alkenyl group, and more preferably a $C_{2-6}$ alkenyl group.

The "$C_{2-20}$ alkynyl group" may be linear, branched, or cyclic; and refers to one that has at least one triple bond. Examples thereof include ethynyl group, 1- or 2-propynyl group, 1-, 2-, or 3-butynyl group, 1-methyl-2-propynyl group, 1-pentynyl group, 1-hexynyl group, 1-heptynyl group, 1-octynyl group, 1-nonenyl group, 1-decynyl group, 1-undecenyl group, and 1-dodecynyl group, preferably a $C_{2-10}$ alkynyl group, and more preferably a $C_{2-6}$ alkynyl group.

The "hydroxy $C_{1-20}$ alkyl group" may be linear or branched; and is, for example, a hydroxy $C_{1-20}$ alkyl group such as hydroxymethyl group, hydroxyethyl group, hydroxy n-propyl group, hydroxyisopropyl group, hydroxy n-butyl group, hydroxyisobutyl group, hydroxy tert-butyl group, hydroxy n-pentyl group, hydroxyisopentyl group, hydroxyhexyl group, hydroxyheptyl group, hydroxyoctyl group, hydroxynonyl group, hydroxydecyl group, hydroxyundecyl group, hydroxydodecyl group, hydroxytetradecyl group, hydroxyhexadecyl group, hydroxyoctadecyl group, and hydroxyeicosyl group, preferably a hydroxy $C_{1-10}$ alkyl group, and more preferably a hydroxy $C_{1-6}$ alkyl group.

The "$C_{1-20}$ alkoxy group" may be linear or branched; and is, for example, a $C_{1-20}$ alkoxy group such as methoxy group, ethoxy group, propoxy group, isopropoxy group, butoxy group, isobutoxy group, tert-butoxy group, pentyloxy group, isopentyloxy group, hexyloxy group, heptyloxy group, octyloxy group, nonyloxy group, decyloxy group, undecyloxy group, dodecyloxy group, tetradecyloxy group, hexadecyloxy group, octadecyloxy group, and eicosyloxy group, preferably a $C_{1-10}$ alkoxy group, and more preferably a $C_{1-6}$ alkoxy group.

As a trifluoroethoxy group, $CF_3CH_2O-$ is preferable.

The "$C_{2-12}$ perfluoroalkyl group" may be linear or branched; and is, for example, a $C_{2-12}$ perfluoroalkyl group such as perfluoroethyl group, perfluoro n-propyl group, perfluoroisopropyl group, perfluoro n-butyl group, perfluoroisobutyl group, perfluoro tert-butyl group, perfluoro n-pentyl group, perfluoroisopentyl group, perfluorohexyl group, perfluoroheptyl group, perfluorooctyl group, perfluorononyl group, perfluorodecyl group, and perfluoroundecyl group, preferably a $C_{2-10}$ perfluoroalkyl group, and more preferably a $C_{2-6}$ perfluoroalkyl group.

The "$C_{2-12}$ perfluoroalkoxy group" may be linear or branched; and is, for example, a $C_{2-12}$ perfluoroalkoxy group such as perfluoroethoxy group, perfluoro n-propyloxy group, perfluoroisopropyloxy group, perfluoro n-butoxy group, perfluoroisobutoxy group, perfluoro tert-butoxy group, perfluoro n-pentyloxy group, perfluoroisopentyloxy group, perfluorohexyloxy group, perfluoroheptyloxy group, perfluorooctyloxy group, perfluorononyloxy group, perfluorodecyloxy group, and perfluoroundecyloxy group, preferably a $C_{2-10}$ perfluoroalkoxy group, and more preferably a $C_{2-6}$ perfluoroalkoxy group.

In a monoalkylamino group, mono- or di-alkylcarbamoyl group, or mono- or di-alkylsulfamoyl group, "monoalkyl" refers to one hydrogen atom bound to a nitrogen atom of an amino group, carbamoyl group, or sulfamoyl group, being substituted with a $C_{1-20}$ alkyl; and "dialkyl" refers to two hydrogen atoms bound to a nitrogen atom of an amino group, carbamoyl group, or sulfamoyl group, being substituted with the same or different $C_{1-20}$ alkyl, or being substituted with a three- to eight-membered, preferably five- or six-membered, nitrogen-containing cyclic group.

Nitrogen-containing cyclic group refers to morpholino group, 1-pyrrolidinyl group, piperidino, and 4-methyl-1-piperazinyl group.

Examples of the monoalkylamino group include amino group that is mono-substituted with a $C_{1-20}$ alkyl group, such as methylamino group, ethylamino group, n-propylamino group, isopropylamino group, n-butylamino group, isobutylamino group, tert-butylamino group, n-pentylamino group, isopentylamino group, and hexylamino group, preferably a $C_{1-10}$ alkyl group, and more preferably a $C_{1-6}$ alkyl group.

Examples of the monoalkylcarbamoyl group include carbamoyl that is mono-substituted with a $C_{1-20}$ alkyl group such as methylcarbamoyl group, ethylcarbamoyl group, n-propylcarbamoyl group, isopropylcarbamoyl group, n-butylcarbamoyl group, isobutylcarbamoyl group, tert-butylcarbamoyl group, n-pentylcarbamoyl group, isopentylcarbamoyl group, and hexylcarbamoyl group, preferably a $C_{1-10}$ alkyl group, and more preferably a $C_{1-6}$ alkyl group.

Examples of a dialkylcarbamoyl group include carbamoyl that is di-substituted with a $C_{1-20}$ alkyl group such as dimethylcarbamoyl group, diethylcarbamoyl group, di-n-propylcarbamoyl group, diisopropylcarbamoyl group, di-n-butylcarbamoyl group, diisobutylcarbamoyl group, di-tert-butylcarbamoyl group, di-n-pentylcarbamoyl group, diisopentylcarbamoyl group, and dihexylcarbamoyl group, preferably a $C_{1-10}$ alkyl group, and more preferably a $C_{1-6}$ alkyl group.

Examples of the monoalkylsulfamoyl group include sulfamoyl that is mono-substituted with a $C_{1-20}$ alkyl group such as methylsulfamoyl group, ethylsulfamoyl group, n-propylsulfamoyl group, isopropylsulfamoyl group, n-butylsulfamoyl group, isobutylsulfamoyl group, tert-butylsulfamoyl group, n-pentylsulfamoyl group, isopentylsulfamoyl group, and hexylsulfamoyl group, preferably a $C_{1-10}$ alkyl group, and more preferably a $C_{1-6}$ alkyl group.

Examples of the dialkylsulfamoyl group include sulfamoyl that is di-substituted with a $C_{1-20}$ alkyl group such as dimethylsulfamoyl group, diethylsulfamoyl group, di-n-propylsulfamoyl group, diisopropylsulfamoyl group, di-n-butylsulfamoyl group, diisobutylsulfamoyl group, di-tert-butylsulfamoyl group, di-n-pentylsulfamoyl group, diisopentylsulfamoyl group, and dihexylsulfamoyl group, preferably a $C_{1-10}$ alkyl group, and more preferably a $C_{1-6}$ alkyl group.

"Aryl group" refers to a monocyclic or polycyclic group including a five- or six-membered aromatic hydrocarbon ring, and specific examples thereof include phenyl group, naphthyl group, fluorenyl group, anthryl group, biphenylyl group, tetrahydronaphthyl group, 2,3-dihydro-1,4-dioxanaphthalenyl group, indanyl group, indenyl group, indacenyl group, pyrenyl group, naphthacenyl group, perylenyl group, chrysenyl group, acenaphthyl group, acenaphthenyl group, and phenanthryl group; and these are optionally substituted with 1 to 5 atoms or groups defined above.

"Heteroaryl group" refers to a monocyclic or polycyclic group including a five- or six-membered aromatic ring having 1 to 3 heteroatoms selected from N, O, S, Se, and Si; and when the "heteroaryl group" is polycyclic, at least one ring thereof may be an aromatic ring. Specific examples thereof include furyl group, thienyl group, selenophene group, pyrrolyl group, imidazolyl group, pyrazolyl group, oxazolyl group, thiazolyl group, isoxazolyl group, isothiazolyl group, pyridyl group, pyrazinyl group, pyrimidinyl group, pyridazinyl group, indolyl group, quinolyl group, isoquinolyl group, carbazolyl group, chromanyl group, silole group, benzo[b]silole group, benzo[b]furyl group, benzo[b]thienyl group, benzo[b]selenophene group, benzoindolyl group, benzoquinolyl group, benzisoquinolyl group, benzocarbazolyl group, benzochromanyl group, benzimidazolyl group, benzopyrazolyl group, benzoxazolyl group, benzothiazolyl group, benzisoxazolyl group, benzisothiazolyl group, dibenzo[b,d]furyl group, dibenzo[b,d]thienyl group, thieno[3,4-b]thienyl group, thieno[3,2-b]thienyl group, and fluoro[3,2-b]furyl group; and these are optionally substituted with 1 to 5 atoms or groups defined above.

Examples of monoarylamino groups include monoarylamino groups whose aryl group is as defined above.

Examples of monoheteroarylamino groups include monoheteroarylamino groups whose heteroaryl group is as defined above.

The "$C_{1-20}$ alkylsulfonyl group" may be linear, branched, or cyclic; and is, for example, a $C_{1-20}$ alkylsulfonyl group such as methylsulfonyl group, ethylsulfonyl group, n-propylsulfonyl group, isopropylsulfonyl group, n-butylsulfonyl group, isobutylsulfonyl group, tert-butylsulfonyl group, n-pentylsulfonyl group, isopentylsulfonyl group, hexylsulfonyl group, heptylsulfonyl group, octylsulfonyl group, nonylsulfonyl group, decylsulfonyl group, undecylsulfonyl group, dodecylsulfonyl group, tetradecylsulfonyl group, hexadecylsulfonyl group, octadecylsulfonyl group, and eicosylsulfonyl group, preferably a $C_{1-10}$ alkylsulfonyl group, and more preferably a $C_{1-6}$ alkylsulfonyl group.

The "$C_{1-20}$ alkylcarbonylamino group" may be linear, branched, or cyclic; and is, for example a $C_{1-20}$ alkylcarbonylamino group such as methylcarbonylamino group, ethylcarbonylamino group, n-propylcarbonylamino group, isopropylcarbonylamino group, n-butylcarbonylamino group, isobutylcarbonylamino group, tert-butylcarbonylamino group, n-pentylcarbonylamino group, isopentylcarbonylamino group, hexylcarbonylamino group, heptylcarbonylamino group, octylcarbonylamino group, nonylcarbonylamino group, decylcarbonylamino group, undecylcarbonylamino group, dodecylcarbonylamino group, tetradecylcarbonylamino group, hexadecylcarbonylamino group, octadecylcarbonylamino group, and eicosylcarbonylamino group, preferably a $C_{1-10}$ alkylcarbonylamino group, and more preferably a $C_{1-6}$ alkylcarbonylamino group.

Examples of the $C_{1-20}$ alkoxycarbonylamino group (e.g., a $C_{1-12}$ alkoxycarbonylamino group and a $C_{1-6}$ alkoxycarbonylamino group) include methoxycarbonylamino group, ethoxycarbonylamino group, propoxycarbonylamino group, isopropoxycarbonylamino group, butoxycarbonylamino group, isobutoxycarbonylamino group, tert-butoxycarbonylamino group, pentyloxycarbonylamino group, isopentyloxycarbonylamino, and hexyloxycarbonylamino.

The $C_{1-20}$ alkylsulfonylamino group (e.g., a $C_{1-10}$ alkylsulfonylamino group and a $C_{1-6}$ alkylsulfonylamino group) is, for example, a $C_{1-12}$ alkylsulfonylamino group such as methylsulfonylamino group, ethylsulfonylamino group, n-propylsulfonylamino group, isopropylsulfonylamino group, n-butylsulfonylamino group, isobutylsulfonylamino group, tert-butylsulfonylamino group, n-pentylsulfonylamino group, isopentylsulfonylamino group, hexylsulfonylamino, octylsulfonylamino group, nonylsulfonylamino group, decylsulfonylamino group, undecylsulfonylamino group, dodecylsulfonylamino group, tetradecylsulfonylamino group, hexadecylsulfonylamino group, octadecylsulfonylamino group, and eicosylsulfonylamino group, preferably a $C_{1-10}$ alkylsulfonylamino group, and more preferably a $C_{1-6}$ alkylsulfonylamino group.

Examples of the $C_{1-20}$ alkoxycarbonyl group (e.g., a $C_{1-10}$ alkoxycarbonyl group and a $C_{1-6}$ alkoxycarbonyl group) include methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group, isopentyloxycarbonyl group, and hexyloxycarbonyl group.

Examples of the $C_{1-20}$ alkylcarbonyl group (e.g., a $C_{1-10}$ alkylcarbonyl group and a $C_{1-6}$ alkylcarbonyl group) include acetyl group, propionyl group, butyryl group, pentylcarbonyl group, hexycarbonyl group, heptylcarbonyl group, octylcarbonyl group, nonylcarbonyl group, and decylcarbonyl group.

Examples of the monoaryl-substituted alkenyl group (e.g., a monoaryl-substituted $C_{2-12}$ alkenyl group and a monoaryl-substituted $C_{2-6}$ alkenyl group) include a monoaryl-substituted alkenyl group whose aryl group is as defined above, such as styryl group.

Examples of the diaryl-substituted alkenyl group (e.g., a diaryl-substituted $C_{2-12}$ alkenyl group, and a diaryl-substituted $C_{2-6}$ alkenyl group) include a diaryl-substituted alkenyl group whose aryl group is as defined above, such as diphenylvinyl group.

Examples of the monoheteroaryl-substituted alkenyl group (e.g., a monoheteroaryl-substituted $C_{2-12}$ alkenyl group and a monoheteroaryl-substituted $C_{2-6}$ alkenyl group) include a monoheteroaryl-substituted alkenyl group whose heteroaryl group is as defined above, such as thienylvinyl group.

Examples of the diheteroaryl-substituted alkenyl group (e.g., a diheteroaryl-substituted $C_{2-12}$ alkenyl group and a diheteroaryl-substituted $C_{2-6}$ alkenyl group) include a diheteroaryl-substituted alkenyl group whose heteroaryl group is as defined above, such as dithienylvinyl group.

Examples of the arylethynyl group include an arylethynyl group whose aryl group is as defined above.

Examples of the heteroarylethynyl group include a heteroarylethynyl group whose heteroaryl group is as defined above.

Examples of the aryloxy group include an aryloxy group whose aryl group is as defined above.

$R^a$ represents an optionally substituted alkyl group, an optionally substituted aryl group, or an optionally substituted heteroaryl group. Examples of "alkyl groups" in the optionally substituted alkyl group include the above-described $C_{1-20}$ alkyl groups, and examples of "aryl groups" in the optionally substituted aryl group includes the above-described aryl groups. Examples of "heteroaryl groups" in the optionally substituted heteroaryl group include the above-described heteroaryl groups.

Next, a method for producing the compound of the present invention will be described.

The compounds of general formulae (II) and (IIA) of the present invention can be synthesized in accordance with the following scheme 1.

It should be noted that the compound in general formula (IIA) is equivalent to the compound in general formula (II) when two R groups of two adjacent benzene rings that are bound via N atom represents a single bond.

<Scheme 1>

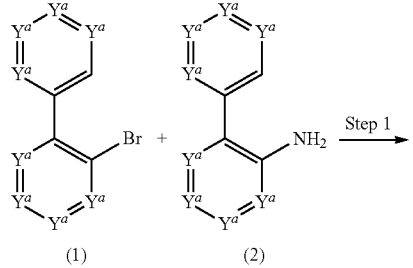

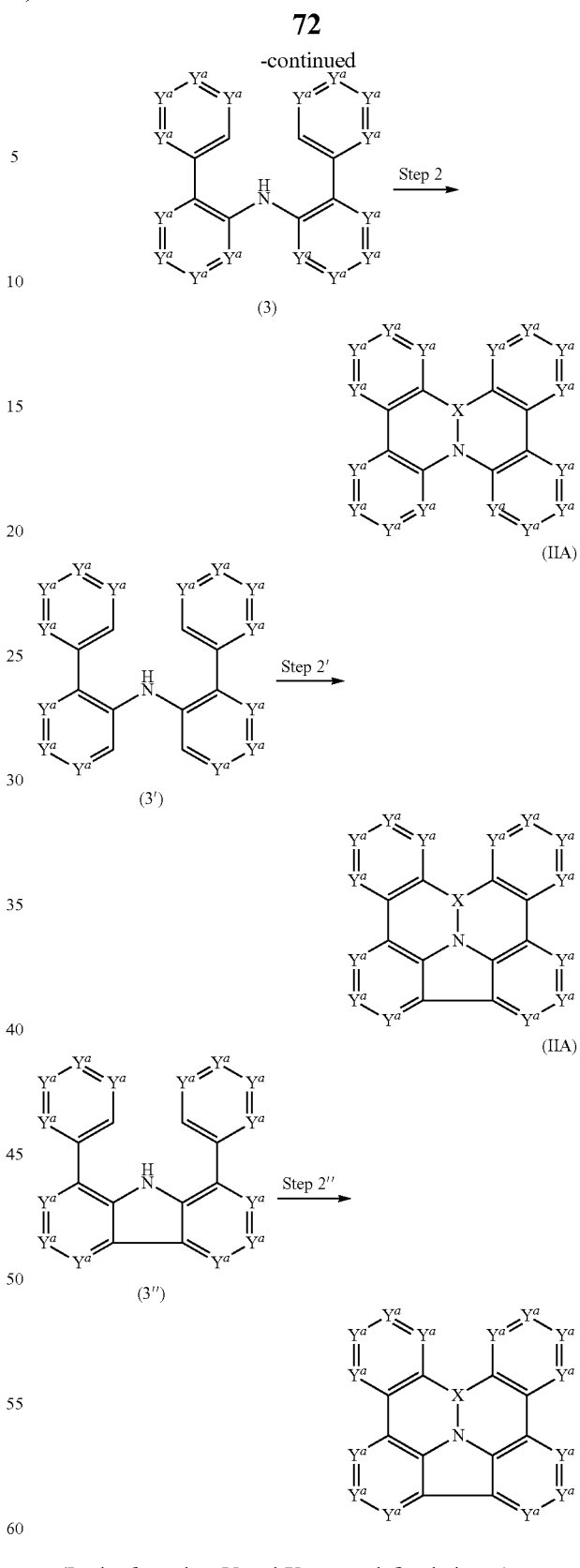

(In the formulae, V and X are as defined above.)

Step 1

In the reaction, with respect to 1 mol of the compound of formula (1), about 1 mol to an excessive amount of a base such as alkyl lithiums such as n-BuLi, Grignard reagents such as n-BuMgBr, alkali metal hydrides such as NaH and KH, alkali metal alkoxides such as NaO$^t$Bu and KO$^t$Bu, and alkali metal carbonates such as Na$_2$CO$_3$, NaHCO$_3$, K$_2$CO$_3$, and Cs$_2$CO$_3$, and 1 mol to an excessive amount of the compound of formula (2) are used; and Pd(dba)$_2$ and P$^t$Bu$_3$ are further used.

The mixture is allowed to react by having it stirred for 30 minutes to 24 hours in a solvent at a temperature of −78° C. to about room temperature to obtain compound (3).

As the solvent, an anhydrous ether solvent such as anhydrous diethyl ether, anhydrous THF, or anhydrous dibutyl ether; or an aromatic hydrocarbon solvent such as benzene, toluene, xylene, or mesitylene can be used.

Step 2

Next, compound (3) is deprotonated using a deprotonating agent such as n-BuLi; and a compound including X (a halide, an alkoxy derivative, an aryloxy derivative, an acyloxy derivative, or a haloamino derivative of X) is added thereto to introduce an X group. Then, by performing a Friedel-Crafts-type reaction in the presence of a Lewis acid such as AlCl$_3$ and a base such as diisopropylethylamine, the compound of formula (II) can be obtained.

Examples of the compound including X include, when X=P, halides such as PF$_3$, PCl$_3$, PBr$_3$, and PI$_3$, alkoxy derivatives such as P(OMe)$_3$, P(OEt)$_3$, P(O-nPr)$_3$, P(O-iPr)$_3$, P(O-nBu)$_3$, P(O-iBu)$_3$, P(O-secBu)$_3$, and P(O-tert-Bu)$_3$, aryloxy derivatives such as P(OPh)$_3$ and P(O-naphthyl)$_3$, acyloxy derivatives such as P(OAc)$_3$, P(O-trifluoroacetyl)$_3$, P(O-propionyl)$_3$, P(O-butyryl)$_3$, and P(O-benzoyl)$_3$, and haloamino derivatives such as PCl(NMe$_2$)$_2$, PCl(NEt$_2$)$_2$, PCl(NPr$_2$)$_2$, PCl(NBu$_2$)$_2$, PBr(NMe$_2$)$_2$, PBr(NEt$_2$)$_2$, PBr(NPr$_2$)$_2$, and PBr(NBu$_2$)$_2$.

Even when X is other than P (specifically, when X is B, P=O, P=S, P=Se, As, As=O, As=S, As=Se, Sb, Sb=O, Sb=S, Sb=Se, a metal in groups 3 to 11 of the periodic table, a metal or metalloid in group 13 or 14 of the periodic table, or the like), a halide, an alkoxy derivative, an aryloxy derivative, an acyloxy derivative, or a haloamino derivative of X can be similarly used.

In the reaction, with respect to 1 mol of the compound of formula (3), 1 mol to an excessive amount of a deprotonating agent such as n-BuLi, 1 mol to an excessive amount of a compound including X, a catalytic amount to an excessive amount of a Lewis acid, and 0 mole to an excessive amount of a base are used. The mixture is allowed to react by having it stirred for 30 minutes to 24 hours in a solvent at a temperature of −78° C. to about the boiling point of the solvent to obtain the compound of formula (II). As the solvent, an anhydrous ether solvent such as anhydrous diethyl ether, anhydrous THF, or anhydrous dibutyl ether; an aromatic hydrocarbon solvent such as benzene, toluene, xylene, or mesitylene; or an aromatic halide based solvent such as chlorobenzene or 1,2-dichlorobenzene can be used. As the deprotonating agent, other than n-BuLi, an alkyl lithium such as MeLi, t-BuLi, or PhLi; a Grignard reagent such as MeMgBr, Et MgBr, or n-BuMgBr; or an alkali metal hydride such as NaH or KH can be used. Examples of the Lewis acid that can be used include AlCl$_3$, AlBr$_3$, BF$_3$.OEt$_2$, BCl$_3$, BBr$_3$, GaCl$_3$, GaBr$_3$, InCl$_3$, InBr$_3$, In(OTf)$_3$, SnCl$_4$, SnBr$_4$, AgOTf, Sc(OTf)$_3$, ZnCl$_2$, ZnBr$_2$, Zn(OTf)$_2$, MgCl$_2$, MgBr$_2$, Mg(OTf)$_2$, and the like. Examples of the base that can be used include diisopropylethylamine, 2,2,6,6-tetramethyl piperidine, 1,2,2,6,6-pentamethylpiperidine, 2,4,6-collidine, 2,6-lutidine, triethylamine, triisobutylamine, and the like. When X=P, a compound in which X is P=S can be obtained directly by conducting the reaction that uses the Lewis acid and the base in the presence of sulfur (S8). A compound having bound thereto a sulfur atom can also be similarly obtained when X is other elements such as As and Sb.

In Step 2', compound (3') is used instead of compound (3), and the compound of formula (IIA) can be obtained by performing a Friedel-Crafts-type reaction and a Scholl-type reaction under a condition similar to that in Step 2.

In Step 2", compound (3") is used instead of compound (3), and the compound of formula (IIA) can be obtained by performing a Friedel-Crafts-type reaction under a condition similar to that in Step 2.

The compounds of formulae (III), (IIIA), (IV), and (IVA) can be synthesized in accordance with the following scheme 2.

It should be noted that the compounds in general formulae (IIIA) and (IVA) are equivalent to the compounds in general formulae (III) and (IV) when two R groups of two adjacent benzene rings that are bound via N atom represents a single bond.

Furthermore, the compounds of general formulae (II-1) to (II-54), the compounds of general formulae (II') to (XXIII'), the compounds of general formulae (II'-1) to (XIV'-1A), and the compounds having a backbone of 1 to 149 can be easily synthesized by referring to schemes 1 to 8.

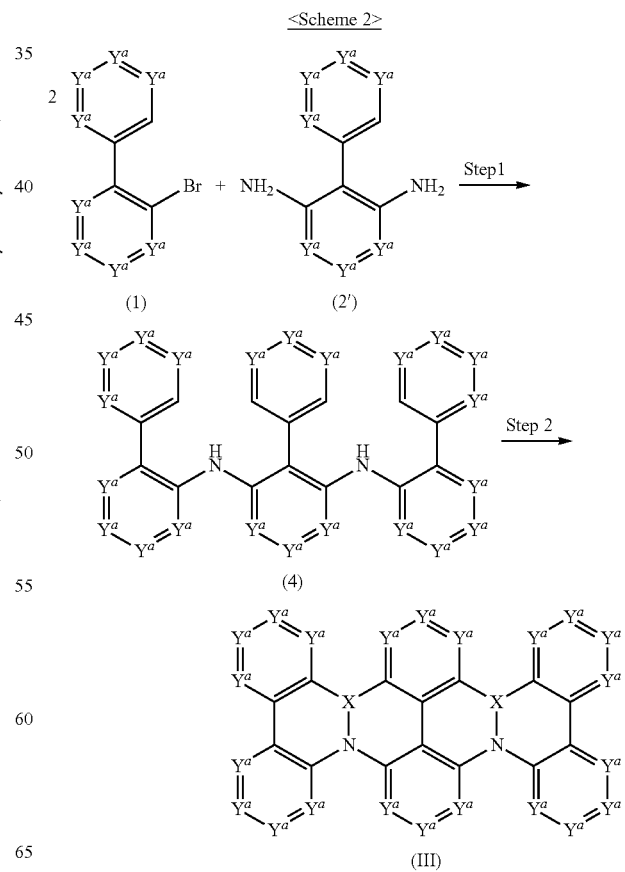

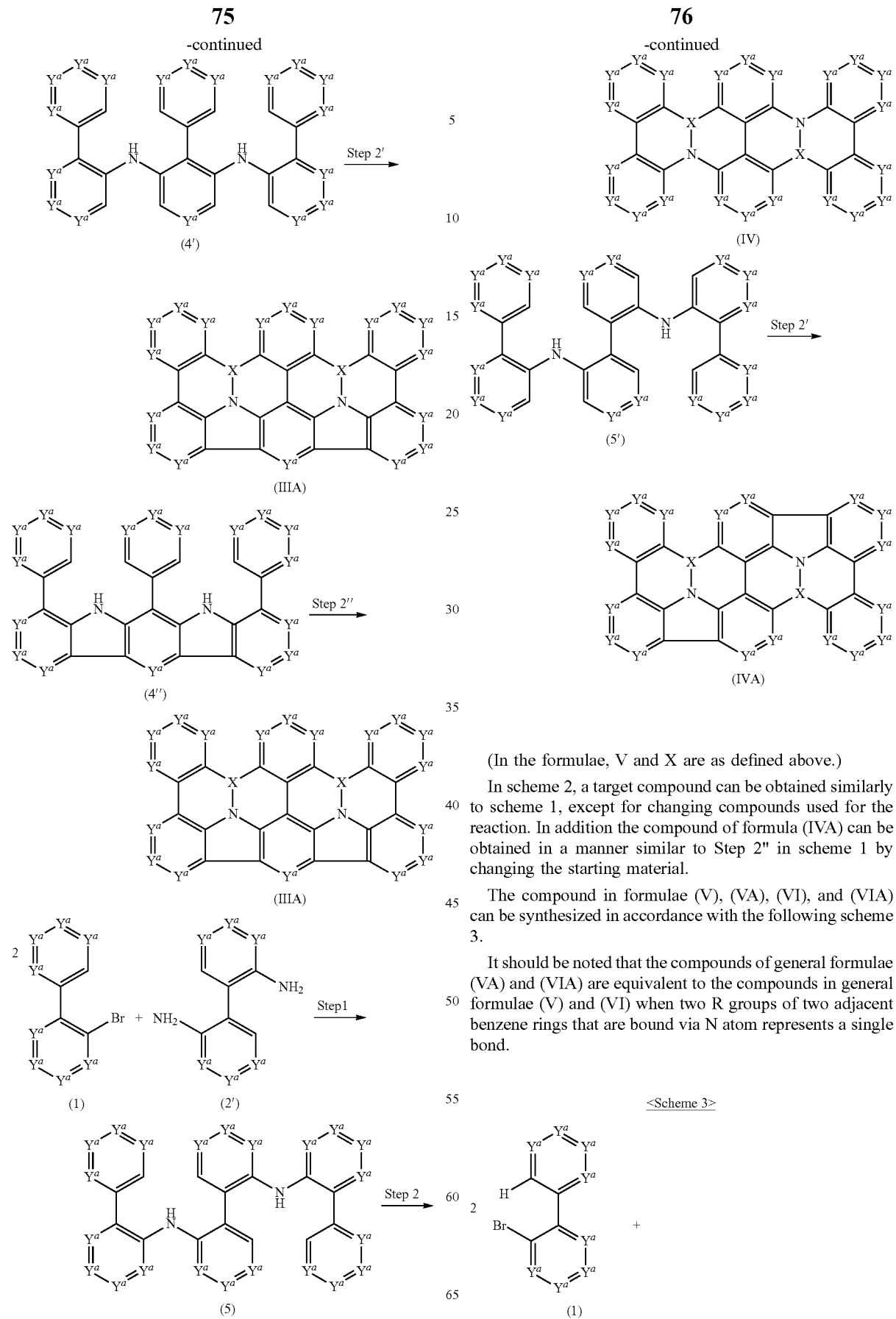

(In the formulae, V and X are as defined above.)

In scheme 2, a target compound can be obtained similarly to scheme 1, except for changing compounds used for the reaction. In addition the compound of formula (IVA) can be obtained in a manner similar to Step 2" in scheme 1 by changing the starting material.

The compound in formulae (V), (VA), (VI), and (VIA) can be synthesized in accordance with the following scheme 3.

It should be noted that the compounds of general formulae (VA) and (VIA) are equivalent to the compounds in general formulae (V) and (VI) when two R groups of two adjacent benzene rings that are bound via N atom represents a single bond.

<Scheme 3>

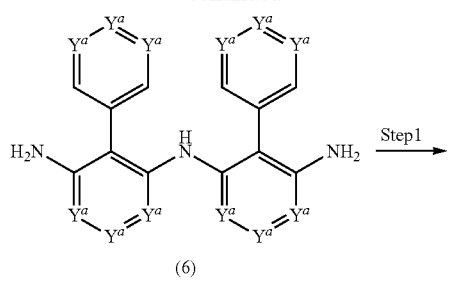
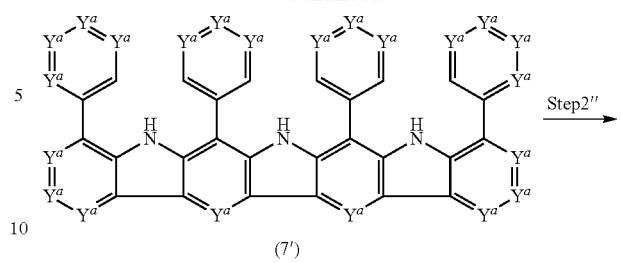
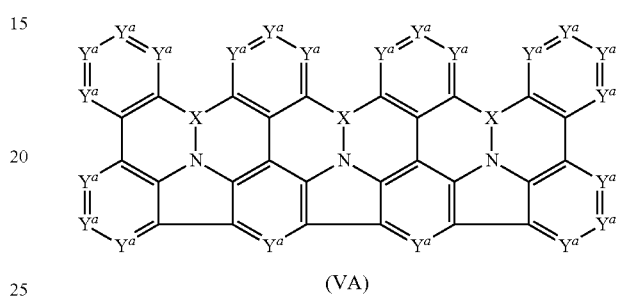
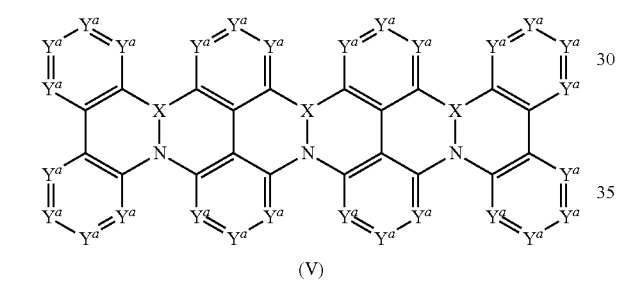
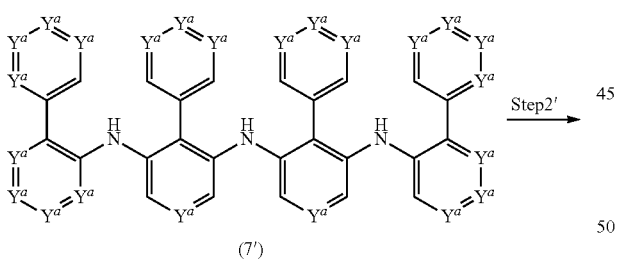
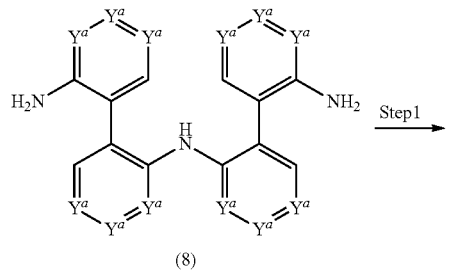
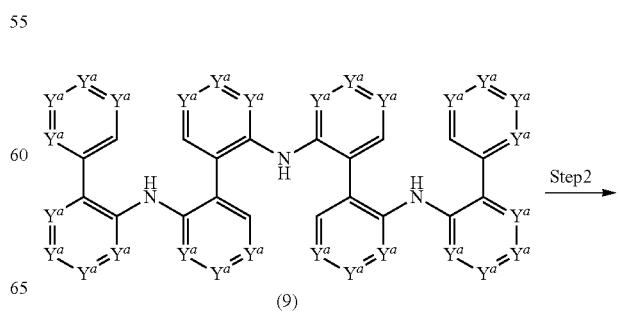

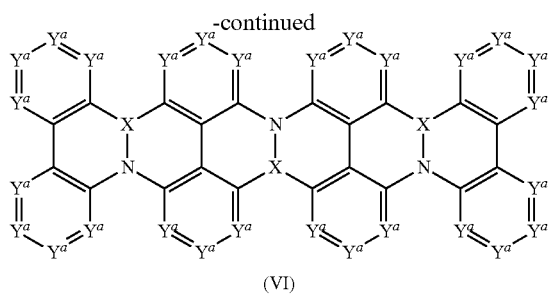
(VI)

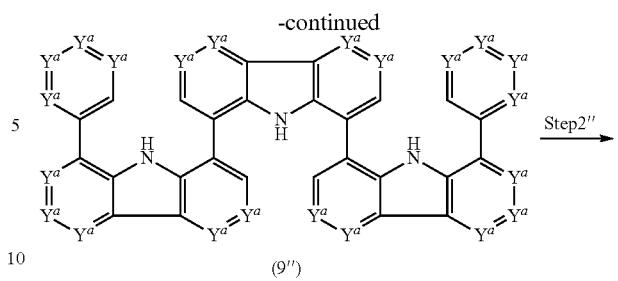
(9″)

Step2″ →

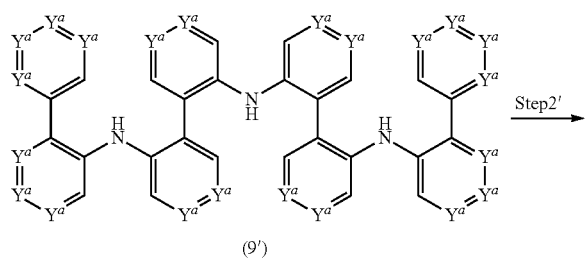
(9′)

Step2′ →

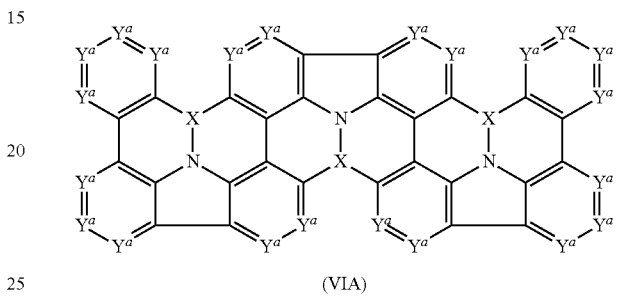
(VIA)

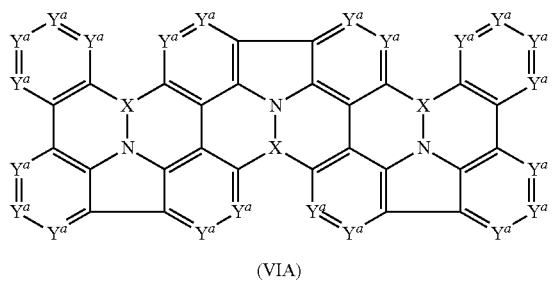
(VIA)

(In the formulae, R and X are as defined above.)

Scheme 3 can be conducted similarly to scheme 1, except for changing compounds used for the reaction.

The compounds of formulae (VII), (VIIA), (VIII), and (VIIIA) can be synthesized in accordance with the following scheme 4. It should be noted that the compounds in general formulae (VIIA) and (VIIIA) are equivalent to the compounds in general formulae (VII) and (VIII) when two R groups of two adjacent benzene rings that are bound via N atom represents a single bond.

<Scheme 4>

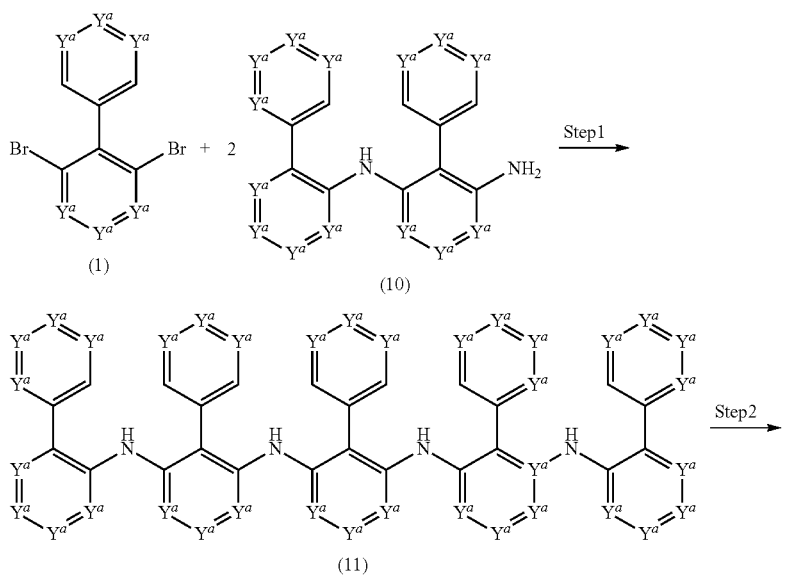

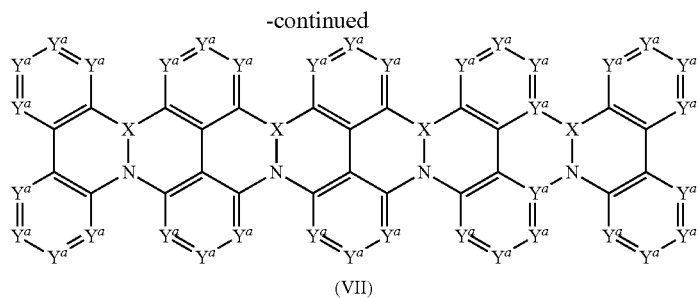
(VII)
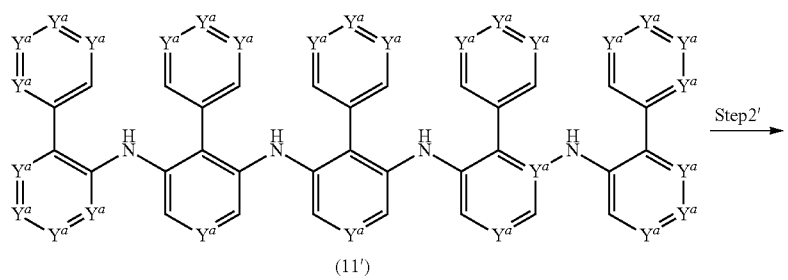
(11') →Step2'
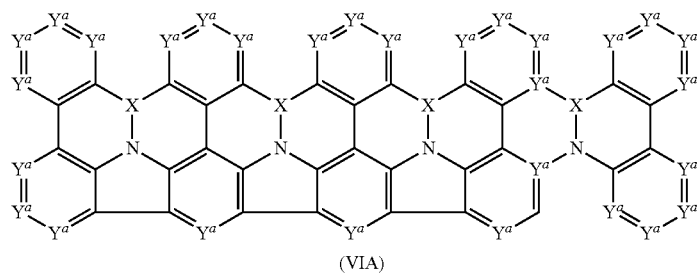
(VIA)
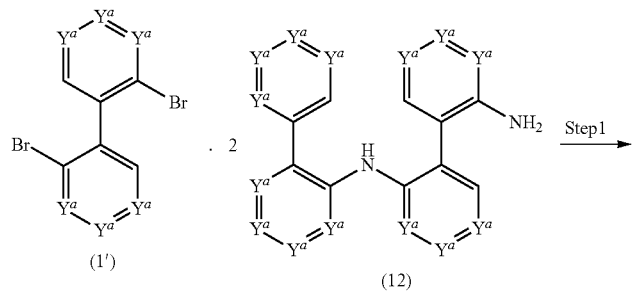
(1')   (12) →Step1
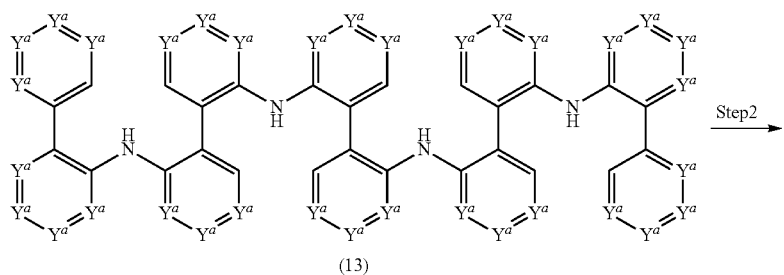
(13) →Step2

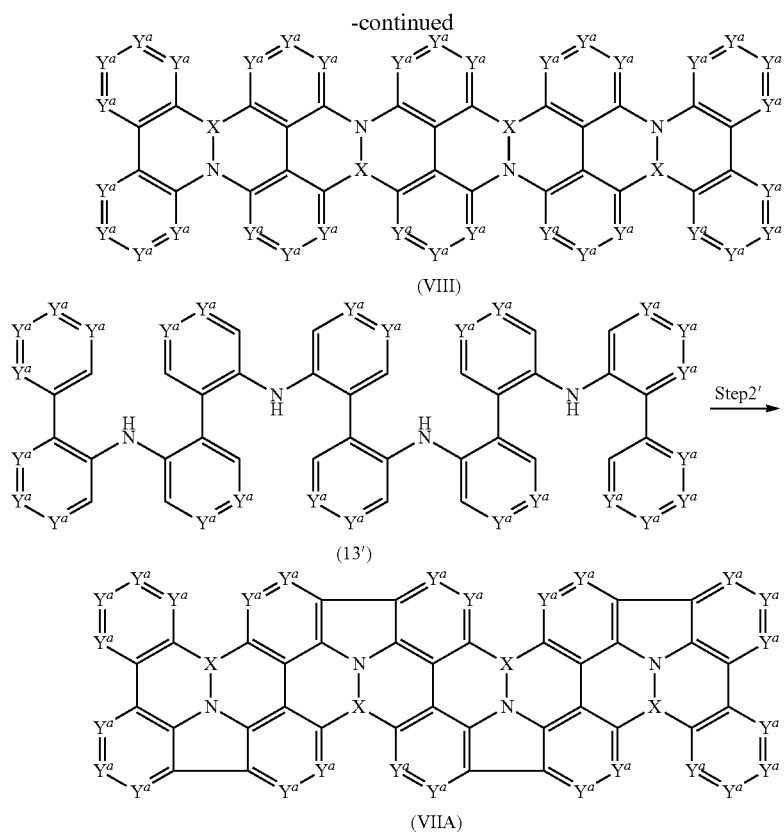

(In the formulae, V and X are as defined above.)

Scheme 4 can be conducted similarly to scheme 1, except for changing compounds used for the reaction. Furthermore, the compounds of formulae (VIIA) and (VIIIA) can be obtained in a manner similar to Step 2″ in scheme 1 by changing the starting material.

The compounds of formulae (IX), (IXA), (X), and (XA) can be synthesized in accordance with the following scheme 5.

It should be noted that the compounds in general formulae (IXA) and (XA) are equivalent to the compounds in general formulae (IX) and (X) when two R groups of two adjacent benzene rings that are bound via N atom represents a single bond.

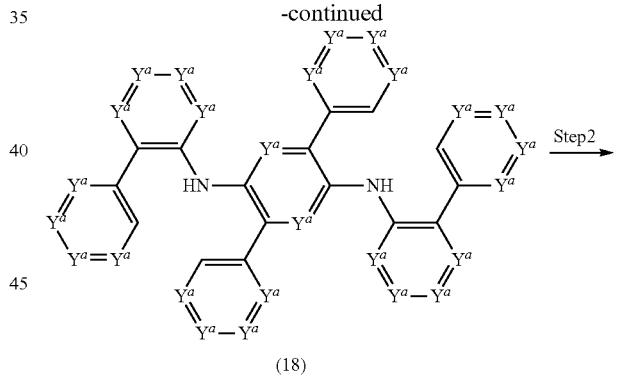

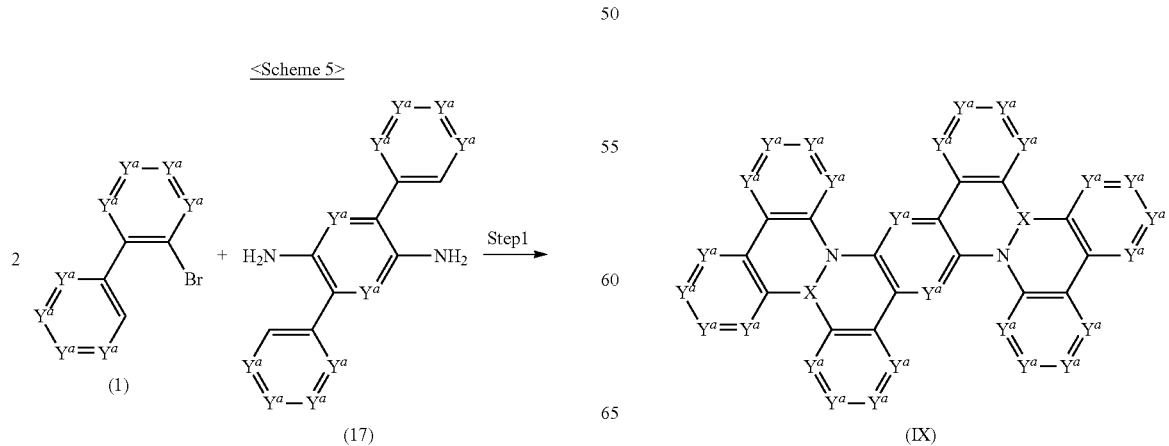

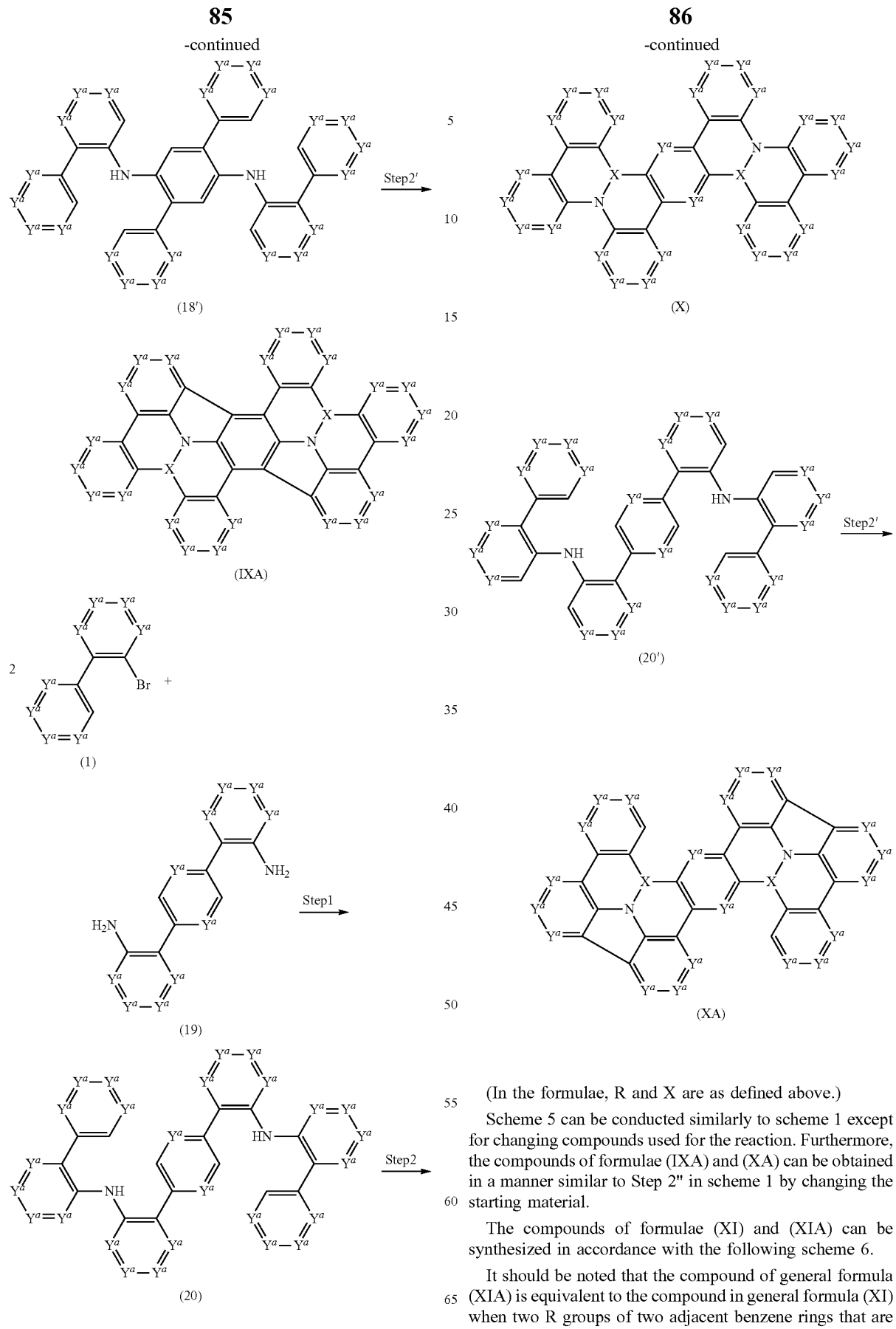

(In the formulae, R and X are as defined above.)

Scheme 5 can be conducted similarly to scheme 1 except for changing compounds used for the reaction. Furthermore, the compounds of formulae (IXA) and (XA) can be obtained in a manner similar to Step 2" in scheme 1 by changing the starting material.

The compounds of formulae (XI) and (XIA) can be synthesized in accordance with the following scheme 6.

It should be noted that the compound of general formula (XIA) is equivalent to the compound in general formula (XI) when two R groups of two adjacent benzene rings that are bound via N atom represents a single bond.

<Scheme 6>

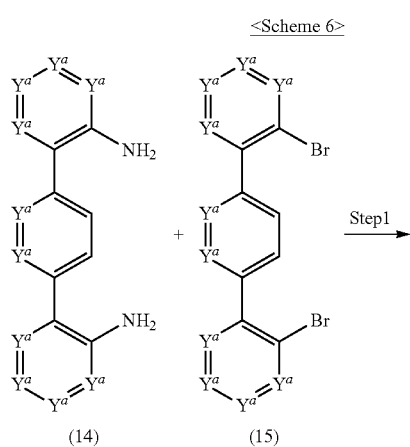

(14)    (15)

Step 1 →

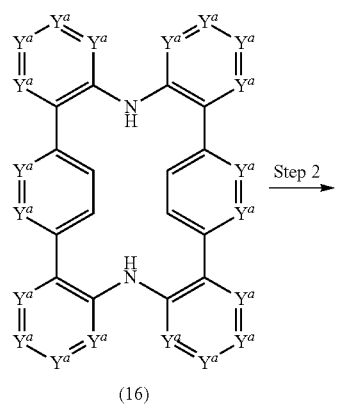

(16)

Step 2 →

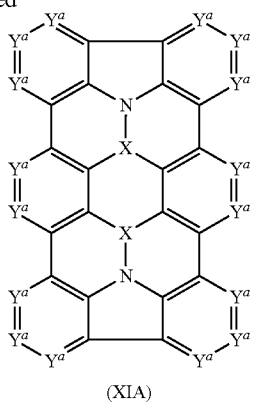

(XI)

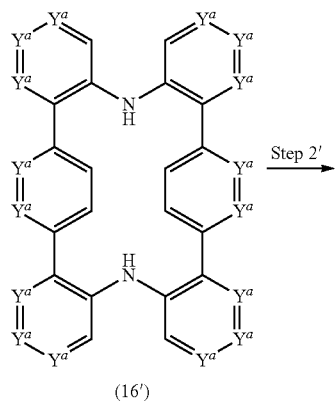

(16')

Step 2' →

-continued

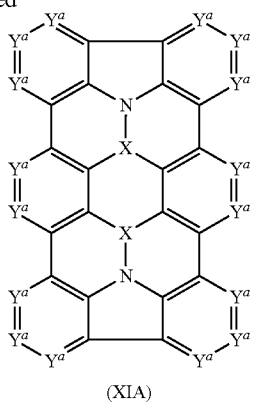

(XIA)

(In the formulae, R and X are as defined above.)

Scheme 6 can be conducted similarly to scheme 1, except for changing compounds used for the reaction. Furthermore, the compound of formula (XIA) can be obtained in a manner similar to Step 2" in scheme 1 by changing the starting material.

The compounds of formulae (XII) and (XIIA) can be synthesized in accordance with the following scheme 7. It should be noted that the compound of general formula (XIIA) is equivalent to the compound in general formula (XII) when two R groups of two adjacent benzene rings that are bound via N atom represents a single bond.

<Scheme 7>

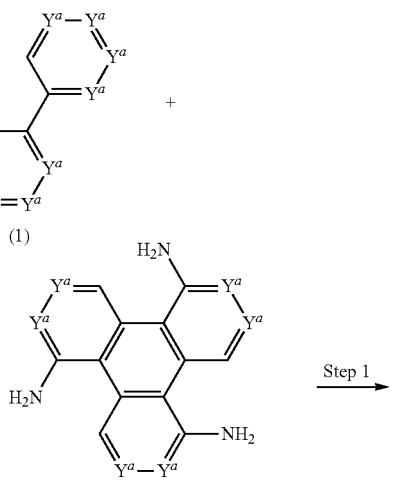

(1)

(21)

Step 1 →

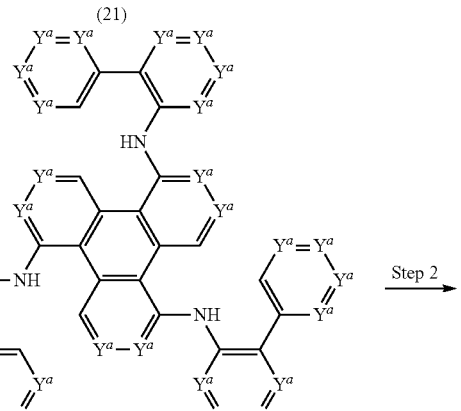

(22)

Step 2 →

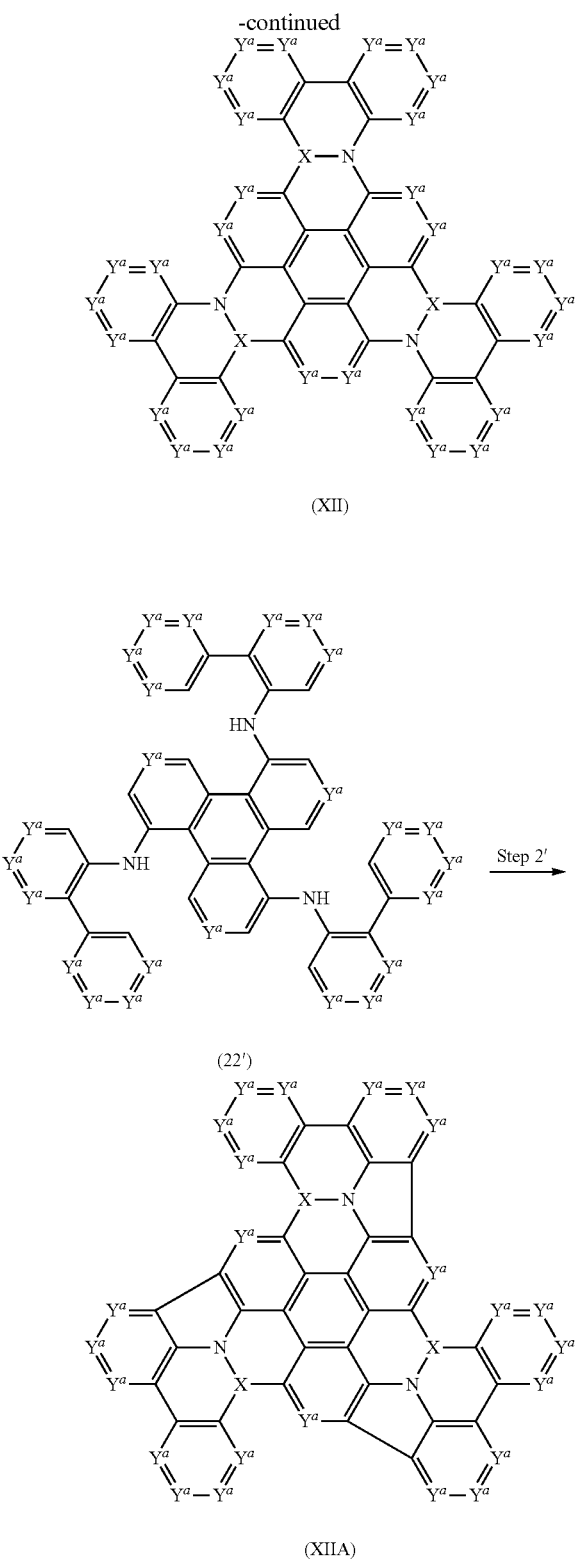

(XII)

(22')

(XIIA)

(In the formulae, V and X are as defined above.)

Scheme 7 can be conducted similarly to scheme 1, except for changing compounds used for the reaction. Furthermore, the compound of formula (XIIA) can be obtained in a manner similar to Step 2'' in scheme 1 by changing the starting material.

The compounds of formulae (XIII), (XIIIA), (XIV), and (XIVA) can be synthesized in accordance with the following scheme 8. It should be noted that the compounds of general formulae (XIIIA) and (XIVA) are equivalent to the compounds of general formulae (XIII) and (XIV) when two R groups of two adjacent benzene rings that are bound via N atom represents a single bond.

<Scheme 8>

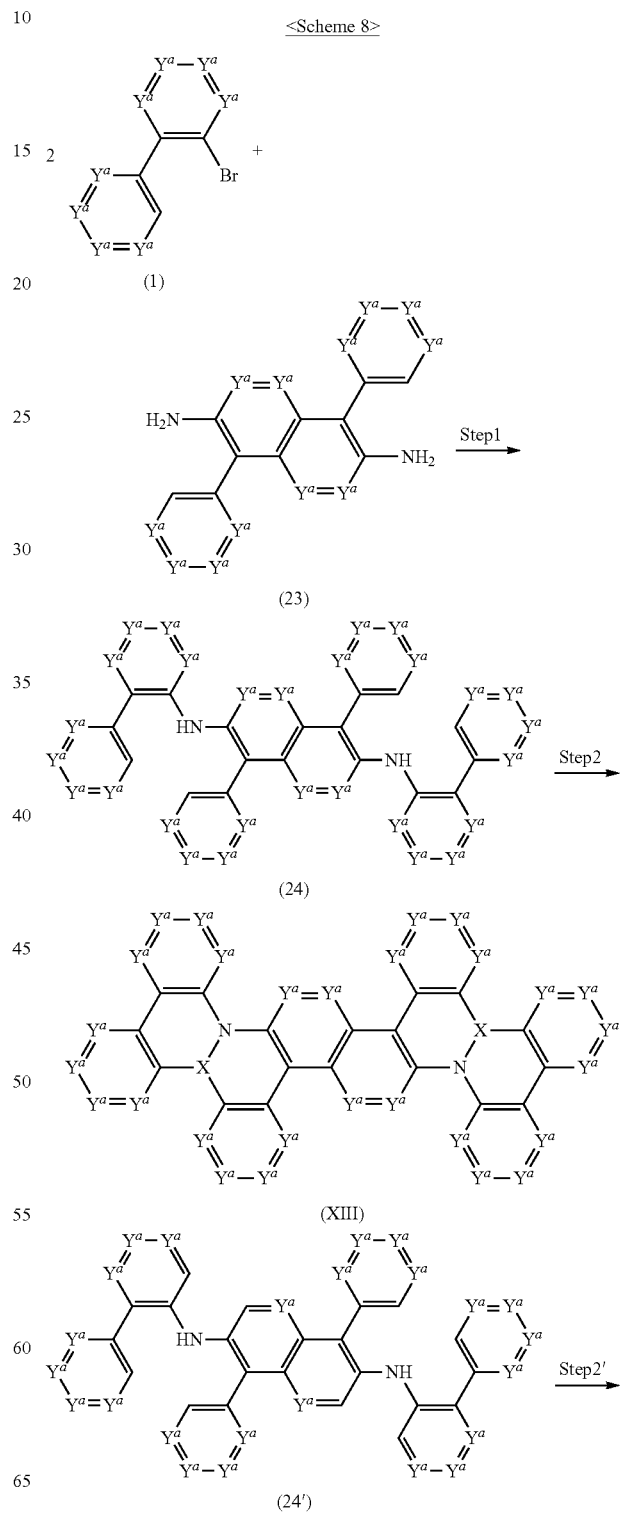

-continued

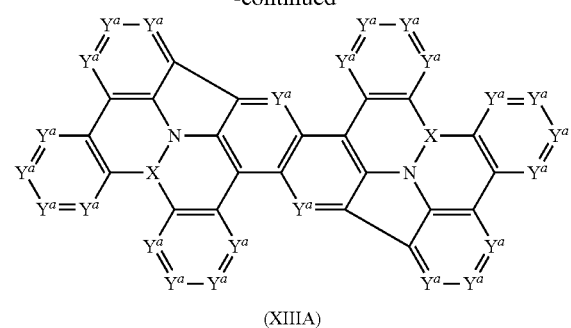

(XIIIA)

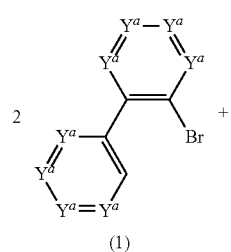

(1)

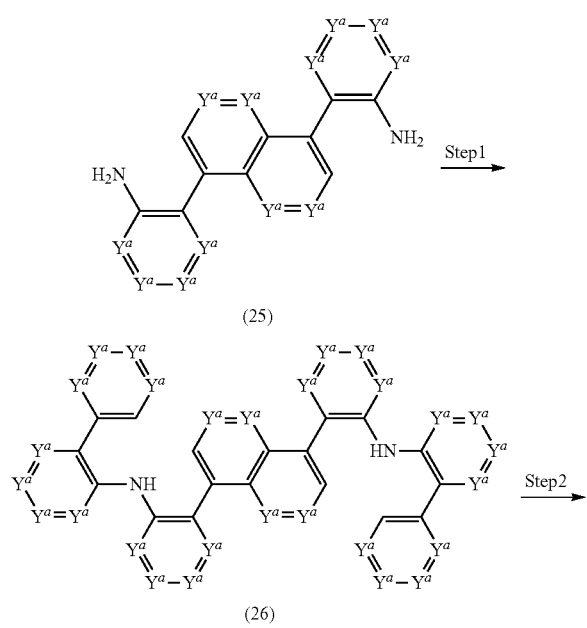

(XIV)

-continued

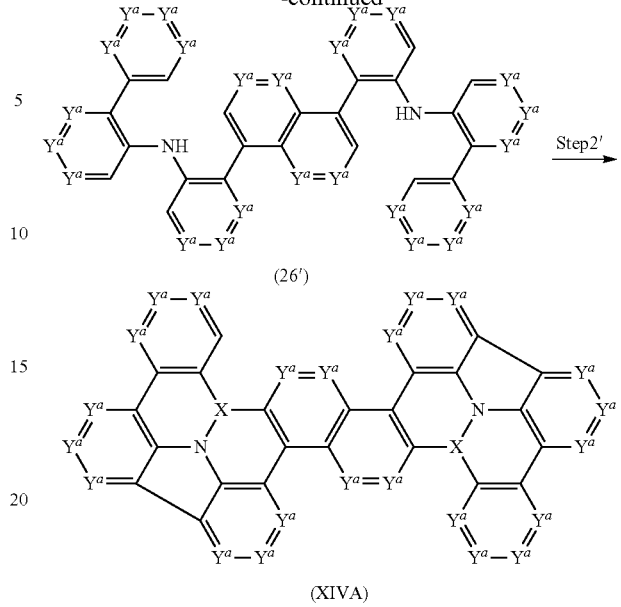

(XIVA)

(In the formulae, V and X are as defined above.)

Scheme 8 can be conducted similarly to scheme 1, except for changing compounds used for the reaction. Furthermore, the compounds of formulae (XIIIA) and (XIVA) can be obtained in a manner similar to Step 2" in scheme 1 by changing the starting material.

Conversion of P=S, P, and P=O at X can be performed in accordance with the following scheme 9. Conversion of P=S, P, and P=O can be performed for other compounds of the present invention in a similar manner.

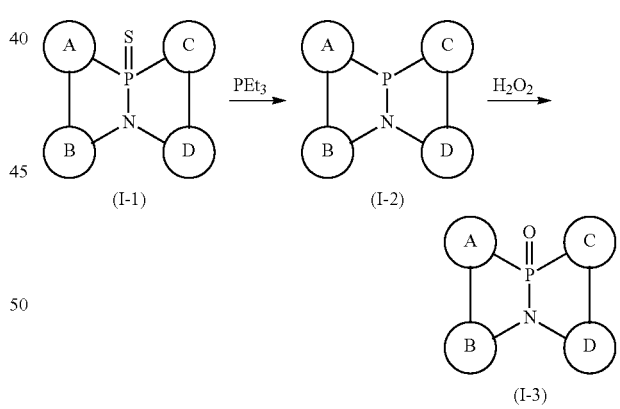

Next, an organic light-emitting element will be described in detail.

The organic light-emitting element of the present invention includes at least one pair of electrodes including a positive electrode and a negative electrode, and a layer including at least one layer containing an organic compound sandwiched between the one pair of electrodes, wherein the at least one layer of the layer containing the organic compound includes at least one type of a compound having a partial structure represented by general formula (I).

In one preferable embodiment, the organic light-emitting element of the present invention may include at least one type of the compound as a luminous layer of the layer containing the organic compound. Furthermore, in the case of an organic light-emitting element in which the luminous layer contains two or more compounds of a host and a guest, the host or the guest is preferably the compound described above. It should be noted that the guest in the present invention is a compound that emits light in response to recombination of a positive hole and an electron in an luminous area of the organic EL element, and is included in the substance (host) forming the luminous area.

In another embodiment, since the compound of the present invention has high charge mobility, the compound can be blended in a positive hole transportation layer as a positive hole transporting material, and can also be effectively used in an electron transporting layer as an electron transporting material.

The contained amount of the compound having the partial structure represented by general formula (I) according to the present invention is, when used as a guest, preferably not higher than 50 wt %, further preferably not lower than 0.1 wt % but not higher than 30 wt %, and particularly preferably not lower than 0.1 wt % but not higher than 15 wt %.

On the other hand, when the compound including the partial structure represented by general formula (I) according to the present invention is used as a host compound, the guest that is used is not particularly limited, and a later-described compound or the like can be appropriately used depending on the desired color of emitted light, etc. Furthermore, if necessary, other than the guest, a hole transportation compound, an electron transporting compound, and the like, can be doped together to be used.

Although the compound of the present invention may be used exclusively in a luminous layer as an organic compound layer, if necessary, the compound can be used in layers other than the luminous layer, such as, for example, a positive hole injection layer, a positive hole transportation layer, a positive hole barrier layer, an electron injection layer, an electron transporting layer, and an electronic barrier layer.

In the organic light-emitting element of the present invention, the compound having the partial structure represented by general formula (I) is formed between a positive electrode and a negative electrode using vacuum deposition method or solution coating method. The thickness of the organic layer is smaller than 10 µm, and is formed in a thin film having a thickness of preferably not larger than 0.5 µm, and more preferably not smaller than 0.01 but not larger than 0.5 µm.

In the organic light-emitting element of the present invention, the layer containing the compound having the partial structure represented by general formula (I) and a layer containing other organic compounds are generally formed into a thin film through a vacuum deposition method or a method of applying a coating of a compound dissolved in an appropriate solvent. In particular, when a film is formed using a coating method, the compound can be combined with an appropriate binder resin to be formed into a film.

The binder resin can be selected from a wide range of binding resins; and examples thereof include, but are not limited to, polyvinyl carbazole resin, polycarbonate resin, polyester resin, polyarylate resin, polystyrene resin, acrylic resin, methacrylic resin, butyral resin, polyvinyl acetal resin, diallyl phthalate resin, phenol resin, epoxy resin, silicone resin, polysulfone resin, urea resin, and the like. Furthermore, these resins may be used singly, or one or more types thereof may be mixed as a copolymer to be used.

As the positive electrode material, for example, an elemental metal such as gold, platinum, nickel, palladium, cobalt, selenium, and vanadium, an alloy thereof, and metal oxides such as tin oxide, zinc oxide, indium tin oxide (ITO), and indium zinc oxide can be used. In addition, a conductive polymer such as polyaniline, polypyrrole group, polythiophene, and polyphenylene sulfide can also be used. These electrode substances may be used singly, or in a combination of two or more.

As the negative electrode material, for example, elemental metals such as lithium, sodium, potassium, cesium, calcium, magnesium, aluminum, indium, silver, lead, tin, and chromium; and an alloy consisting of multiple metals can be used. It is also possible to use a metal oxide such as indium tin oxide (ITO). Furthermore, the negative electrode may have a single-layer configuration or a multilayered configuration.

The substrate used in the present invention is not particularly limited, and opaque substrates such as metallic substrates and ceramic substrates; and transparent substrates such as glass, quartz, and plastic sheets can be used. Furthermore, it is also possible to use a color filter film, a fluorescent color converting filter film, a dielectric reflection film, or the like, as the substrate for controlling colored light.

It should be noted that it is possible to provide the created element with a sealing layer or a protective layer for the purpose of preventing contact with oxygen, moisture, and the like. Examples of the protective layer include inorganic material films such as diamond thin films, metal oxides, and metal nitrides; polymer films such as fluororesin, polyparaxylene, polyethylene, silicone resins, and polystyrene resins; and photo-curable resins. Furthermore, it is also possible to provide a cover using glass, a gas-impermeable film, a metal, or the like, and package the element itself using an appropriate sealing resin.

The compound of the present invention can also be used as the organic semiconductor material, or in a composition for forming an organic semiconductor layer including the compound of the present invention and an organic solvent.

As the organic solvent, a common organic solvent can be used without any special limitation, and preferable examples thereof that can be used include: alcohols including methyl alcohol, ethyl alcohol, n-propyl alcohol, isopropyl alcohol, n-butyl alcohol, sec-butyl alcohol, t-butyl alcohol, isobutyl alcohol, and diacetone alcohol; ketones including acetone, methyl ethyl ketone, and methyl isobutyl ketone; glycols including ethylene glycol, diethylene glycol, triethylene glycol, propyleneglycol, butylene glycol, hexylene glycol, 1,3-propanediol, 1,4-butanediol, 1,2,4-butanetriol, 1,5-pentanediol, 1,2-hexanediol, and 1,6-hexanediol; glycol ethers including ethylene glycol monomethyl ether and triethylene glycol monoethyl ether; glycol ether acetates including propylene glycol monomethyl ether acetate (PGMEA); acetates including ethyl acetate, butoxyethoxy ethyl acetate, butyl carbitol acetate (BCA), and dihydroterpineol acetate (DHTA); terpineols; trimethyl pentanediol monoisobutyrate (TEXANOL); dichloroethene (DCE); chlorobenzene; and N-methyl-2-pyrrolidone (NMP). With regard to these organic solvents, a single type may be used by itself, or a combination of two or more types may be used.

The composition preferably includes about 0.1 to 10 wt % of the organic semiconductor material, and about 90 to 99.9 wt % of an organic solvent.

The present invention further provides an organic semiconductor thin film that can be formed using the semiconductor layer-forming composition. In this case, the thin film can be formed by coating a substrate with the semiconductor layer-forming composition of the present invention.

The substrate is not particularly limited, as long as it does not hinder the object of the present invention. Those skilled in the art can select an appropriate substrate depending on the use application, and examples thereof include: glass substrates; silicon wafers; ITO glass; quartz; silica coated substrates; alumina coated substrates; and plastic substrates such as polyethylene naphthalate, polyethylene terephthalate, polycarbonate, polyvinyl alcohol, polyacrylate, polyimide, polynorbornene, and polyethersulfone.

As the coating method, a common wet process performed at ordinary temperature can be used without limitations, and examples of those that can be used preferably include spin coating, dip coating, roll coating, screen coating, spray coating, spin casting, flow coating, screen printing, ink-jetting, drop casting, and the like.

Although the organic semiconductor thin film of the present invention may have a film thickness of about 300 to 2,000 angstrom, the film thickness is not limited thereto.

The organic semiconductor thin film according to the present invention can be produced using a simple wet process performed at ordinary temperature, and has excellent electrical characteristics satisfying both high charge mobility and low leakage current through improvement in intermolecular packing density. Therefore, the organic semiconductor thin film of the present invention can be applied effectively to various organic electronic devices.

The present invention further provides an electrochemical device including the organic semiconductor thin film as a semiconductor layer.

Examples of the electrochemical device include, but are not necessarily limited to, organic light-emitting elements, organic thin-film transistors, organic thin-film solar cells, polymer memories, capacitors, and the like. In this case, the organic semiconductor thin film can be applied in the device through a process commonly known in the art.

Among these electrochemical devices, the present invention particularly provides an organic thin-film transistor. The organic thin-film transistor of the present invention may include a substrate, a gate electrode, an organic insulation layer, a semiconductor layer, and source/drain electrodes; and, as the semiconductor layer, an organic semiconductor thin film formed from the organic semiconductor material according to the present invention.

The organic thin-film transistor of the present invention may have generally known structures of a bottom-contact type, a top-contact type, or a top-gate type; or may have a modified structure, as long as the object of the present invention is not hindered.

The substrate of the organic thin-film transistor of the present invention is not particularly limited, as long as it is a substrate that is commonly used. Specific examples thereof that can be used include glass substrates, silica substrates, and plastic substrates such as polyethylene naphthalate, polyethylene terephthalate, polycarbonate, polyvinyl alcohol group, polyacrylate, polyimide, polynorbonene, and polyethersulfone.

As the gate electrode, source and drain electrodes, a metal commonly used can be applied, and specific examples thereof include, but are not limited to, gold (Au), silver (Ag), aluminum (Al), nickel (Ni), indium tin oxide (ITO), molybdenum/tungsten (Mo/W), and the like. Although the thicknesses of the gate electrode, and source and drain electrodes are preferably in a range of about 500 to 2,000 Å, the thicknesses are not necessarily limited thereto.

As the insulation layer, an insulator that is commonly used and has a large dielectric constant can be used; specific examples thereof include, but are not limited to, a ferroelectric insulator selected from the group consisting of $Ba_{0.33}Sr_{0.66}TiO_3$ (BST), $Al_2O_3$, $Ta_2O_5$, $La_2O_5$, $Y_2O_3$, and $TiO_2$; an inorganic insulator selected from the group consisting of $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $Bi_4Ti_3O_{12}$, $SiO_2$, $SiN_x$, and AlON; or an organic insulator such as polyimide, benzocyclobutene (BCB), parylene, polyacrylate, polyvinyl alcohol, and polyvinyl phenol. Although the thickness of such insulation layers is preferably in the range of about 3000 Å to 1 μm, the thickness is not necessarily limited thereto.

The present invention further provides an organic thin-film solar cell.

The structure of the organic thin-film solar cell of the present invention is not particularly limited as long as there is a portion between one pair of electrodes containing the compound. Specific examples thereof include structures having the following configuration on a stable insulating substrate.

(1) Lower electrode/p-layer/n-layer/upper electrode
(2) Lower electrode/buffer layer/p-layer/n-layer/upper electrode
(3) Lower electrode/p-layer/n-layer/buffer layer/upper electrode
(4) Lower electrode/buffer layer/p-layer/n-layer/buffer layer/upper electrode
(5) Lower electrode/buffer layer/p-layer/i-layer (or a mixed layer of p-material and n-material)/n-layer/buffer layer/upper electrode
(6) Lower electrode/buffer layer/p-layer/n-layer/buffer layer/intermediate electrode/buffer layer/p-layer/n-layer/buffer layer/upper electrode
(7) Lower electrode/buffer layer/p-layer/i-layer (or a mixed layer of p-material and n-material)/n-layer/buffer layer/intermediate electrode/buffer layer/p-layer/i-layer (or a mixed layer of p-material and n-material)/n-layer/buffer layer/upper electrode In the organic thin-film solar cell of the present invention, the material of the present invention may be included in any member forming the cell. Furthermore, a member containing the material of the present invention may contain other additional components. As members and mixed materials not containing the material of the present invention, members and materials known in the art for usage in organic thin-film solar cells can be used.

Preferably, since the material of the present invention has high mobility, it is suitable as a material used in p-layer/i-layer/n-layer.

Preferably, the material of the present invention is used in p-layer/i-layer/n-layer of the element configurations (2) to (7).

In the following, description of each configuration member will be provided.

1. Lower Electrode, Upper Electrode

The material of the lower electrode and the upper electrode is not particularly limited, and a conductive material known in the art can be used. For example, as an electrode that is to be connected to p-layer, tin-doped indium oxide (ITO) and metals such as gold (Au), osmium (Os), and palladium (Pd) can be used; and, as an electrode that is to be connected to n-layer, metals such as silver (Ag), aluminum (Al), indium (In), calcium (Ca), platinum (Pt), and lithium (Li), two component metals such as Mg:Ag, Mg:In, and Al:Li, and the above-illustrated electrode materials to be connected to p-layer can be used.

It should be noted that, in order to obtain highly efficient photoelectric transfer characteristics, at least one surface of the solar cell is preferably sufficiently transparent with respect to sunlight spectra. A transparent electrode is formed using a conductive material known in the art with a method such as vapor deposition and sputtering to ensure a predetermined translucency. An electrode of a receiving surface preferably has a light transmittance of 10% or higher. In a preferable configuration of a pair of electrodes, one of the electrode parts includes a metal having a large work function, and the other includes a metal having a small work function.

2. p-Layer, n-Layer, i-Layer

As the n-material, a compound having a function as an electron acceptor is preferable. Examples thereof include: when the n-material is an organic compound, fullerene derivatives including C60 and C70, carbon nanotubes, perylene derivatives, polycyclic quinone, quinacridone, and the like; and, when the n-material is polymer based, CN-poly(phenylene-vinylene), MEH—CN-PPV, —CN group or $CF_3$ group containing polymers, poly(fluorene) derivatives, and the like. A material having high electron mobility is preferable. A material having small electron affinity is further preferable. When such material having small electron affinity is combined as n-layer, sufficient open-end voltage can be achieved.

When the n-material is an inorganic compound, examples thereof include inorganic semiconductor compounds having n-type characteristics. Specific examples thereof include compound semiconductors, doped semiconductors such as n-Si, GaAs, CdS, PbS, CdSe, InP, $Nb_2O_5$, $WO_3$, and $Fe_2O_3$, and conductive oxides including titanium oxides such as titanium dioxide ($TiO_2$), titanium monoxide (TiO), and titanium sesquioxide ($Ti_2O_3$), zinc oxide (ZnO), and tin oxide ($SnO_2$). These inorganic compounds may be used singly, or in a combination of two or more. A titanium oxide is preferably used, and titanium dioxide is particularly preferably used.

As the p-material, a compound having a function as a positive hole acceptor is preferable. Examples thereof include: when the p-material is an organic compound, amine compounds represented by N,N'-bis(3-tolyl)-N,N'-diphenyl-benzidine (mTPD), N,N'-dinaphthyl-N,N'-diphenylbenzidine (NPD), 4,4',4''-tris(phenyl-3-tolylamino)triphenylamine (MTDATA), and the like, phthalocyanines such as phthalocyanine (Pc), copper phthalocyanine (CuPc), zinc phthalocyanine (ZnPc), and titanyl phthalocyanine (TiOPc), and porphyrins represented by octaethylporphyrin (OEP), platinum octaethylporphyrin (PtOEP), zinc tetraphenylporphyrin (ZnTPP), and the like; and, when the p-material is a polymer compound, main chain-type conjugated polymers such as polyhexylthiophene (P3HT) and methoxyethylhexyloxy phenylenevinylene (MEHPPV), and side chain-type polymers represented by polyvinyl carbazole and the like.

When the material of the present invention is used in the i-layer, it is possible to form the i-layer by mixing the p-layer compound or the n-layer compound, or form the i-layer by the material of the present invention alone. In this case, any of the compounds illustrated above may be used in the p-layer or the n-layer.

3. Buffer Layer

Generally, since an organic thin-film solar cell often has a small overall film thickness, yield rate in manufacturing cells is often reduced due to short-circuiting between the upper electrode and the lower electrode. This is preferably prevented by laminating a buffer layer.

As a compound preferable for the buffer layer, a compound having sufficiently high carrier mobility for not lowering short-circuit current, even with a large film-thickness, is preferable. Examples thereof include bathocuproine (BCP), and aromatic cyclic anhydrides and the like represented by NTCDA described in the following when the compound for the buffer layer is a low-molecular-weight compound. When the compound for the buffer layer is a polymer compound, examples thereof include conductive polymers known in the art represented by poly(3,4-ethylenedioxy)thiophene:polystyrene sulfonate (PEDOT:PSS), polyaniline:camphorsulfonic acid (PANI:CSA), and the like.

The buffer layer may also be a layer having a role of preventing an exciton from diffusing to an electrode and becoming deactivated. The use of the buffer layer as an exciton blocking layer in such a manner is effective in order to achieve high efficiency. An exciton blocking layer can be inserted in both the positive electrode side and the negative electrode side. Furthermore, the layer can be provided adjacent to an intermediate layer. Examples of materials having such a role include materials having a large energy gap, such as BCP.

Other than those described above, as the buffer layer material, the inorganic semiconductor compounds illustrated above as a material of the n-layer can be used. As the inorganic semiconductor compound, CdTe, p-Si, SiC, GaAs, NiO, $WO_3$, $MoO_3$, $V_2O_5$, and the like, can be used.

4. Substrate

The substrate preferably has mechanical and thermal strength, and transparency. Examples thereof include glass substrates and transparent resin films. Examples of transparent resin films include polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyethersulfone, tetrafluoroethylene-perfluoroalkyl vinyl ether copolymer, polyvinyl fluoride, tetrafluoroethylene-ethylene copolymer, tetrafluoroethylene-hexafluoropropylene copolymer, polychlorotrifluoroethylene, polyvinylidene fluoride, polyester, polycarbonate, polyurethane, polyimide, polyether imide, polyimide, polypropylene, and the like.

5. Intermediate Electrode

When an intermediate electrode is placed in a laminated organic thin-film solar cell, it becomes possible to separate each photoelectric conversion unit in the laminated element since an electron-positive hole recombination zone is formed. This layer has a role of preventing the formation of reverse heterojunction between an n-layer in a forward photoelectric conversion unit and a p-layer in a backward photoelectric conversion unit. The layer between each of the photoelectric conversion units provides a zone for recombination of an electron entering from the forward photoelectric conversion unit and a positive hole from the backward photoelectric conversion unit. Efficient recombination of an electron entering from the forward photoelectric conversion unit and a positive hole from the backward photoelectric conversion unit is necessary when it is intended to generate photoinduced electric current in the laminated element.

The material that forms the electron-positive hole recombination zone created by the intermediate electrode is not particularly limited, and a material forming the upper electrode and the lower electrode can be used. Preferably, the electron-positive hole recombination zone created by the intermediate electrode includes a thin metal layer. The metal layer is preferably sufficiently thin and semi-transparent such that light can reach (multiple) photoelectric conversion unit(s) in the back.

For this purpose, the thickness of the metal layer is preferably thinner than about 20 Å. The thickness of the metal film is particularly preferably about 5 Å. It is thought that such extremely thin metal film (up to 5 Å) is formed not from a continuous film but from isolated metal nano particles. Surprisingly, although this extremely thin metal layer is not continuous, it is still effective as the electron-positive hole recombination layer. Metals that are preferable to be used for this layer include Ag, Li, LiF, Al, Ti, and Sn. Silver is a metal that is particularly preferable for this layer.

In order to form each layer of the laminated organic thin-film solar cell or the organic thin-film solar cell of the present invention, dry film-forming methods such as vacuum deposition, sputtering, plasma, and ion plating, and wet film-forming methods such as spin coating, dip coating, casting, roll coating, flow coating, and ink-jetting can be used.

The film thickness of each of the layers is not particularly limited, and is set at an appropriate film thickness. Since exciton diffusion length of an organic thin film is generally known to be small, when the film thickness is overly thick, an exciton becomes deactivated before reaching a hetero interface of a p-material and an n-material, resulting in low photoelectric conversion efficiency. When the film thickness is overly thin, a pinhole or the like may be generated and sufficient diode characteristics cannot be obtained, resulting in low conversion efficiency. Although an ordinary film thickness in the range of 1 nm to 10 μm is suitable, a film thickness in the range of 5 nm to 0.2 μm is further preferable.

When a dry film-forming method is to be used, a resistive heating method known in the art is preferable. When a mixed layer is to be formed, for example, a film-forming method by simultaneous vapor deposition from multiple deposition sources is preferable. Further preferably, the substrate temperature is controlled when forming a film.

When a wet film-forming method is to be used, the material forming each layer is dissolved or dispersed in an appropriate solvent to prepare a luminescent organic solution and form a thin film. Here, any solvent can be used. Examples thereof include halogenated hydrocarbon solvents such as dichloromethane, dichloroethane, chloroform, carbon tetrachloride, tetrachloroethane, trichloroethane, chlorobenzene, dichlorobenzene, and chlorotoluene; ether solvents such as dibutyl ether, tetrahydrofuran, dioxane, and anisole; alcohol solvents such as methanol, ethanol, propanol, butanol, pentanol, hexanol, cyclohexanol, methyl cellosolve, ethyl cellosolve, and ethylene glycol; hydrocarbon solvents such as benzene, toluene, xylene, ethylbenzene, hexane, octane, decane, and tetralin; and ester solvents such as ethyl acetate, butyl acetate, and amyl acetate. Among those described above, a hydrocarbon solvent or an ether solvent is preferable. In addition, these solvents may be used singly, or as a mixture of two or more. Furthermore, the solvent that can be used is not limited to those described above.

In the present invention, for any of the organic thin-film layers of the organic thin-film solar cell or the laminated organic thin-film solar cell, it is possible to use appropriate additives and resins for improving film-forming characteristics and preventing pinholes in films. Examples of resins that can be used include insulating resins such as polystyrene, polycarbonate, polyarylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole.

Furthermore, examples of additives include antioxidants, ultraviolet ray-absorbing agents, plasticizing agents, and the like.

EXAMPLES

The present invention is explained in further detail by Examples; however, the present invention is not limited thereto.

Example 1: Preparation of 4b-aza-12b-thiophosphadibenzo[g,p]chrysene

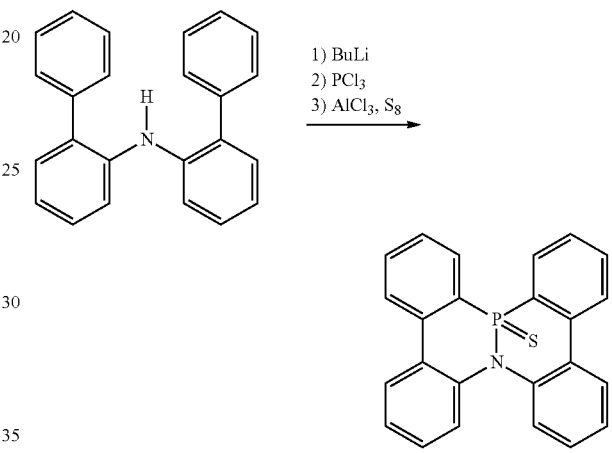

A hexane solution (6.13 mL, 1.63 M, 10.0 mmol) of butyllithium was added to bis(biphenyl-2-yl)amine (3.21 g, 10.0 mmol) and THF (50 mL) at −78° C. under an argon atmosphere, followed by stirring. One hour later, phosphorus trichloride (1.37 g, 10.0 mmol) was added thereto, and the mixture was stirred for one hour.

The mixture was warmed to 0° C. and further stirred for one hour. After distilling off the solvent under reduced pressure, 1,2-dichlorobenzene (80 mL) was added thereto.

Thereafter, aluminum trichloride (4.00 g, 30.0 mmol) and sulfur (0.481 g, 15.0 mmol) were added thereto, and the mixture was stirred at 120° C. for 18 hours.

1,4-Diazabicyclo[2.2.2.]octane (3.36 g, 30.0 mmol) was added thereto, and the mixture was subjected to filtration.

The crude product obtained by distilling off the solvent under reduced pressure was isolated by HPLC and GPC to obtain the title compound as a white powder (0.725 g, yield: 19%).

HRMS (EI) m/z; calcd. 381.0741[M]$^+$. found 381.0746.
$^1$H NMR (δppm in CD$_2$Cl$_2$ at −40° C.); 6.65 (d, 1H, J=8.4 Hz), 7.01 (t, 1H, J=7.2 Hz), 7.09 (t, 1H, J=7.8 Hz), 7.19 (dd, 1H, J=7.8, 13.8 Hz), 7.31 (td, 1H, J=3.0, 7.8 Hz), 7.54 (t, 1H, J=7.8 Hz), 7.62 (d, 1H, J=7.2 Hz), 7.65-7.69 (m, 2H), 7.75 (td, 1H, J=3.0, 7.8 Hz), 7.84-7.91 (m, 3H), 8.05 (d, 2H, J=7.2 Hz), 8.09 (t, 1H, J=7.2 Hz), 8.58 (dd, 1H, J=7.8, 15.6 Hz);
$^{13}$C NMR (δppm in CD$_2$Cl$_2$ at −40° C.); 118.1, 120.8, 121.2, 122.3, 124.4, 126.5, 128.1, 128.5, 128.6, 128.7, 128.9, 129.3, 130.2 (2C), 131.6, 132.1, 132.8, 132.9, 134.4, 134.5, 135.2, 135.3, 136.2, 141.5

Example 2: Preparation of 4b-aza-12b-phenyl-12b-siladibenzo[g,p]chrysene

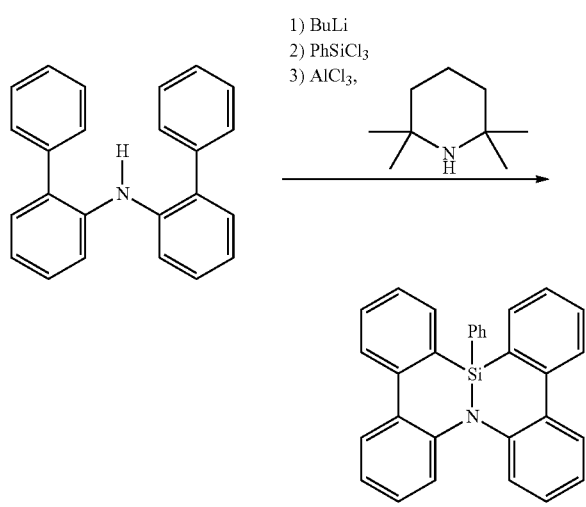

A hexane solution (0.62 mL, 1.60 M, 1.00 mmol) of butyllithium was added to bis(biphenyl-2-yl)amine (0.321 g, 1.00 mmol) and tetrahydrofuran (5 mL) at −78° C. under an argon atmosphere, followed by stirring. After one hour of stirring, phenyl trichlorosilane (0.212 g, 1.00 mmol) was added thereto at −78° C., and stirred at room temperature for 12 hours.

After distilling off the solvent under reduced pressure, 1,2-dichlorobenzene was added thereto.

Thereafter, aluminum trichloride (0.533 g, 4.00 mmol) and 2,2,6,6-tetramethylpiperidine (0.233 g, 1.50 mmol) were added thereto, and the mixture was stirred at 150° C. for 18 hours.

1,4-Diazabicyclo[2.2.2.]octane (0.449 g, 4.00 mmol) was added thereto, and the mixture was subjected to filtration.

The crude product obtained by distilling off the solvent under reduced pressure was isolated by HPLC and GPC to obtain the title compound as a white powder (0.064 g, yield: 15%). The title compound was recrystallized from hexane to obtain a colorless needle crystal, and the structure was determined by X-ray crystal structure analysis.

HRMS (FAB) m/z; calcd. 423.1443[M]+. found 423.1426.

The X-ray crystal structure is shown in FIG. 1.

Example 3: Preparation of 4b-aza-12b-germa-12b-phenyldibenzo[g,p]chrysene

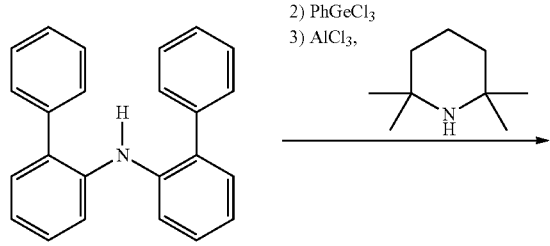

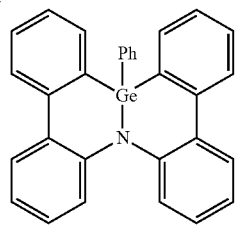

A hexane solution (1.25 mL, 1.60 M, 2.00 mmol) of butyllithium was added to bis(biphenyl-2-yl)amine (0.643 g, 2.00 mmol) and toluene (80 mL) at −78° C. under an argon atmosphere, followed by stirring. One hour later, the mixture was warmed to 0° C., and further stirred for one hour. Phenyl trichlorogermanium (0.512 g, 2.00 mmol) was then added at −78° C. and stirred at room temperature for 12 hours.

After distilling off the solvent under reduced pressure, 1,2-dichlorobenzene was added thereto.

Thereafter, aluminum trichloride (1.07 g, 8.00 mmol) and 2,2,6,6-tetramethylpiperidine (0.466 g, 3.00 mmol) were added thereto, and the mixture was stirred at 150° C. for 24 hours.

1,4-Diazabicyclo[2.2.2.]octane (1.12 g, 10.0 mmol) was added thereto, and the mixture was subjected to filtration.

The crude product obtained by distilling off the solvent under reduced pressure was isolated by HPLC and GPC to obtain the title compound as a white powder (0.389 g, yield: 42%). The title compound was recrystallized from hexane to obtain a colorless column crystal, and the structure was determined by X-ray crystal structure analysis.

HRMS (MALDI) m/z; calcd. 470.0964[M+H]+. found 470.0980.

The X-ray crystal structure is shown in FIG. 2.

Example 4: Preparation of 4b-aza-12b-boradibenzo[g,p]chrysene

Synthesis Example 1

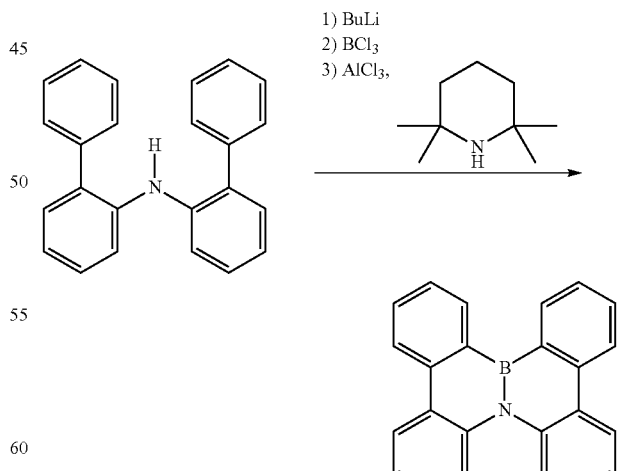

A hexane solution (9.35 mL, 1.60 M, 15.0 mmol) of butyllithium was added to bis(biphenyl-2-yl)amine (4.82 g, 15.0 mmol) and toluene (80 mL) at −78° C. under an argon atmosphere, followed by stirring.

One hour later, the mixture was warmed to 0° C. and further stirred for one hour.

A heptane solution (15.0 mL, 1.00 M, 15.0 mmol) of boron trichloride was added at −78° C. and stirred at room temperature for 12 hours.

After distilling off the solvent under reduced pressure, 1,2-dichlorobenzene was added thereto.

Thereafter, aluminum trichloride (8.00 g, 60.0 mmol) and 2,2,6,6-tetramethylpiperidine (3.49 g, 22.5 mmol) were added thereto, and the mixture was stirred at 150° C. for 12 hours.

1,4-Diazabicyclo[2.2.2.]octane (6.73 g, 60.0 mmol) was added thereto, and the mixture was subjected to filtration.

The crude product obtained by distilling off the solvent under reduced pressure was isolated by HPLC and GPC to obtain the title compound as a whitish yellow powder (3.31 g, yield: 67%).

Anal. calcd. for $C_{24}H_{16}NB$ C, 87.56; H, 4.90; N, 4.25. found C, 87.79; H, 5.14; N, 4.31.

HRMS (EI) m/z; calcd. 329.1376[M]+. found 329.1380.

$^1$H NMR (δppm in $CS_2/CD_2Cl_2$=2/1, 600 MHz); 7.26-7.34 (m, 4H, NCCHCHCH), 7.55 (td, J=1.2, 7.2 Hz, 2H, BCCHCH), 7.71 (td, J=1.2, 7.2 Hz, 2H, BCCCHCH), 8.04 (dd, J=1.8, 7.8 Hz, 2H, NCCH), 8.28 (dd, J=1.8, 7.8 Hz, 2H, NCCCH), 8.33 (d, J=7.8 Hz, 2H, BCCCH), 8.62 (dd, J=1.2, 7.2 Hz, 2H, BCCH); $^{13}$C NMR (δppm in $CS_2/CD_2Cl_2$=2/1, 151 MHz); 121.3 (2C), 123.1 (2C), 123.2 (2C), 125.6 (2C), 126.9 (4C), 127.6 (2C), 131.1 (2C), 132.6 (br, 2C, CBC), 135.6 (2C), 137.1 (2C), 138.8 (2C); $^{13}$B NMR (δppm in $CS_2/CD_2Cl_2$=2/1, 193 MHz); 35.6;

Synthesis Example 2

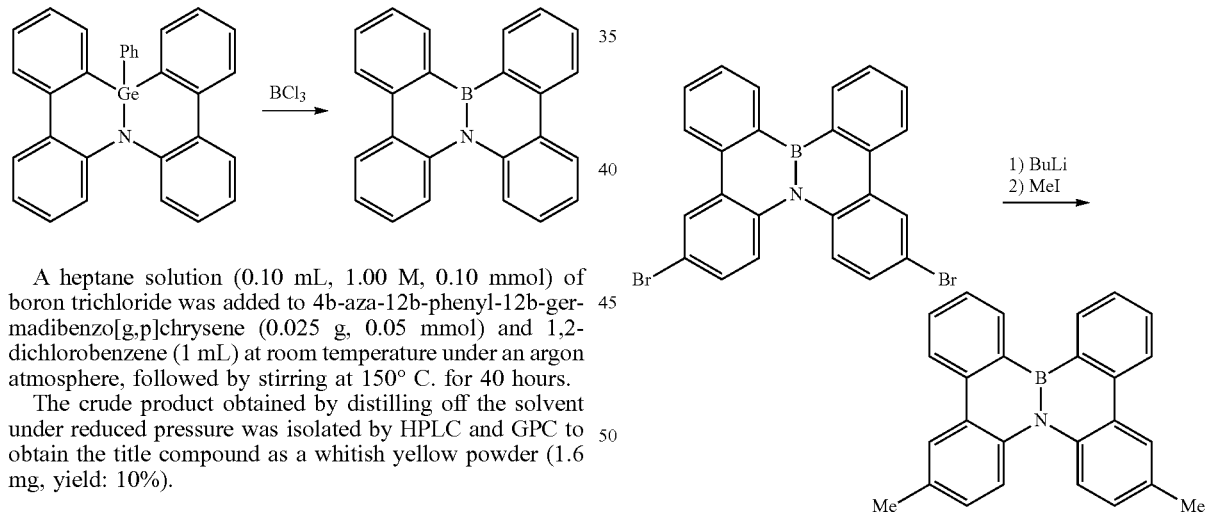

A heptane solution (0.10 mL, 1.00 M, 0.10 mmol) of boron trichloride was added to 4b-aza-12b-phenyl-12b-germadibenzo[g,p]chrysene (0.025 g, 0.05 mmol) and 1,2-dichlorobenzene (1 mL) at room temperature under an argon atmosphere, followed by stirring at 150° C. for 40 hours.

The crude product obtained by distilling off the solvent under reduced pressure was isolated by HPLC and GPC to obtain the title compound as a whitish yellow powder (1.6 mg, yield: 10%).

Example 5: Preparation of 2,7-dibromo-4b-aza-12b-boradibenzo[g,p]chrysene

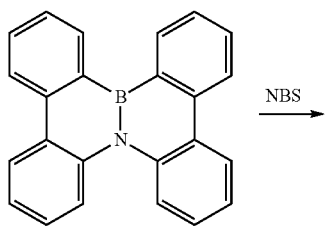 NBS

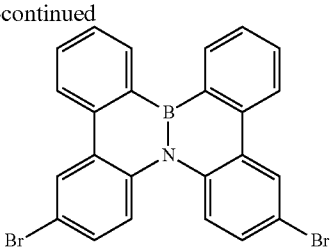

N-Bromosuccinimide (0.178 g, 1.00 mmol) was added to 4b-aza-12b-boradibenzo[g,p]chrysene (0.165 g, 0.50 mmol), methylene chloride (6.0 mL), and acetonitrile (2.0 mL) at room temperature, followed by stirring for one hour.

The crude product obtained by distilling off the solvent under reduced pressure was isolated by GPC to obtain the title compound as a whitish yellow powder (0.228 g, yield: 94%).

Anal. calcd. for $C_{24}H_{14}NBBr_2$° C., 59.19; H, 2.90; N, 2.88. found C, 59.13; H, 3.08; N, 2.93.

$^1$H NMR (δppm in $CDCl_3$, 392 MHz); 7.46 (dd, J=2.3, 9.0 Hz, 2H, NCCHCH), 7.65 (t, J=7.2 Hz, 2H, BCCHCH), 7.81 (t, J=7.2 Hz, 2H, BCCHCHCH), 7.89 (d, J=9.0 Hz, 2H, NCCH), 8.35 (d, J=7.6 Hz, 2H, BCCCH), 8.46 (d, J=2.3 Hz, 2H, NCCCH), 8.68 (d, J=7.6 Hz, 2H, BCCH); $^{13}$C NMR (δppm in $CDCl_3$, 98.5 MHz); 116.2 (2C), 122.8 (2C), 123.1 (2C), 127.6 (2C), 128.3 (2C), 129.5 (2C), 129.6 (2C), 131.5 (2C), 135.6 (2C), 135.7 (2C), 137.5 (2C).

Example 6: Preparation of 2,7-dimethyl-4b-aza-12b-boradibenzo[g,p]chrysene

A hexane solution (0.63 mL, 1.60 M, 1.00 mmol) of butyllithium was added to 2,7-dibromo-4b-aza-12b-boradibenzo[g,p]chrysene (0.243 g, 0.50 mmol) and toluene (5.0 mL) at −78° C. under an argon atmosphere, followed by stirring at 40° C. for 24 hours.

Thereafter, methyl iodide (0.178 g, 1.00 mmol) was added thereto, and the mixture was stirred for one hour.

The crude product obtained by distilling off the solvent under reduced pressure was isolated by GPC to obtain the title compound as a whitish yellow powder (0.228 g, yield: 20%).

HRMS (EI) m/z; calcd. 357.1689[M]+. found 357.1692.

$^{13}$B NMR (δppm in $C_6D_6$) 34.0.

Example 7: Preparation of 14b¹-aza-14b-borabenzo[p]indeno[1,2,3,4-defg]chrysene

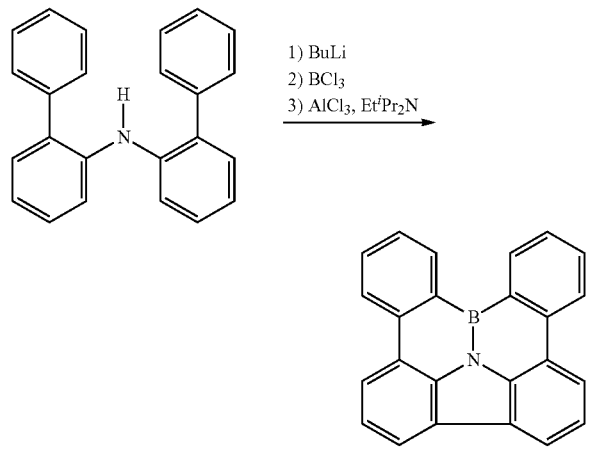

A hexane solution (1.23 mL, 1.60 M, 2.00 mmol) of butyllithium was added to bis(biphenyl-2-yl)amine (0.643 g, 2.00 mmol) and toluene (10 mL) at −78° C. under an argon atmosphere, followed by stirring.

One hour later, the mixture was warmed to 0° C. and further stirred for one hour.

A heptane solution (2.00 mL, 1.00 M, 2.00 mmol) of boron trichloride was added at −78° C. and stirred at room temperature for 12 hours.

After distilling off the solvent under reduced pressure, 1,2-dichlorobenzene (20 mL) was added thereto. Thereafter, aluminum trichloride (1.07 g, 8.00 mmol), and ethyldiisopropyl amine (0.258 g, 2.00 mmol) were added thereto, and the mixture was stirred at 180° C. for 12 hours.

1,4-Diazabicyclo[2.2.2.]octane (0.896 g, 8.00 mmol) was added thereto, and the mixture was subjected to filtration.

The crude product obtained by distilling off the solvent under reduced pressure was isolated by HPLC and GPC to obtain the title compound as a whitish yellow powder (0.255 g, yield: 39%).

HRMS (EI) m/z; calcd. 327.1219[M]⁺. found 327.1215.

¹H NMR (δppm in CDCl₃); 7.66-7.72 (m, 4H), 7.84 (td, 2H, J=1.4, 8.2 Hz), 8.21 (d, 2H, J=7.8 Hz), 8.43 (d, 2H, J=7.8 Hz), 8.67 (d, 2H, J=7.8 Hz), 9.18 (d, 2H, J=7.8 Hz).

Example 8: Preparation of 6,9-dichloro-14b¹-aza-14b-borabenzo[p]indeno[1,2,3,4-defg]chrysene

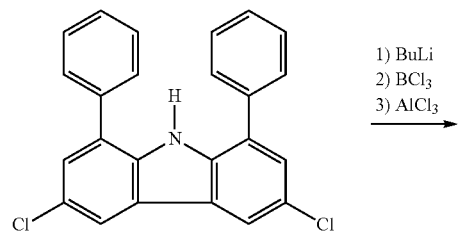

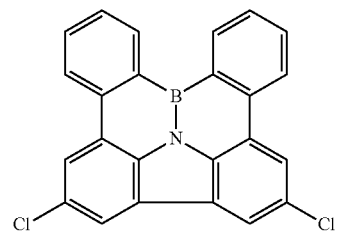

A hexane solution (1.56 mL, 1.60 M, 2.50 mmol) of butyllithium was added to 3,6-dichloro-1,8-diphenyl carbazole (0.971 g, 2.50 mmol) and toluene (10 mL) at −78° C. under an argon atmosphere, followed by stirring.

One hour later, the mixture was warmed to 0° C. and further stirred for one hour.

A heptane solution (2.50 mL, 1.00 M, 2.50 mmol) of boron trichloride was added at −78° C. and stirred at room temperature for 12 hours.

After distilling off the solvent under reduced pressure, 1,2-dichlorobenzene (50 mL) was added thereto.

Thereafter, aluminum trichloride (1.33 g, 10.0 mmol) was added thereto, and the mixture was stirred at 160° C. for 14 hours. 1,4-Diazabicyclo[2.2.2.]octane (1.12 g, 10.0 mmol) was added thereto, and the mixture was subjected to filtration.

The crude product obtained by distilling off the solvent under reduced pressure was isolated by HPLC and GPC to obtain the title compound as a yellowish brown powder (0.297 g, yield: 30%).

HRMS (EI) m/z; calcd. 395.0440[M]⁺. found 395.0426.

Example 9: Preparation of 4b-aza-12b-phosphadibenzo[g,p]chrysene

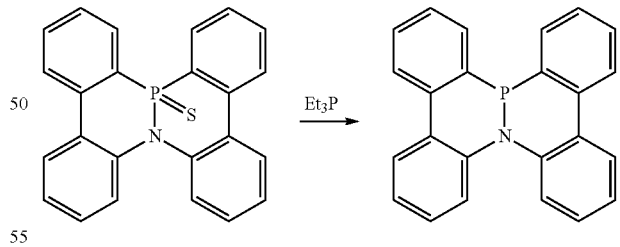

Chlorobenzene (3.0 mL) was added to 4b-aza-12b-thiophosphadibenzo[g,p]chrysene (0.114 g, 0.30 mmol) and triethylphosphine (0.039 g, 0.33 mmol) at 0° C. under an argon atmosphere, followed by stirring at 120° C. for 18 hours. The substance obtained by distilling off the solvent under reduced pressure was subjected to trituration using hexane to obtain the title compound as a white powder (0.073 g, yield: 70%).

HRMS (EI) m/z; calcd. 349.1020[M]⁺. found 349.1013.

³¹P NMR (δppm in C₆D₆) 12.7.

Example 10: Preparation of 4b-aza-12b-oxa-phosphadibenzo[g,p]chrysene

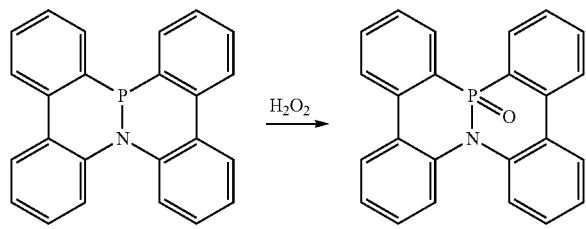

A 30% hydrogen peroxide solution (2.0 mL) was added to 4b-aza-12b-phosphadibenzo[g,p]chrysene (0.070 g, 0.20 mmol) and dichloromethane (2.0 mL), followed by stirring at room temperature for 6 hours.

The crude product obtained by distilling off the solvent of the extracted organic layer under reduced pressure was isolated by HPLC and GPC to obtain the title compound as a whitish yellow powder (0.066 g, yield: 90%).

HRMS (ESI) m/z; calcd. 366.1042[M+H]$^+$. found 366.1032. $^{31}$P NMR (δppm in $C_6D_6$) 6.6.

Example 11: Preparation of 8b,19b-diaza-11b,22b-dithio-phosphahexabenzo[a,c,fg,j,l,op]tetracene

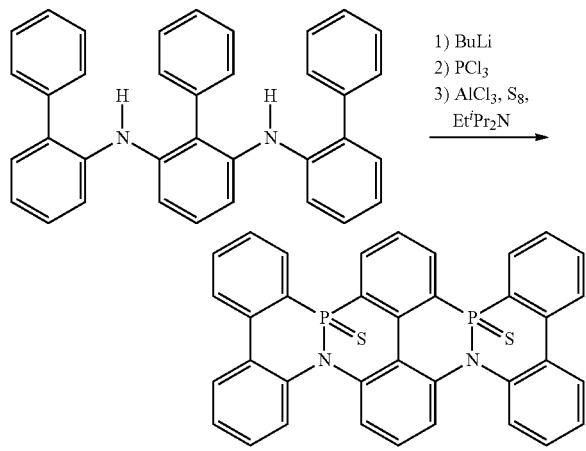

A hexane solution (2.45 mL, 1.63 M, 4.0 mmol) of butyllithium was added to N,N'-bis(biphenyl-2-yl)-2,6-diaminobiphenyl (0.977 g, 2.00 mmol) and toluene (20 mL) at −78° C. under an argon atmosphere, followed by stirring.

One hour later, phosphorus trichloride (0.549 g, 4.0 mmol) was added thereto, and the mixture was stirred for one hour.

The mixture was warmed to 0° C. and further stirred for one hour.

After distilling off the solvent under reduced pressure, 1,2-dichlorobenzene (40 mL) was added thereto.

Thereafter, aluminum trichloride (2.13 g, 16.0 mmol) and sulfur (0.192 g, 6.0 mmol) were added thereto, and the mixture was stirred at 120° C. for 18 hours.

1,4-Diazabicyclo[2.2.2.]octane (1.79 g, 16.0 mmol) was added thereto, and the mixture was subjected to filtration.

The crude product obtained by distilling off the solvent under reduced pressure was isolated by HPLC and GPC to obtain the title compound as a whitish yellow powder (0.122 g, yield: 10%).

HRMS (FAB) m/z; calcd. 609.0778[M+H]$^+$. found 609.0762.

Example 12: Preparation of 8b,19b-diaza-11b,22b-diborahexabenzo[a,c,fg,j,l,op]tetracene

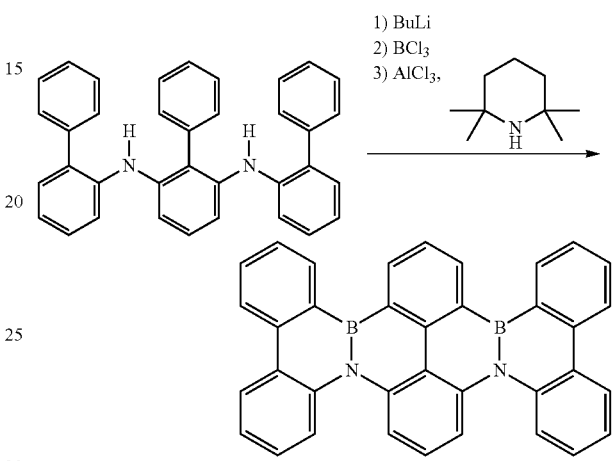

A hexane solution (2.45 mL, 1.63 M, 4.0 mmol) of butyllithium was added to N,N'-bis(biphenyl-2-yl)-2,6-diaminobiphenyl (0.977 g, 2.00 mmol) and toluene (20 mL) at −78° C. under an argon atmosphere, followed by stirring. One hour later, the mixture was warmed to 0° C. and further stirred for one hour.

A heptane solution (4.00 mL, 1.00 M, 4.0 mmol) of boron trichloride was added at −78° C. and stirred for one hour.

The mixture was warmed to room temperature and further stirred for 12 hours.

After distilling off the solvent under reduced pressure, 1,2-dichlorobenzene (40 mL) was added thereto.

Thereafter, aluminum trichloride (2.13 g, 16.0 mmol) and (0.192 g, 6.0 mmol) were added thereto, and the mixture was stirred at 150° C. for 24 hours. 1,4-Diazabicyclo[2.2.2.]octane (1.79 g, 16.0 mmol) was added thereto, and the mixture was subjected to filtration.

The crude product obtained by distilling off the solvent under reduced pressure was isolated by HPLC and GPC to obtain the title compound as a whitish yellow powder (0.122 g, yield: 40%).

Anal. calcd. for $C_{36}H_{22}N_2B_2C$, 85.76; H, 4.40; N, 5.56. found C, 85.85; H, 4.24; N, 5.66.

$^1$H NMR (δppm in $CS_2/CD_2Cl_2$=2/1, 600 MHz) 7.31-7.34 (m, 4H, NCCHCH), 7.55 (t, J=8.4 Hz, 1H, NCCHCHCN), 7.61 (td, J=1.2, 7.2 Hz, 2H, BCCHCHCHCH), 7.78 (td, J=1.2, 7.2 Hz, 2H, BCCHCHCHCH), 7.91 (t, J=7.2 Hz, 1H, BCCHCHCHCB), 8.05 (d, J=8.4 Hz, 2H, NCCHCHCN), 8.11-8.13 (m, 2H, NCCHCHCHCH), 8.32-8.35 (m, 2H, NCCCH), 8.40 (d, J=7.2 Hz, 2H, BCCCH), 8.71 (d, J=7.2 Hz, 2H, BCCHCHCHCH), 8.96 (d, J=7.2 Hz, 2H, BCCHCHCHCB); $^{13}$C NMR (δppm in $CS_2/CD_2Cl_2$=2/1, 151 MHz) 114.3 (2C), 119.2, 121.8 (2C), 123.1 (2C), 123.4 (2C), 125.7, 125.8 (2C), 126.2, 126.7 (2C), 127.1 (2C), 128.1 (2C), 130.5 (br, 2C, CBCCCBC), 131.4 (2C), 133.0

(br, 2C, CBCCCBC), 135.8 (2C), 137.5 (4C), 137.6 (2C), 138.9, 139.0 (2C); $^{11}$B NMR (δppm in CS$_2$/CD$_2$Cl$_2$=2/1, 193 MHz) 36.5.

Example 13: Preparation of 4b,17b-diaza-9b,22b-diboratetrabenzo[a,c,f,m]phenanthro[9,10-k]tetraphene

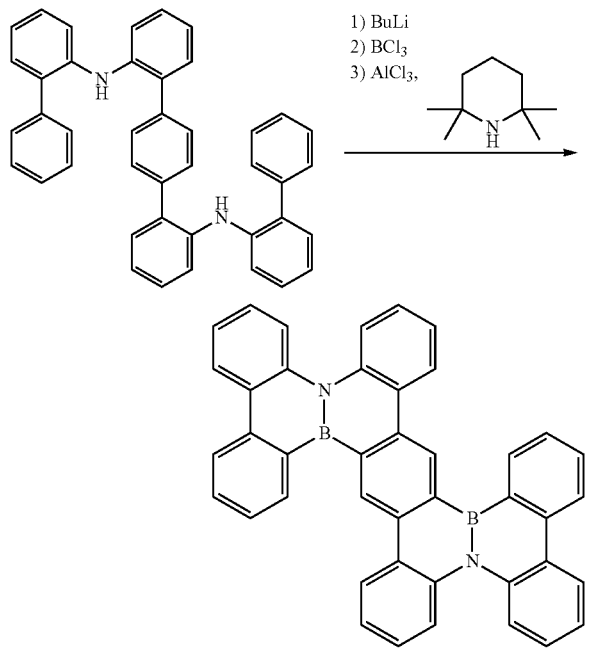

A hexane solution (0.62 mL, 1.63 M, 1.0 mmol) of butyllithium was added to N,N'-bis(biphenyl-2-yl)-2,2''-diamino terphenyl (0.565 g, 1.00 mmol) and toluene (10 mL) at −78° C. under an argon atmosphere, followed by stirring.

One hour later, the mixture was warmed to 0° C. and further stirred for one hour. A heptane solution (1.00 mL, 1.00 M, 1.0 mmol) of boron trichloride was added thereto at −78° C. and the mixture was stirred for one hour.

The mixture was then warmed to room temperature and further stirred for 12 hours.

After distilling off the solvent under reduced pressure, 1,2-dichlorobenzene (20 mL) was added thereto.

Thereafter, aluminum trichloride (2.13 g, 16.0 mmol) and (0.192 g, 6.00 mmol) were added thereto, and the mixture was stirred at 150° C. for 24 hours.

1,4-Diazabicyclo[2.2.2.]octane (1.79 g, 16.0 mmol) was added thereto, and the mixture was subjected to filtration.

The crude product obtained by distilling off the solvent under reduced pressure was isolated by HPLC and GPC to obtain the title compound as a whitish yellow powder (0.133 g, yield: 23%).

HRMS (FAB) m/z; calcd. 580.2282[M]$^+$. found 580.2296.

$^{13}$B NMR (δppm in CS$_2$/C$_6$D$_6$=2/1, 126 MHz) 35.7.

Example 14: Preparation of 11b-aza-3b-borabenzo[11,12]chryseno[6,5-b]thiophene

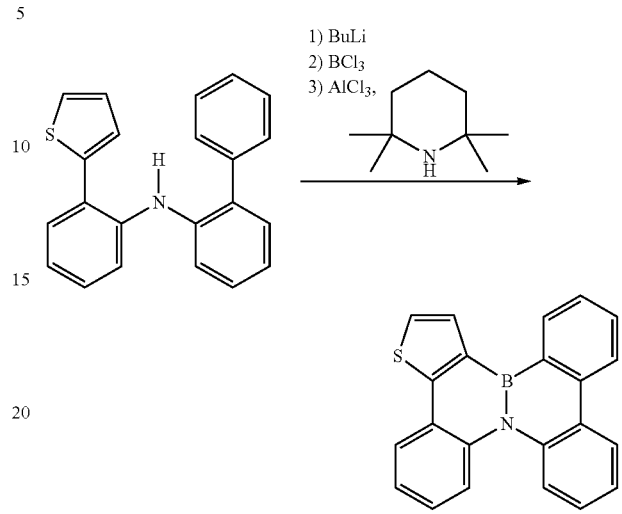

A hexane solution (1.25 mL, 1.60 M, 2.00 mmol) of butyllithium was added to N-[(2-thienyl)phenyl-]-N-(biphenyl-2-yl)amine (0.655 g, 2.00 mmol) and toluene (10 mL) at −78° C. under an argon atmosphere, followed by stirring.

One hour later, the mixture was warmed to 0° C. and further stirred for one hour.

A heptane solution (2.00 mL, 1.00 M, 2.00 mmol) of boron trichloride was added at −78° C. and stirred at room temperature for 12 hours.

After distilling off the solvent under reduced pressure, 1,2-dichlorobenzene (10 mL) was added thereto.

Thereafter, aluminum trichloride (1.07 g, 8.00 mmol) and 2,2,6,6-tetramethylpiperidine (0.621 g, 4.00 mmol) were added thereto, and the mixture was stirred at 150° C. for 24 hours.

1,4-Diazabicyclo[2.2.2.]octane (0.897 g, 8.00 mmol) was added thereto, and the mixture was subjected to filtration.

The crude product obtained by distilling off the solvent under reduced pressure was isolated by HPLC and GPC to obtain the title compound as a whitish yellow powder (0.054 g, yield: 8%).

HRMS (EI) m/z; calcd. 335.0940[M]$^+$. found 335.0926.

$^1$H NMR (δppm in C$_6$D$_6$, 392 MHz) 6.92-7.11 (m, 5H), 7.39 (td, J=0.9, 7.6 Hz, 1H), 7.50 (td, J=1.8, 7.2 Hz, 1H), 7.91-8.00 (m, 4H), 8.11-8.16 (m, 2H), 8.63 (dd, J=0.9, 7.6 Hz, 1H).

Example 15: Preparation of 11b-aza-3b-borabenzo[11,12]chryseno[5,6-b]thiophene

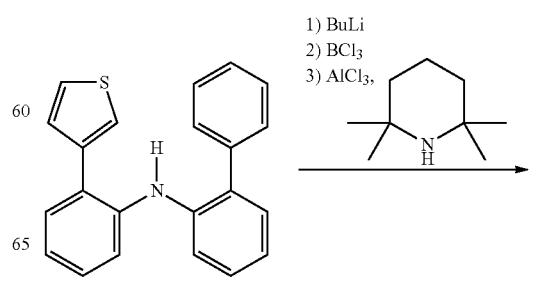

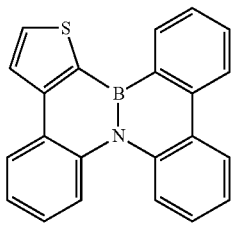

A hexane solution (1.25 mL, 1.60 M, 2.00 mmol) of butyllithium was added to N-[(3-thienyl)phenyl-]-N-(biphenyl-2-yl)amine (0.655 g, 2.00 mmol) and toluene (10 mL) at −78° C. under an argon atmosphere, followed by stirring.

One hour later, the mixture was warmed to 0° C. and further stirred for one hour.

A heptane solution (2.00 mL, 1.00 M, 2.00 mmol) of boron trichloride was added at −78° C. and stirred at room temperature for 12 hours.

After distilling off the solvent under reduced pressure, 1,2-dichlorobenzene (10 mL) was added thereto.

Thereafter, aluminum trichloride (1.07 g, 8.00 mmol) and 2,2,6,6-tetramethylpiperidine (0.621 g, 4.00 mmol) were added thereto, and the mixture was stirred at 150° C. for 24 hours.

1,4-Diazabicyclo[2.2.2.]octane (0.897 g, 8.00 mmol) was added thereto, and the mixture was subjected to filtration.

The crude product obtained by distilling off the solvent under reduced pressure was isolated by HPLC and GPC to obtain the title compound as a whitish yellow powder (0.020 g, yield: 3%).

HRMS (EI) m/z; calcd. 335.0940[M]+. found 335.0943.

$^1$H NMR (δppm in C$_6$D$_6$, 392 MHz) 7.00-7.05 (m, 2H), 7.07-7.12 (m, 2H), 7.40-7.50 (m, 3H), 7.63 (d, J=4.9 Hz, 1H), 7.94 (dd, J=1.8, 8.1 Hz, 1H), 8.03 (dd, J=1.3, 8.5 Hz, 1H), 8.08-8.15 (m, 3H), 8.95 (dd, J=1.4, 7.6 Hz, 1H).

Example 16: Preparation of 1-methyl-11b-aza-3b-borabenzo[11,12]chryseno[5,6-c]thiophene

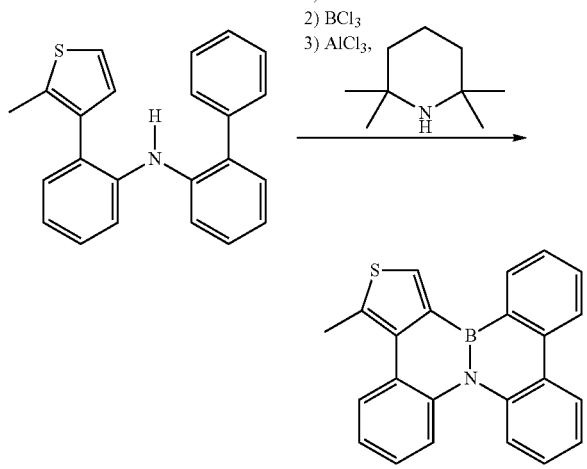

A hexane solution (1.25 mL, 1.60 M, 2.00 mmol) of butyllithium was added to N-[(3-(2-methyl)thienyl)phenyl]-N-(biphenyl-2-yl)amine (0.683 g, 2.00 mmol) and toluene (10 mL) at −78° C. under an argon atmosphere, followed by stirring.

One hour later, the mixture was warmed to 0° C. and further stirred for one hour.

A heptane solution (2.00 mL, 1.00 M, 2.00 mmol) of boron trichloride was added at −78° C. and stirred at room temperature for 12 hours.

After distilling off the solvent under a reduced pressure, 1,2-dichlorobenzene (10 mL) was added thereto.

Thereafter, aluminum trichloride (1.07 g, 8.00 mmol) and 2,2,6,6-tetramethylpiperidine (0.621 g, 4.00 mmol) were added thereto, and the mixture was stirred at 150° C. for 18 hours.

1,4-Diazabicyclo[2.2.2.]octane (0.897 g, 8.00 mmol) was added thereto and the mixture was subjected to filtration.

The crude product obtained by distilling off the solvent under reduced pressure was isolated by HPLC and GPC to obtain the title compound as a brown powder (0.035 g, yield: 5%).

HRMS (MALDI) m/z; calcd. 349.1091[M]+. found 349.1088.

$^{13}$B NMR (δppm in C$_6$D$_6$, 126 MHz) 32.5.

Example 17: Preparation of 3b-aza-11b-borabenzo[11,12]chryseno[6,5-b]thiophene

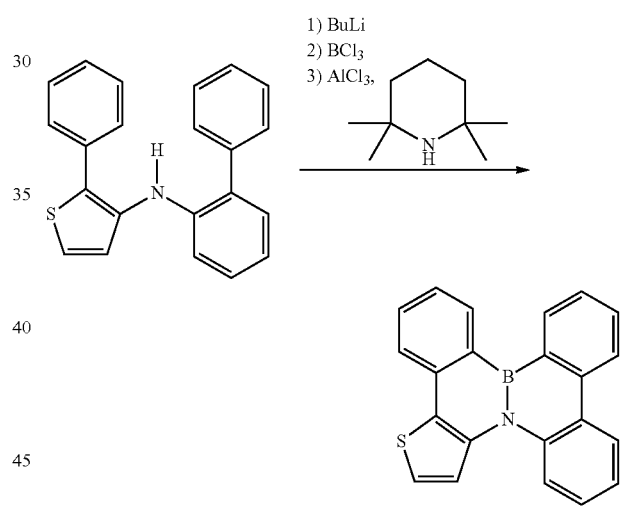

A hexane solution (1.25 mL, 1.60 M, 2.00 mmol) of butyllithium was added to N-([1,1'-biphenyl]-2-yl)-2-phenylthiophene-3-amine (0.655 g, 2.00 mmol) and toluene (10 mL) at −78° C. under an argon atmosphere, followed by stirring.

One hour later, the mixture was warmed to 0° C. and further stirred for another hour.

A heptane solution (2.00 mL, 1.00 M, 2.00 mmol) of boron trichloride was added at −78° C., and stirred at room temperature for 12 hours.

After distilling off the solvent under a reduced pressure, 1,2-dichlorobenzene (10 mL) was added thereto.

Thereafter, aluminum trichloride (1.07 g, 8.00 mmol) and 2,2,6,6-tetramethylpiperidine (0.621 g, 4.00 mmol) were added thereto, and the mixture was stirred at 150° C. for 24 hours.

1,4-Diazabicyclo[2.2.2.]octane (0.897 g, 8.0 mmol) was added thereto and the mixture was subjected to filtration.

The crude product obtained by distilling off the solvent under reduced pressure was isolated by HPLC and GPC to obtain the title compound as a whitish yellow powder (0.030 g, yield: 4%).

HRMS (EI) m/z; calcd. 335.0940[M]+. found 335.0929.

$^{11}$B NMR (δppm in $C_6D_6$, 126 MHz) 34.5.

Example 18: Preparation of 12b-aza-4b-boradibenzo[l,k]pyrrolo[1,2-f]phenanthridine

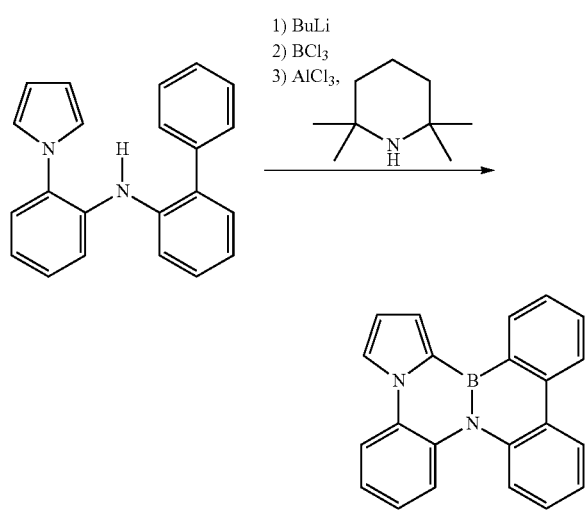

A hexane solution (1.25 mL, 1.60 M, 2.00 mmol) of butyllithium was added to N-(2-(1H-pyrrol-1-yl)phenyl)-[1,1'-biphenyl]-2-amine (0.621 g, 2.00 mmol) and toluene (10 mL) at −78° C. under an argon atmosphere, followed by stirring.

One hour later, the mixture was warmed to 0° C. and further stirred for one hour.

A heptane solution (2.00 mL, 1.00 M, 2.00 mmol) of boron trichloride was added at −78° C. and stirred at room temperature for 12 hours.

After distilling off the solvent under a reduced pressure, 1,2-dichlorobenzene (10 mL) was added thereto. Thereafter, aluminum trichloride (1.07 g, 8.00 mmol) and 2,2,6,6-tetramethylpiperidine (0.466 g, 3.00 mmol) were added and stirred at 150° C. for 24 hours.

1,4-Diazabicyclo[2.2.2.]octane (1.12 g, 10.0 mmol) was added thereto and the mixture was subjected to filtration.

The crude product obtained by distilling off the solvent under reduced pressure was isolated by HPLC and GPC to obtain the title compound as a white powder (0.023 g, yield: 4%).

HRMS (EI) m/z; calcd. 318.1328[M]+. found 318.1324.

$^1$H NMR (δppm in $C_6D_6$, 392 MHz) 6.72-6.73 (m, 1H), 6.76-6.80 (m, 1H), 6.85-6.89 (m, 1H), 7.01-7.09 (m, 2H), 7.28 (dd, J=1.3, 8.5 Hz, 1H), 7.35-7.39 (m, 1H), 7.46-7.51 (m, 2H), 7.55 (dd, J=1.3, 3.6 Hz, 1H), 7.80 (dd, J=1.3, 8.5 Hz, 1H), 7.86-7.89 (m, 1H), 8.09-8.13 (m, 2H), 8.71 (dd, J=1.3, 7.6 Hz, 1H).

Example 19: Preparation of 4b-aza-12b-borabenzo[f]phenanthro[9,10-h]quinoline

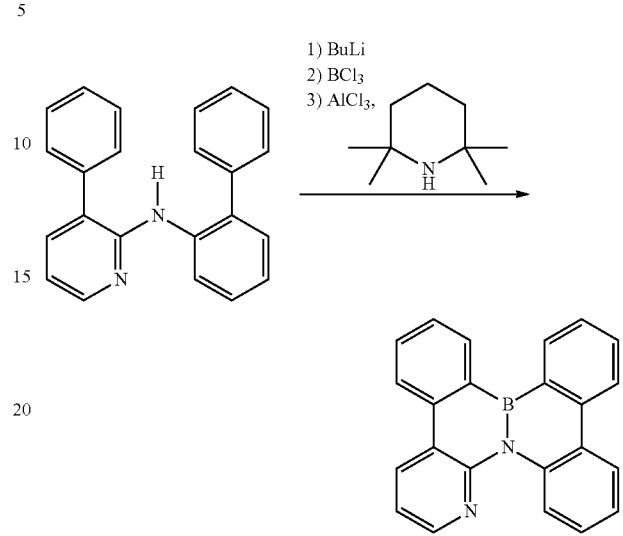

A hexane solution (1.25 mL, 1.60 M, 2.00 mmol) of butyllithium was added to N-([1,1'-biphenyl]-2-yl)-3-phenylpyridin-2-amine (0.645 g, 2.00 mmol) and toluene (10 mL) at −78° C. under an argon atmosphere, followed by stirring.

One hour later, the mixture was warmed to 0° C. and further stirred for one hour.

A heptane solution (2.00 mL, 1.00 M, 2.00 mmol) of boron trichloride was added at −78° C., and stirred at room temperature for 12 hours.

After distilling off the solvent under a reduced pressure, 1,2-dichlorobenzene (10 mL) was added thereto. Thereafter, aluminum trichloride (1.07 g, 8.00 mmol) and 2,2,6,6-tetramethylpiperidine (0.621 g, 4.00 mmol) were added thereto and stirred at 150° C. for 24 hours.

1,4-Diazabicyclo[2.2.2.]octane (0.897 g, 8.0 mmol) was added thereto and the mixture was subjected to filtration.

The crude product obtained by distilling off the solvent under reduced pressure was isolated by HPLC and GPC to obtain the title compound.

Example 20: Preparation of 4b-aza-12b-phenyl-12b-stannadibenzo[g,p]chrysene

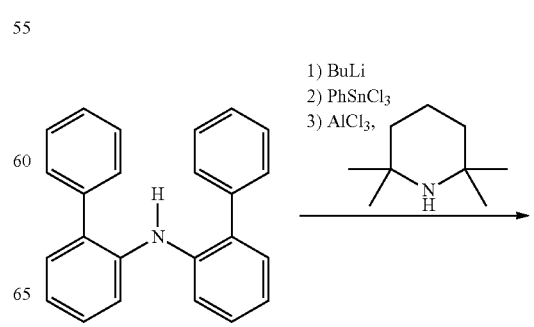

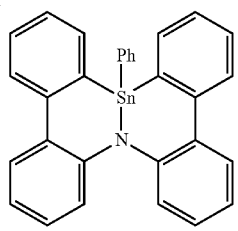

A hexane solution (0.63 mL, 1.60 M, 1.00 mmol) of butyllithium was added to bis(biphenyl-2-yl)amine (0.321 g, 1.00 mmol) and THF (10 mL) at −78° C. under an argon atmosphere, followed by stirring.

One hour later, phenyltrichlorostannane (0.302 g, 1.00 mmol) was added at −78° C. and stirred for one hour.

The mixture was further stirred at room temperature for 12 hours. After distilling off the solvent under a reduced pressure, 1,2-dichlorobenzene was added thereto.

Thereafter, aluminum trichloride (0.533 g, 4.00 mmol) and 2,2,6,6-tetramethylpiperidine (0.232 g, 1.50 mmol) were added thereto, and the mixture was stirred at 150° C. for 12 hours.

1,4-Diazabicyclo[2.2.2.]octane (0.448 g, 4.00 mmol) was added thereto and the mixture was subjected to filtration.

The crude product obtained by distilling off the solvent under reduced pressure was isolated by HPLC and GPC to obtain the title compound.

Example 21: Preparation of 6c-aza-16b-boradibenzo[c,p]naphtho[1,2-g]chrysene

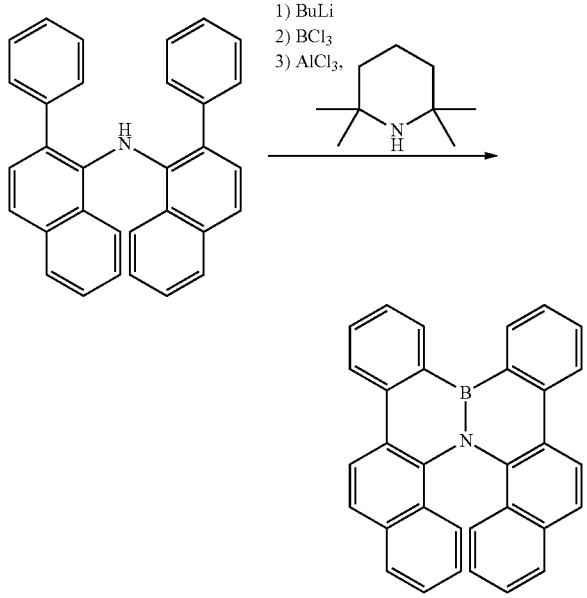

A hexane solution (8.75 mL, 1.60 M, 14.0 mmol) of butyllithium was added to bis(2-phenylnaphthalen-1-yl)amine (5.91 g, 14.0 mmol) and toluene (70 mL) at −78° C. under an argon atmosphere, followed by stirring. Five minutes later, the mixture was warmed to 0° C. and further stirred for 2 and a half hours.

Thereafter, a heptane solution (14.0 mL, 1.00 M, 14.0 mmol) of boron trichloride was added at −78° C. and stirred at room temperature for 12 hours.

After distilling off the solvent under a reduced pressure, 1,2-dichlorobenzene was added thereto.

Thereafter, aluminum trichloride (14.9 g, 112 mmol) and 2,2,6,6-tetramethylpiperidine (9.53 mL, 56.0 mmol) were added thereto and the mixture was stirred at 150° C. for 12 hours.

1,4-Diazabicyclo[2.2.2.]octane (12.6 g, 112 mmol) was added thereto and the mixture was subjected to filtration.

The crude product obtained by distilling off the solvent under reduced pressure was isolated by washing with hexane to obtain the title compound as a brown powder (4.27 g, yield: 68%).

HRMS (EI) m/z; calcd. 429.1694[M]+. found 429.1698.

$^1$H NMR (δppm in CDCl$_3$); 6.65-6.69 (m, 2H), 7.11 (t, 2H, J=7.4 Hz), 7.16 (d, 2H, J=8.9 Hz), 7.64-7.70 (m, 4H), 7.79 (d, 2H, J=8.9 Hz), 7.86 (dd, 2H, J=0.9, 7.6 Hz), 8.48 (d, 2H, J=8.9 Hz), 8.60 (d, 2H, J=8.1 Hz), 8.84 (d, 2H, J=7.1 Hz).

Example 22: Preparation of 6c-aza-14b-boratribenzo[c,g,p]chrysene

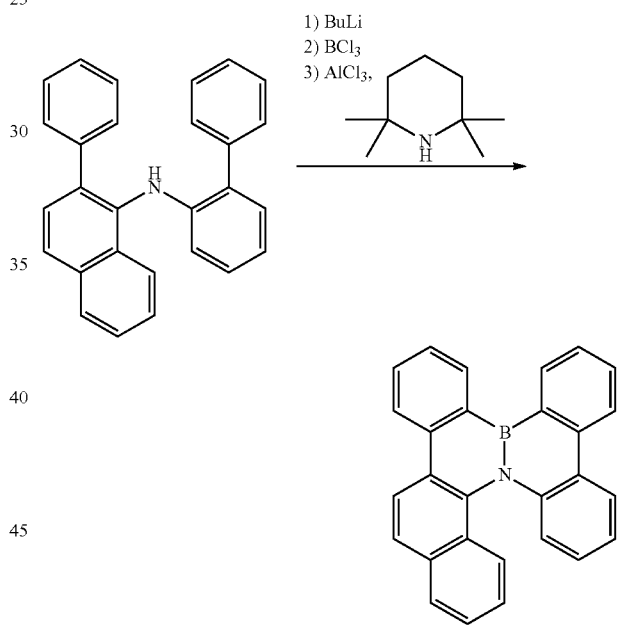

A hexane solution (0.940 mL, 1.60 M, 1.50 mmol) of butyllithium was added to N-([1,1'-biphenyl]-2-yl)-2-phenylnaphthalen-1-amine (0.559 g, 1.51 mmol) and toluene (7.5 mL) at −78° C. under an argon atmosphere, followed by stirring.

Ten minutes later, the mixture was warmed to 0° C. and further stirred for one and a half hours.

A heptane solution (1.50 mL, 1.00 M, 1.50 mmol) of boron trichloride was added at −78° C. and stirred at room temperature for 12 hours.

After distilling off the solvent under a reduced pressure, 1,2-dichlorobenzene was added. Thereafter, aluminum trichloride (0.800 g, 6.00 mmol) and 2,2,6,6-tetramethylpiperidine (0.510 mL, 3.00 mmol) were added and the mixture was stirred at 150° C. for 12 hours.

1,4-Diazabicyclo[2.2.2.]octane (0.675 g, 6.01 mmol) was added thereto and the mixture was subjected to filtration.

The crude product obtained by distilling off the solvent under reduced pressure was isolated by GPC to obtain the title compound as a brown powder (0.132 g, yield: 23%).

HRMS (EI) m/z; calcd. 379.1532[M]⁺. found 379.1521.

¹H NMR (δppm in CDCl₃); 7.04-7.06 (m, 2H), 7.10-7.15 (m, 1H), 7.18-7.22 (m, 1H), 7.37-7.41 (m, 1H), 7.58-7.62 (m, 2H), 7.63-7.67 (m, 1H), 7.77-7.89 (m, 4H), 8.30 (d, 1H, J=7.6 Hz), 8.44 (d, 1H, J=8.5 Hz), 8.46 (d, 1H, J=8.0 Hz), 8.51 (d, 1H, J=8.0 Hz), 8.74-8.77 (m, 2H).

Example 23: Preparation of 4b-aza-14b-boratribenzo[a,c,f]tetraphene

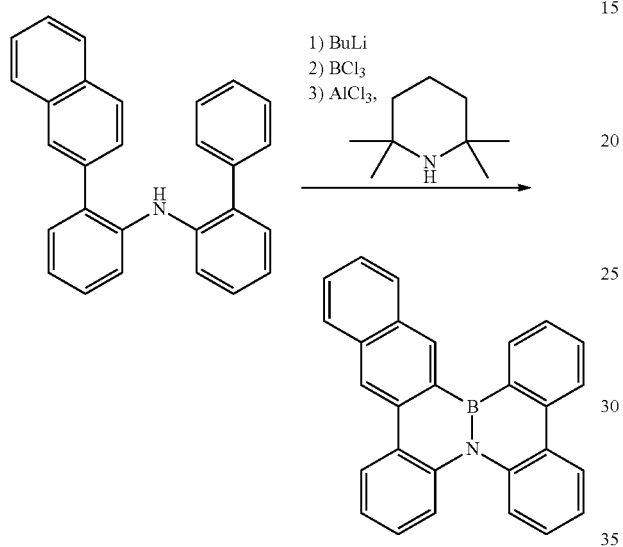

A hexane solution (0.625 mL, 1.60 M, 1.00 mmol) of butyllithium was added to N-(2-(naphthalen-2-yl)phenyl)-[1,1'-biphenyl]-2-amine (0.370 g, 0.996 mmol) and toluene (5.0 mL) at −78° C. under an argon atmosphere, followed by stirring.

Fifteen minutes later, the mixture was warmed to 0° C. and further stirred for one and a half hours.

A heptane solution (1.00 mL, 1.00 M, 1.00 mmol) of boron trichloride was added at −78° C., and the mixture was stirred at room temperature for 12 hours.

After distilling off the solvent under a reduced pressure, 1,2-dichlorobenzene was added thereto. Thereafter, aluminum trichloride (1.07 g, 8.00 mmol) and 2,2,6,6-tetramethylpiperidine (0.680 mL, 4.00 mmol) were added thereto, and the mixture was stirred at 150° C. for 12 hours.

1,4-Diazabicyclo[2.2.2.]octane (0.897 g, 8.00 mmol) was added thereto and the mixture was subjected to filtration.

The crude product obtained by distilling off the solvent under reduced pressure was isolated by GPC to obtain the title compound as a brown powder (0.219 g, yield: 55%).

HRMS (EI) m/z; calcd. 379.1532[M]⁺. found 379.1538.

¹H NMR (δppm in CDCl₃); 7.26-7.38 (m, 4H), 7.49-7.53 (m, 1H), 7.54-7.60 (m, 1H), 7.61-7.65 (m, 1H), 7.75-7.79 (m, 1H), 7.97-8.07 (m, 4H), 8.32 (dd, 1H, J=1.6, 7.8 Hz), 8.38-8.43 (m, 2H), 8.73 (s, 1H), 8.78 (dd, 1H, J=1.4, 7.6 Hz), 9.10 (s, 1H).

Example 24: Preparation of 2,11-dibromo-6c-aza-16b-boradibenzo[c,p]naphtho[1,2-g]chrysene

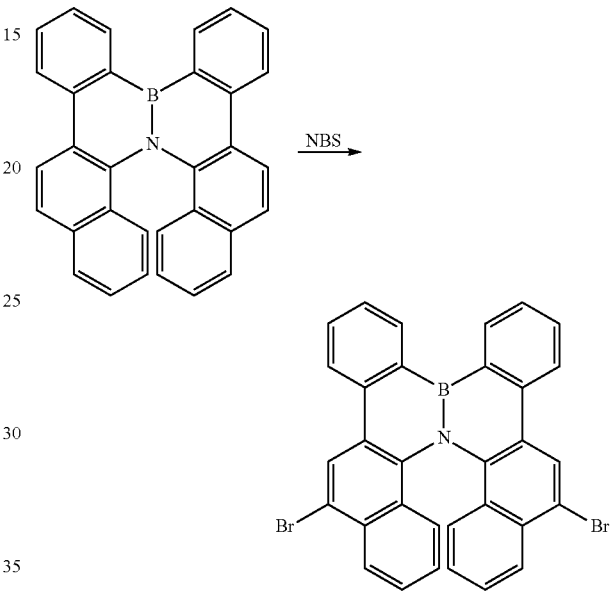

N-Bromosuccinimide (0.0444 g, 0.249 mmol) was added to 6c-aza-16b-boradibenzo[c,p]naphtho[1,2-g]chrysene (0.0427 g, 0.996 mmol) and methylene chloride (1.0 mL) at room temperature, followed by stirring for 6 hours.

The crude product obtained by distilling off the solvent under reduced pressure was isolated by GPC to obtain the title compound as a brown powder (0.0222 g, yield: 38%).

HRMS (EI) m/z; calcd. 586.9887[M]⁺. found 586.9885.

¹H NMR (δppm in CDCl₃); 6.79 (dt, 2H, J=1.4, 7.7 Hz), 7.19-7.24 (m, 4H), 7.70 (t, 2H, J=6.7 Hz), 7.90 (dt, 2H, J=1.3, 7.4 Hz), 8.12 (d, 2H, J=8.5 Hz), 8.55 (d, 2H, J=8.1 Hz), 8.80 (s, 2H), 8.84 (d, 2H, J=6.7 Hz).

Example 25: Preparation of 8b,11b,14b-triaza-22b,25b,28b-triboraoctabenzo[a,c,fg,jk,n,p,st,wx]hexacene

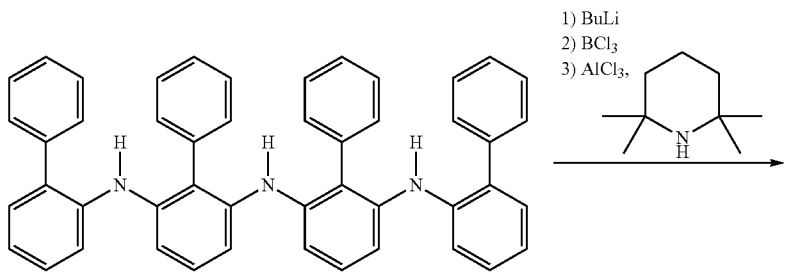

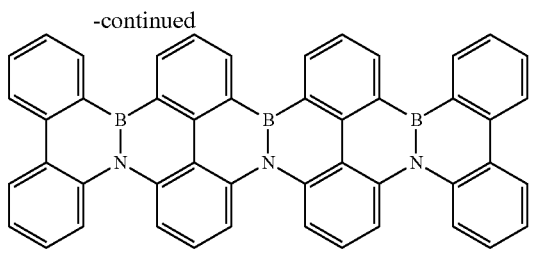

A hexane solution (3.68 mL, 1.63 M, 6.00 mmol) of butyllithium was added to $N^2$-([1,1'-biphenyl]-2-yl)-$N^6$-(6-([1,1'-biphenyl]-2-ylamino)-[1,1'-biphenyl]-2-yl)-[1,1'-biphenyl]-2,6-diamine (1.31 g, 2.00 mmol) and toluene (20 mL) at −78° C. under an argon atmosphere, followed by stirring.

One hour later, the mixture was warmed to 0° C. and further stirred for one hour.

A heptane solution (6.00 mL, 1.00 M, 6.00 mmol) of boron trichloride was added at −78° C. and stirred at room temperature for 12 hours.

After distilling off the solvent under a reduced pressure, 1,2-dichlorobenzene (40 mL) was added thereto. Thereafter, aluminum trichloride (4.01 g, 30.0 mmol) and 2,2,6,6-tetramethylpiperidine (1.74 g, 11.3 mmol) were added thereto and the mixture was stirred at 150° C. for 12 hours.

1,4-Diazabicyclo[2.2.2.]octane (3.36 g, 30.0 mmol) was added thereto and the mixture was subjected to filtration.

The crude product obtained by distilling off the solvent under reduced pressure was isolated by HPLC and GPC to obtain the title compound.

Example 26: Preparation of 9b,22b-diaza-4b,17b-diboratetrabenzo[a,c,f,m]phenanthro[9,10-k]tetraphene

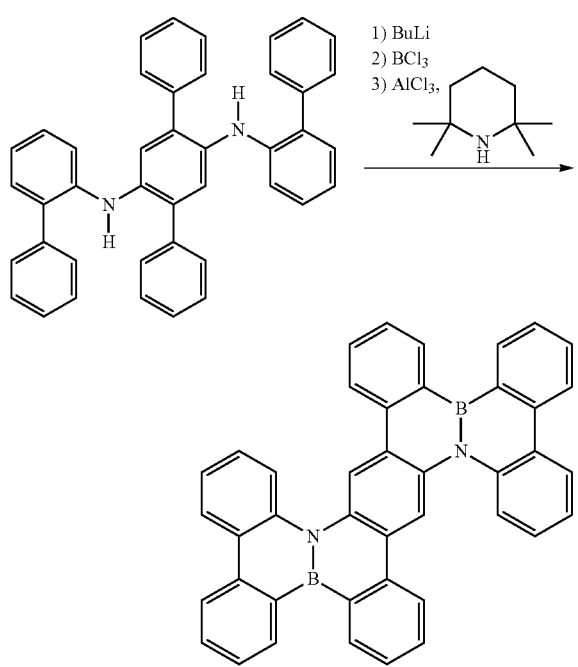

A hexane solution (2.45 mL, 1.63 M, 4.00 mmol) of butyllithium was added to $N^{2'},N^{5'}$-di([1,1'-biphenyl]-2-yl)-[1,1':4',1''-terphenyl]-2',5'-diamine (1.13 g, 2.00 mmol) and toluene (20 mL) at −78° C. under an argon atmosphere, followed by stirring. One hour later, the mixture was warmed to 0° C. and further stirred for one hour.

Thereafter, a heptane solution (4.00 mL, 1.00 M, 4.00 mmol) of boron trichloride was added at −78° C., and stirred at room temperature for 12 hours.

After distilling off the solvent under a reduced pressure and adding 1,2-dichlorobenzene (40 mL), aluminum trichloride (2.67 g, 20.0 mmol) and 2,2,6,6-tetramethylpiperidine (1.16 g, 7.50 mmol) were added thereto and the mixture was stirred at 150° C. for 12 hours.

1,4-Diazabicyclo[2.2.2.]octane (2.24 g, 20.0 mmol) was added thereto and the mixture was subjected to filtration.

The crude product obtained by distilling off the solvent under reduced pressure was isolated by HPLC and GPC to obtain the title compound.

Example 27: Preparation of 2,7-diphenyl-4b-aza-12b-boradibenzo[g,p]chrysene

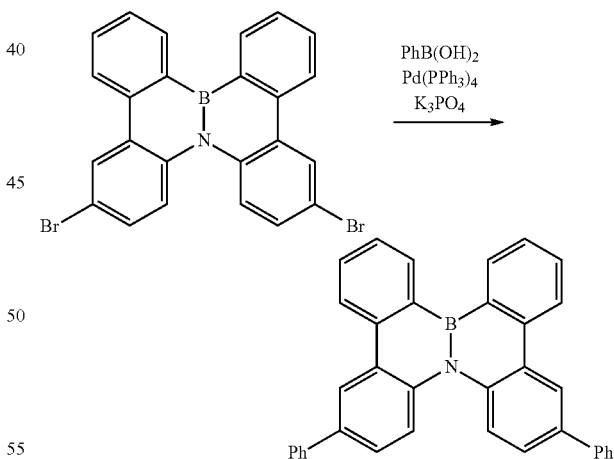

Toluene (5.0 mL) was added to 2,7-dibromo-4b-aza-12b-boradibenzo[g,p]chrysene (0.243 g, 0.50 mmol), phenylboronic acid (0.122 g, 1.00 mmol), tetrakis(triphenylphosphine)palladium (0.023 g, 0.02 mmol), and potassium phosphate (0.425 g, 2.00 mol) at 0° C. under an argon atmosphere, followed by stirring at room temperature for 12 hours.

After Celite® filtration, the crude product obtained by distilling off the solvent under reduced pressure was isolated by HPLC and GPC to obtain the title compound.

Example 28: Preparation of bis(biphenyl-2-yl)amine

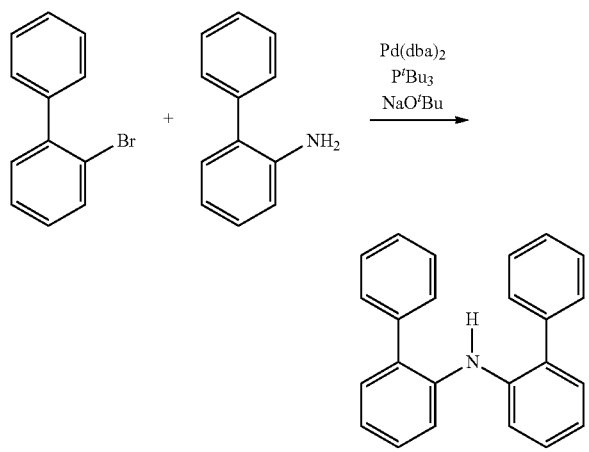

2-Bromobiphenyl (23.1 g, 0.10 mol) was added to 2-aminobiphenyl (16.9 g, 0.10 mol), bis(dibenzylideneacetone)palladium (0.575 g, 1.0 mmol), sodium tert-butoxide (14.4 g, 0.15 mol) and toluene (100 mL) at 0° C. under an argon atmosphere, followed by stirring at room temperature for 7 hours.

After Florisil® filtration, the brown oily substance obtained by distilling off the solvent under reduced pressure was subject to trituration using hexane to obtain the title compound as a white powder (32.1 g, yield: 98%).

$^1$H NMR ($\delta$ppm in CDCl$_3$); 5.79 (s, 1H), 6.92 (t, J=7.2 Hz, 2H), 7.17-7.27 (m, 14H), 7.40 (d, 2H, J=8.1 Hz); $^{13}$C NMR ($\delta$ppm in CDCl$_3$) 117.0, 120.8, 127.2, 128.1, 128.7, 129.0, 130.6, 132.0, 138.9, 140.1.

Example 29: Measurement of the carrier mobility of 4b-aza-12b-boradibenzo[g,p]chrysene A glass substrate (26 mm×28 mm×0.5 mm, manufactured by Nippon Sheet Glass Co., Ltd.) was used as a transparent support substrate.

This transparent support substrate was mounted in the substrate holder of a commercially available vapor deposition apparatus together with a metal mask to obtain a lower aluminum electrode of 2 mm width.

Subsequently, a tungsten vapor deposition boat having aluminum thereon was set in the vapor deposition apparatus.

The vacuum chamber was decompressed to $5 \times 10^{-3}$ Pa or lower, and the vapor deposition boat was warmed to form a translucent lower aluminum electrode in such a manner that its film thickness would become 10 nm. The vapor deposition rate was 0.05 to 1 nm/sec.

Subsequently, a metal mask for forming an organic layer that was designed to cover the lower aluminum electrode was mounted on the substrate holder and set in a vapor deposition apparatus together with a vapor deposition boat made of molybdenum that held "4b-aza-12b-boradibenzo[g,p]chrysene" therein.

The vacuum chamber was decompressed to $5 \times 10^{-3}$ Pa or lower and the vapor deposition boat was warmed to deposit "4b-aza-12b-boradibenzo[g,p]chrysene." Here, the film thickness was 6 μm and the deposition rate was 0.1 to 10 nm/sec.

Subsequently, a metal mask for forming an upper aluminum electrode was mounted on the substrate holder and it was set in a vapor deposition apparatus together with a vapor deposition boat made of tungsten having aluminum thereon.

The metal mask was designed so that the overlapping area having the organic layers of the upper and lower aluminum electrodes therebetween became 4 mm$^2$.

The vacuum chamber was decompressed to $5 \times 10^{-2}$ Pa or lower, and the vapor deposition boat was warmed to form an upper electrode having a film thickness of 50 nm. The deposition rate was 0.05 to 1 nm/sec.

The carrier mobility was measured using a time-of-flight method.

The measurement was performed using a commercially available measurement apparatus (TOF-401, manufactured by Sumitomo Heavy Industries Advanced Machinery Co., Ltd.).

A nitrogen gas laser was used as the excitation light source.

While applying an appropriate voltage across the upper and the lower aluminum electrodes, light was irradiated from the translucent lower aluminum electrode side, and the transient photocurrent was observed to obtain the mobility.

The procedure for deriving the mobility based on analysis of the transient photocurrent waveform is disclosed in pp. 69-70 of "Organic electroluminescence materials and displays" (published by CMC Co., Ltd.).

The measurement results revealed that when an electric field strength of 0.5 MV/cm was applied, "4b-aza-12b-boradibenzo[g,p]chrysene" had an electron mobility of $2 \times 10^{-3}$ (cm$^2$/Vsec) and a hole mobility of $4 \times 10^{-4}$ (cm$^2$/Vsec).

Example 30: Measurement of mobility in 6c-aza-16b-boradibenzo[c,p]naphtho[1,2-g]chrysene A sample was prepared in the same manner as in Example 29 except that "6c-aza-16b-boradibenzo[c,p]naphtho[1,2-g]chrysene" was used instead of "4b-aza-12b-boradibenzo[g,p]chrysene" and the thickness of the organic layer deposited became 8.2 μm. The mobility was observed in the same manner.

The measurement results revealed that when an electric field strength of 0.5 MV/cm was applied, the "6c-aza-16b-boradibenzo[c,p]naphtho[1,2-g]chrysene" had a hole mobility of $4.6 \times 10^{-4}$ (cm$^2$/Vsec).

The invention claimed is:

1. A polycyclic aromatic compound or a salt thereof represented by the following formula (I):

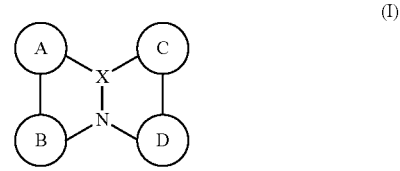

wherein

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table; and ring A, ring B, ring C, and ring D are the same or different, and each represents an optionally substituted phenyl ring, an optionally substituted phenyl ring fused to an aryl or heteroaryl ring, an optionally substituted heteroaromatic ring, or an optionally substituted heteroaromatic ring fused to an aryl or heteroaryl ring, wherein at least one of ring A, ring B, ring C, and ring D is an optionally substituted heteroaromatic ring, or an optionally substituted heteroaromatic ring fused to an aryl or heteroaryl ring, wherein the heteroaromatic ring of ring A, ring B, ring C, and ring D is selected from the group consisting of thiophene, pyrrole and pyridine, and wherein the compound represented by formula (I) is not a heterofullerene.

2. The polycyclic aromatic compound or salt thereof according to claim 1, represented by the following formula (II):

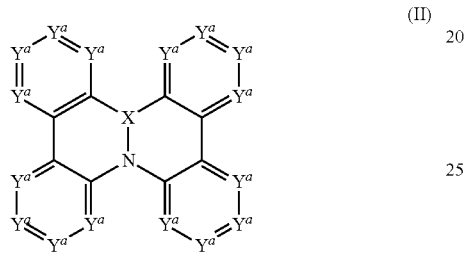

(II)

wherein $Y^a$s are the same or different, and each represents C— or N; or two adjacent $Y^a$s on the same ring, together with a bond therebetween, form N—, or S; provided that all $Y^a$s do not represent C— at the same time; and X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table.

3. The polycyclic aromatic compound or salt thereof according to claim 1, represented by any one of the following formulae (II-2) to (II-54):

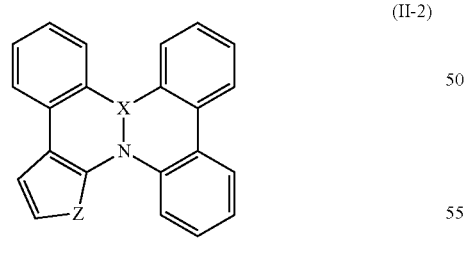

(II-2)

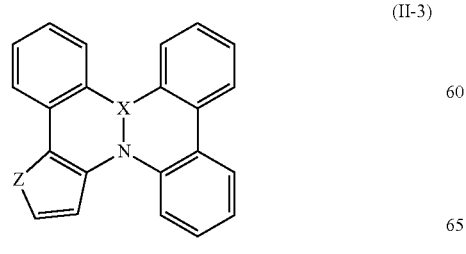

(II-3)

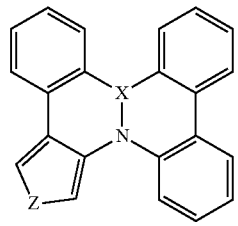

(II-4)

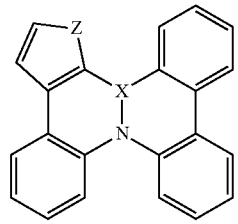

(II-5)

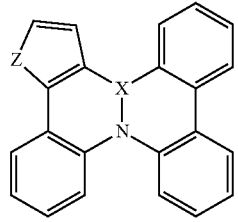

(II-6)

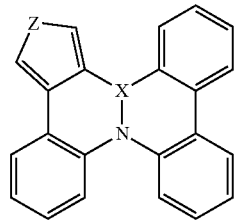

(II-7)

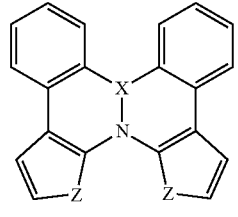

(II-8)

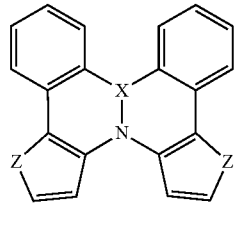

(II-9)

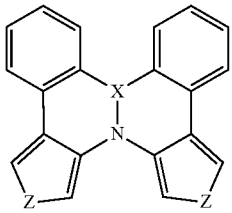

(II-10)

(II-11) 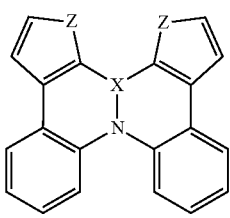
(II-12) 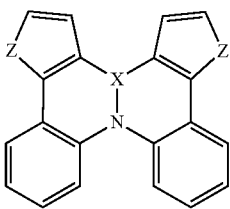
(II-13) 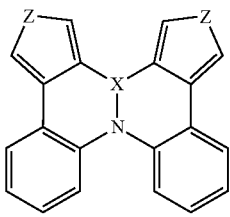
(II-14) 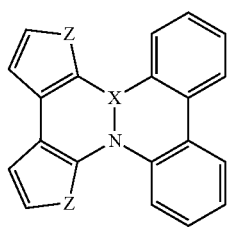
(II-15) 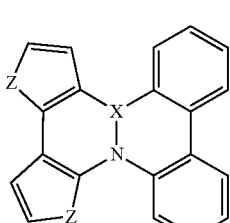
(II-16) 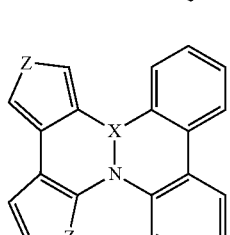
(II-17) 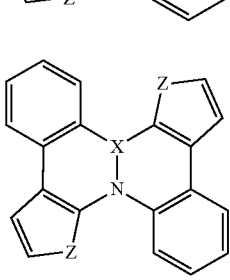
(II-18) 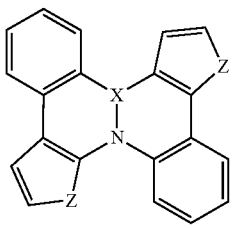
(II-19) 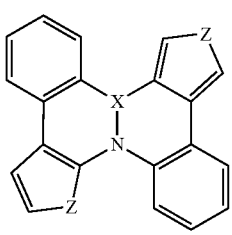
(II-20) 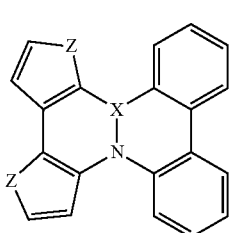
(II-21) 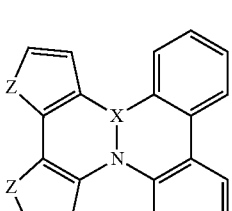
(II-22) 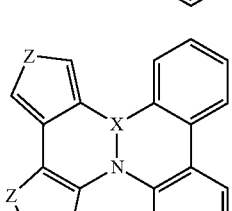
(II-23) 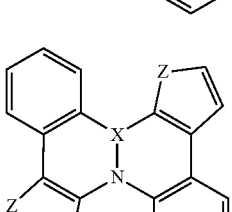
(II-24) 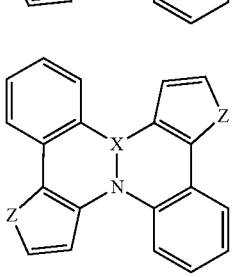

-continued
(II-25) 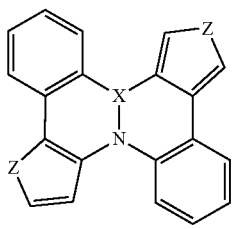
(II-26) 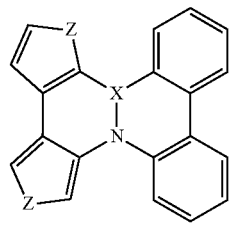
(II-27) 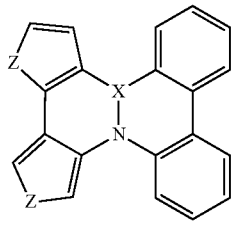
(II-28) 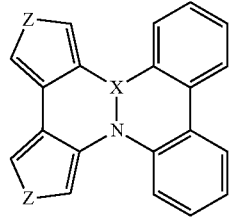
(II-29) 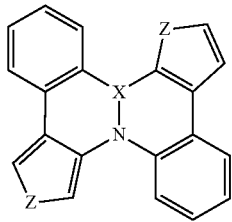
(II-30) 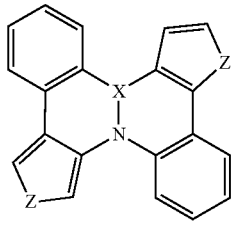
(II-31) 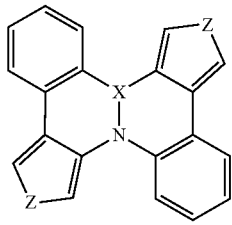
-continued
(II-32) 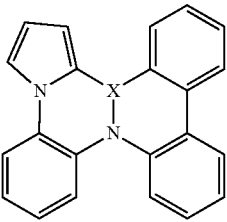
(II-33) 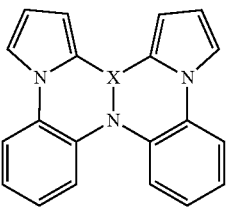
(II-34) 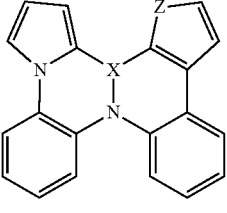
(II-35) 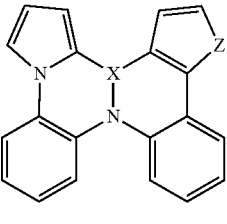
(II-36) 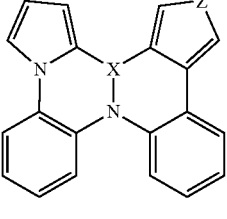
(II-37) 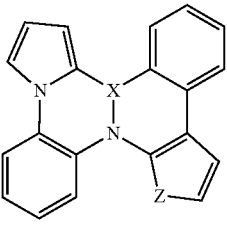
(II-38) 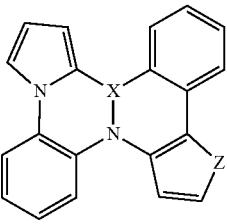

(II-39) 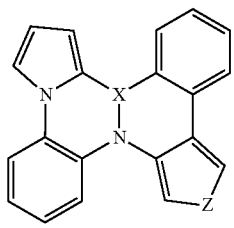
(II-40) 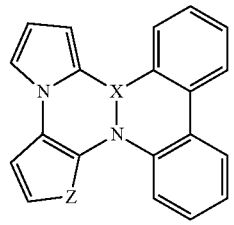
(II-41) 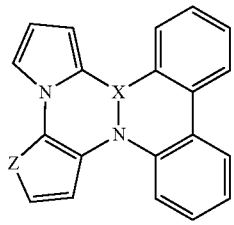
(II-42) 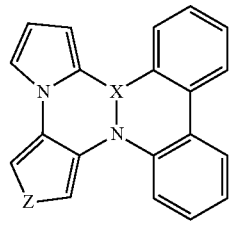
(II-43) 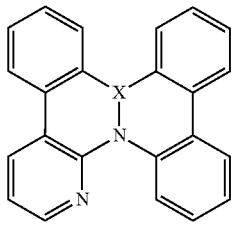
(II-44) 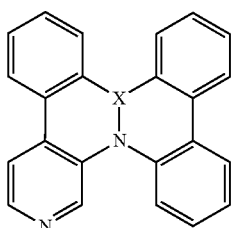
(II-45) 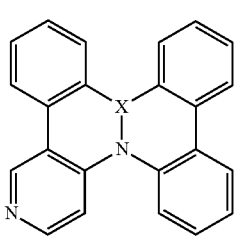
(II-46) 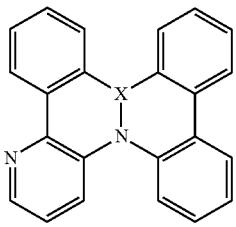
(II-47) 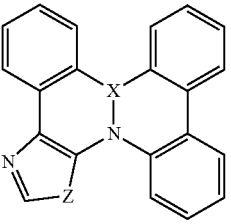
(II-48) 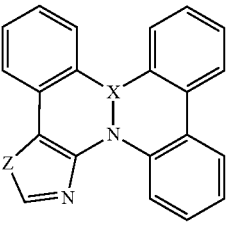
(II-49) 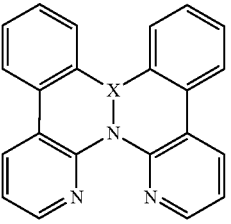
(II-50) 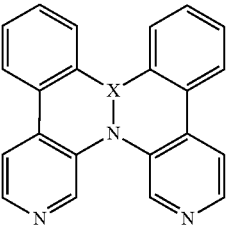
(II-51) 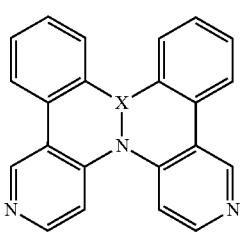
(II-52) 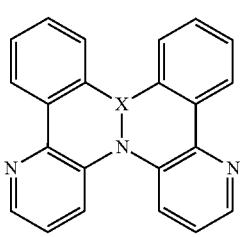

-continued

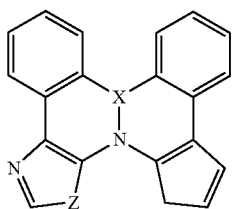
(II-53)

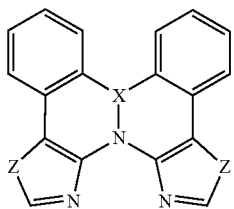
(II-54)

wherein

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table; and Z represents S, or N—.

4. The polycyclic aromatic compound or salt thereof according to claim 1 represented by the following formula (II'):

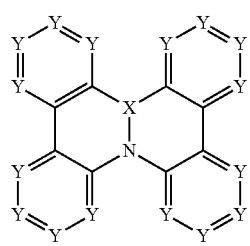
(II')

wherein

Ys are the same or different, and each represents CR or N; or two adjacent Ys on the same ring, together with a bond therebetween, form NR, or S; provided that all Ys do not represent C— at the same time;

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table;

R represents a hydrogen atom, halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, cyano group, nitro group, amino group, monoalkylamino group, monoarylamino group, monoheteroarylamino group, carbazole group, $C_{1-20}$ alkoxycarbonylamino group, carbamoyl group, mono- or di-alkylcarbamoyl group, sulfamoyl group, mono- or di-alkylsulfamoyl group, $C_{1-20}$ alkylsulfonylamino group, $C_{1-20}$ alkylcarbonylamino group, aryl group, heteroaryl group, $C_{1-20}$ alkoxycarbonyl group, carboxyl group, 5-tetrazolyl group, sulfo group (—$SO_2OH$), fluorosulfonyl group, $SR^a$, $N(R^a)_2$, $B(R^a)_2$, $Si(R^a)_3$, or —C≡C—$Si(R^a)_3$, (wherein $R^a$ represents an optionally substituted alkyl group, an optionally substituted aryl group, or an optionally substituted heteroaryl group; or two $R^a$s, together with an atom bound thereto, may form a bicyclic group or a tricyclic group optionally having a heteroatom);

provided that, the alkyl group, alkenyl group, alkynyl group, and alkoxy group are each optionally substituted with 1 to 3 atoms or groups, selected from the group consisting of halogen atom, hydroxy group, $C_{1-20}$ alkoxy group, aryloxy group, amino group, carbazole group, $N(R^a)_2$ (wherein $R^a$ is as defined above), trifluoromethyl group, $C_{2-12}$ perfluoroalkyl group, $C_{3-8}$ cycloalkyl group, aryl group, and heteroaryl group; and the aryl group, aryl moiety, heteroaryl group, heteroaryl moiety, and carbazole group are each optionally substituted with 1 to 5 atoms or groups, selected from the group consisting of halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, cyano group, nitro group, amino group, carbazole group, monoalkylamino group, monoarylamino group, monoheteroarylamino group, $N(R^a)_2$ (wherein $R^a$ is as defined above), carbamoyl group, mono- or di-alkylcarbamoyl group, sulfamoyl group, mono- or di-alkylsulfamoyl group, $C_{1-20}$ alkylcarbonyl group, $C_{1-20}$ alkylsulfonyl group, $C_{1-20}$ alkylsulfonylamino group, $C_{1-20}$ alkylcarbonylamino group, methylenedioxy group, heteroaryl group, and aryl group, (wherein the aryl group is optionally substituted with 1 to 5 atoms or groups, selected from the group consisting of halogen atom, $C_{1-20}$ alkyl group, $C_{3-8}$ cycloalkyl group, $C_{2-20}$ alkenyl group, $C_{2-20}$ alkynyl group, hydroxy group, trifluoromethyl group, $C_{2-12}$ perfluoroalkyl group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, methylenedioxy group, cyano group, nitro group, amino group, carbazole group, and $N(R^a)_2$ (wherein $R^a$ is as defined above)); or, two adjacent Rs on the same ring, together with a carbon atom bound thereto, form a five- or six-membered monocyclic aromatic group, bicyclic aromatic group, or tricyclic aromatic group optionally having a heteroatom; or three adjacent Rs on the same ring, together with a carbon atom bound thereto, form a bicyclic aromatic group or a tricyclic group optionally having a heteroatom.

5. The polycyclic aromatic compound or salt thereof according to claim 1 represented by the following formulae (III') to (XXIII'):

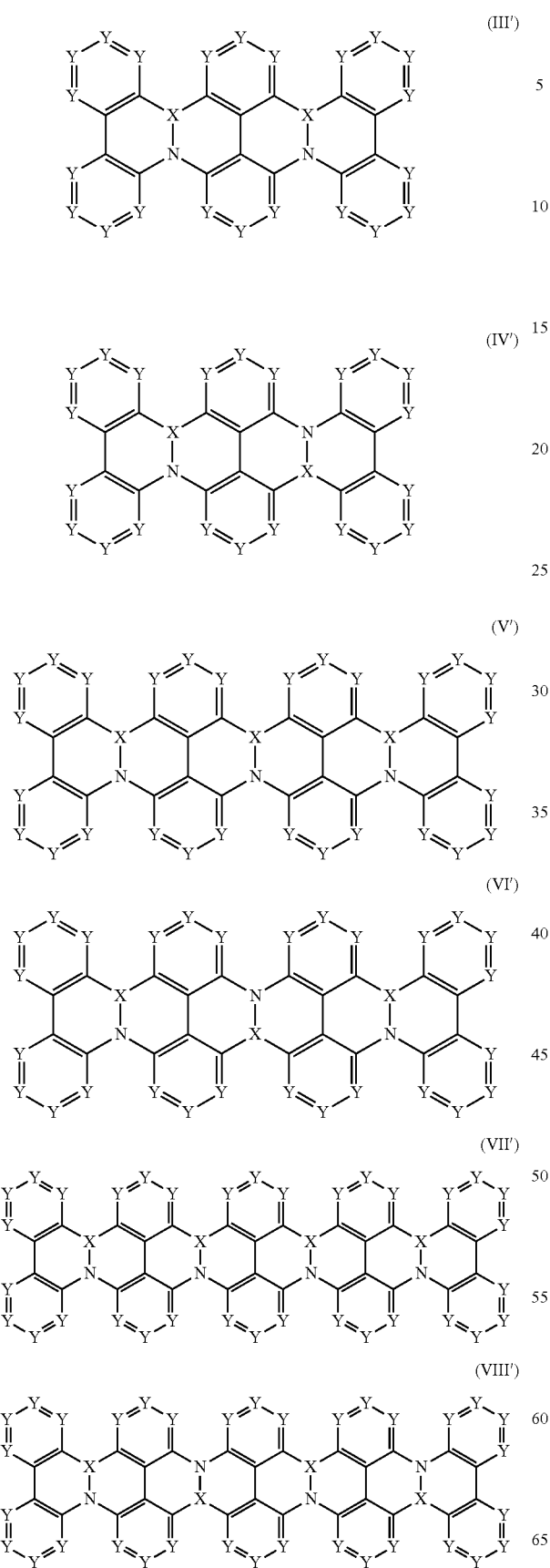
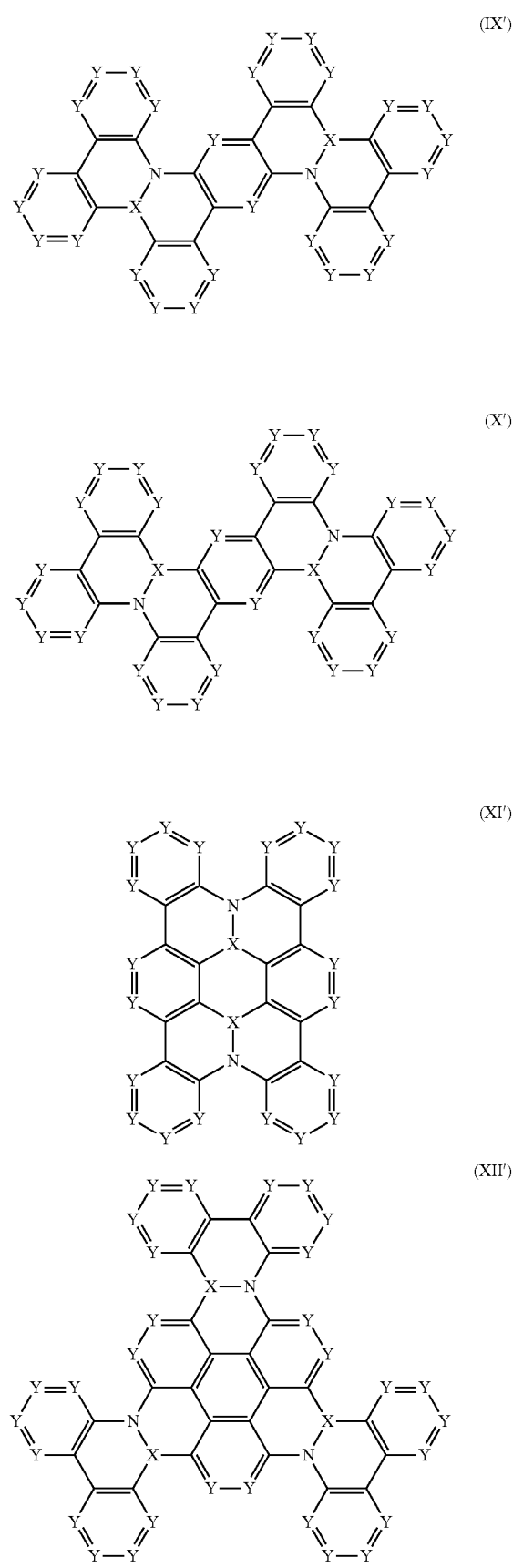

-continued
(XIII')
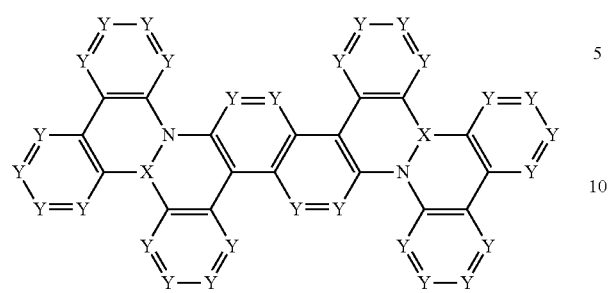
(XIV')
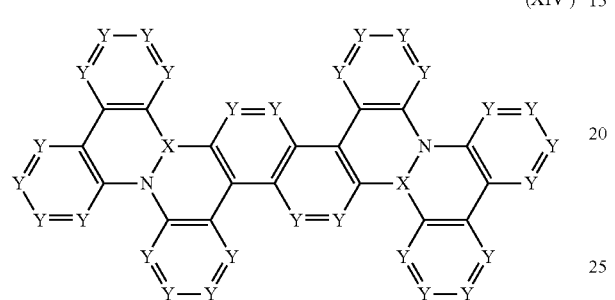
(XV')
(R)₃
(XVI')
(R)₃  (R)₃
(XVII')
(R)₂
(XVIII')
(R)₃  (R)₃
-continued
(XIX')
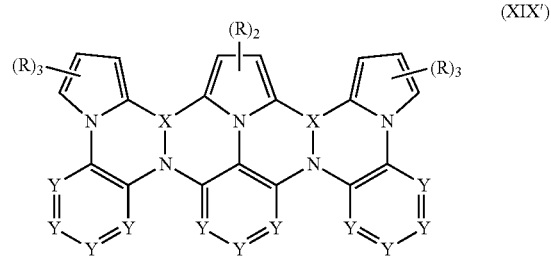
(XX')
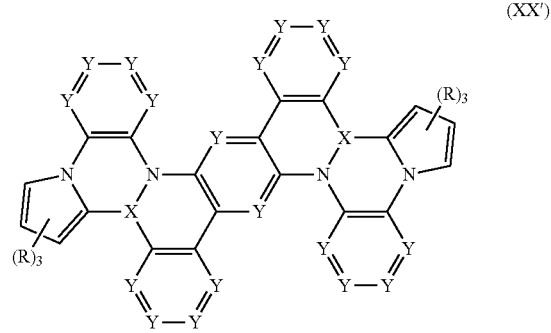
(XXI')
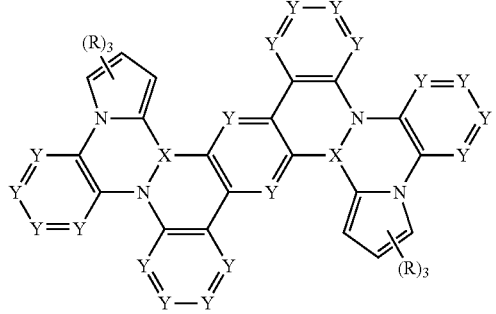
(XXII')
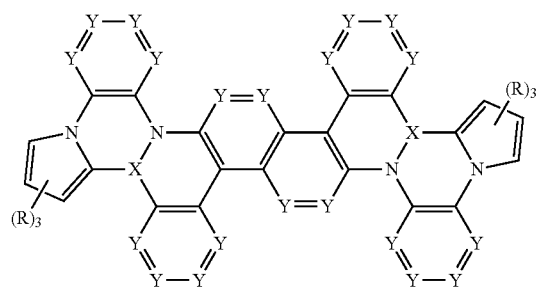
(XXIII')
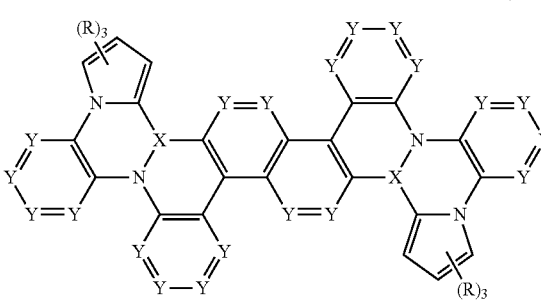
wherein
Ys are the same or different, and each represents CR or N; or two adjacent Ys on the same ring, together with a bond therebetween, form NR, or S; provided that all Ys do not represent C— at the same time;

X represents B, P, P=O, P=S, P=Se, As, As=O, As=S, As=Se, Sb, Sb=O, Sb=S, Sb=Se, an optionally substituted metal in groups 3 to 11 in the periodic table, or an optionally substituted metal or metalloid in group 13 or 14 of the periodic table; and R represents a hydrogen atom, halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di- heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, cyano group, nitro group, amino group, monoalkylamino group, monoarylamino group, monoheteroarylamino group, carbazole group, $C_{1-20}$ alkoxycarbonylamino group, carbamoyl group, mono- or di-alkylcarbamoyl group, sulfamoyl group, mono- or di-alkylsulfamoyl group, $C_{1-20}$ alkylsulfonylamino group, $C_{1-20}$ alkylcarbonylamino group, aryl group, heteroaryl group, $C_{1-20}$ alkoxycarbonyl group, carboxyl group, 5-tetrazolyl group, sulfo group (—SO$_2$OH), fluorosulfonyl group, SR$^a$, N(R$^a$)$_2$, B(R$^a$)$_2$, Si(R$^a$)$_3$, or —C≡C—Si(R$^a$)$_3$ (wherein R$^a$ represents an optionally substituted alkyl group, an optionally substituted aryl group, or an optionally substituted heteroaryl group; or two R$^a$s, together with an atom bound thereto, may form a bicyclic group or a tricyclic group optionally having a heteroatom);

provided that, the alkyl group, the alkenyl group, the alkynyl group, and the alkoxy group are each optionally substituted with 1 to 3 atoms or groups, selected from the group consisting of halogen atom, hydroxy group, $C_{1-20}$ alkoxy group, aryloxy group, amino group, carbazole group, N(R$^a$)$_2$ (wherein R$^a$ is as defined above), trifluoromethyl group, $C_{2-12}$ perfluoroalkyl group, $C_{3-8}$ cycloalkyl group, aryl group, and heteroaryl group; and the aryl group, aryl moiety, heteroaryl group, heteroaryl moiety, and carbazole group are each optionally substituted with 1 to 5 atoms or groups, selected from the group consisting of halogen atom, $C_{1-20}$ alkyl group, hydroxy $C_{1-20}$ alkyl group, trifluoromethyl group, $C_{2-12}$ perfluoroalkyl group, $C_{3-8}$ cycloalkyl group, $C_{2-20}$ alkenyl group, $C_{2-20}$ alkynyl group, mono- or di-aryl-substituted alkenyl group, mono- or di-heteroaryl-substituted alkenyl group, arylethynyl group, heteroarylethynyl group, hydroxy group, $C_{1-20}$ alkoxy group, aryloxy group, trifluoromethoxy group, trifluoroethoxy group, $C_{2-12}$ perfluoroalkoxy group, cyano group, nitro group, amino group, carbazole group, monoalkylamino group, monoarylamino group, monoheteroarylamino group, N(R$^a$)$_2$ (wherein R$^a$ is as defined above), carbamoyl group, mono- or di-alkylcarbamoyl group, sulfamoyl group, mono- or di-alkylsulfamoyl group, $C_{1-20}$ alkylcarbonyl group, $C_{1-20}$ alkylsulfonyl group, $C_{1-20}$ alkylsulfonylamino group, $C_{1-20}$ alkylcarbonylamino group, methylenedioxy group, heteroaryl group, and aryl group (wherein the aryl group is optionally substituted with 1 to 5 atoms or groups, selected from the group consisting of halogen atom, $C_{1-20}$ alkyl group, $C_{3-8}$ cycloalkyl group, $C_{2-20}$ alkenyl group, $C_{2-20}$ alkynyl group, hydroxy group, trifluoromethyl group, $C_{2-12}$ perfluoroalkyl group, $C_{1-20}$ alkoxy group, aryloxy group, trifluoromethoxy group, trifluoroethoxy group, $C_{2-12}$ perfluoroalkoxy group, $C_{1-20}$ alkylcarbonyl group, $C_{1-20}$ alkylsulfonyl group, methylenedioxy group, cyano group, nitro group, amino group, carbazole group, and N(R$^a$)$_2$ (wherein R$^a$ is as defined above); or, two adjacent Rs on the same ring, together with a carbon atom bound thereto, form a five- or six-membered monocyclic aromatic group, bicyclic aromatic group, or tricyclic aromatic group optionally having a heteroatom; or three adjacent Rs on the same ring, together with a carbon atom bound thereto, form a bicyclic aromatic group or a tricyclic aromatic group optionally having a heteroatom.

6. An electrochemical device comprising the compound according to claim 1.

7. The electrochemical device according to claim 6, wherein the device is an organic light-emitting element, an organic thin-film transistor, or an organic thin-film solar cell.

* * * * *